United States Patent [19]
Bundy

[11] 3,980,694
[45] Sept. 14, 1976

[54] 4-OXA PHENYL-SUBSTITUTED PGA COMPOUNDS

[75] Inventor: Gordon L. Bundy, Portage, Mich.

[73] Assignee: The Upjohn Company, Kalamazoo, Mich.

[22] Filed: Oct. 23, 1975

[21] Appl. No.: 625,178

Related U.S. Application Data

[60] Division of Ser. No. 459,759, April 11, 1974, Pat. No. 3,931,289, which is a continuation of Ser. No. 185,448, Sept. 30, 1971, abandoned, which is a continuation-in-part of Ser. No. 103,338, Dec. 31, 1970, abandoned.

[52] U.S. Cl. .......................... 260/473 A; 260/345.8; 260/520 B
[51] Int. Cl.² ......................................... C07C 69/76
[58] Field of Search .......... 260/473 A, 520 B, 345.8

[56] References Cited
UNITED STATES PATENTS
3,864,387   2/1975   Nelson ............................ 260/473 A FOREIGN PATENTS OR APPLICATIONS
7,118,204   4/1972   Netherlands .................... 260/473 A Primary Examiner—Paul J. Killos
Attorney, Agent, or Firm—Morris L. Nielsen

[57] ABSTRACT

This invention is a group of 3-oxa and 4-oxa phenyl-substituted PGE type, PGF type, PGA type and PGB type compounds, and processes for making those. These compounds are useful for a variety of pharmacological purposes, including anti-ulcer, inhibition of platelet aggregation, increase of nasal patency, labor inducement at term, and wound healing.

28 Claims, No Drawings

4-OXA PHENYL-SUBSTITUTED PGA COMPOUNDS

CROSS REFERENCE TO RELATED APPLICATIONS

This is a division, of application Ser. No. 459,759, filed Apr. 11, 1974, now U.S. Pat. No. 3,931,289 which is a continuation of my copending application Ser. No. 185,448, filed Sept. 30, 1971, now abandoned which was a continuation-in-part of my copending application Ser. No. 103,338 filed Dec. 31, 1970, and now abandoned.

DESCRIPTION OF THE INVENTION

This invention relates to compositions of matter, and to methods and intermediates for producing them. In particular, the several aspects of this invention relate to novel analogs of some of the known prostaglandins, for example, prostaglandin $E_1$ ($PGE_1$), prostaglandin $E_2$ ($PGE_2$), prostaglandin $F_1$ ($PGF_{1\alpha}$ and $PGF_{1\beta}$), prostaglandin $F_2$ ($PGF_{2\alpha}$ and $PGF_{2\beta}$), prostaglandin $A_1$ ($PGA_1$), prostaglandin $A_2$ ($PGA_2$), prostaglandin $B_1$ ($PGB_1$), prostaglandin $B_2$ ($PGB_2$), and the dihydro derivatives of $PGE_1$, $PGF_{1\alpha}$, $PGF_{1\beta}$, $PGA_1$, and $PGB_1$, to novel methods for producing those novel prostaglandin analogs, and to novel chemical intermediates useful in those novel methods.

Each of the above-mentioned known prostaglandins is a derivative of prostanoic acid which has the following structure and atom numbering:

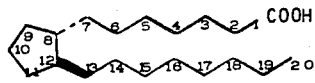

A systematic name for prostanoic acid is 7-[(2β-octyl)-cyclopent-1α-yl]heptanoic acid.

$PGE_1$ has the following structure:

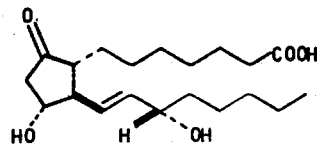

$PGF_{1\alpha}$ has the following structure:

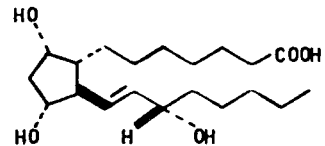

$PGF_{1\beta}$ has the following structure:

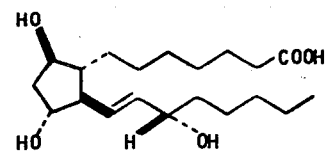

$PGA_1$ has the following structure:

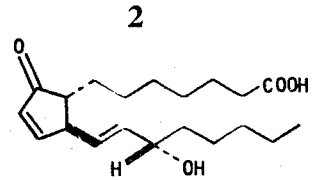

$PGB_1$ has the following structure:

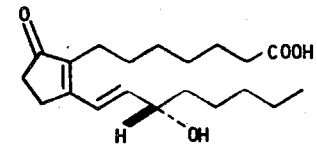

Each of the known prostaglandins $PGE_2$, $PGF_{2\alpha}$, $PGF_{2\beta}$, $PGA_2$, and $PGB_2$ has a structure the same as that shown for the corresponding $PG_1$ compound except that in each, C-5 and C-6 are linked with a cis carbon-carbon double bond. For example, $PGE_2$ has the following structure:

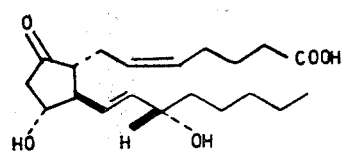

Each dihydro derivative of $PGE_1$, $PGF_{1\alpha}$, $PGF_{1\beta}$, $PGA_1$, and $PGB_1$ has a structure the same as that shown for the corresponding $PG_1$ compound except that in each, C-13 and C-14 are linked with a carbon-carbon single bond. For example, dihydro-$PGE_1$ has the following structure.

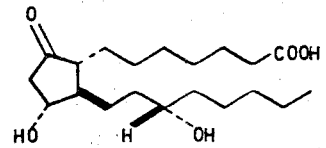

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In formulas, I, II, III, IV, V and VI, as well as in the formulas given hereinafter, broken line attachments to the cyclopentane ring indicate substituents in alpha configuration, i.e., below the plane of the cyclopentane ring. Heavy solid lime attachments to the cyclopentane ring indicate substituents in beta configuration, i.e., above the plane of the cyclopentane ring.

Prostaglandins with carboxyl-terminated side chains attached to the cyclopentane ring in beta configuration are also known. These are derivatives of 8-iso-prostanoic acid which has the following formula:

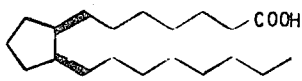   VII

A systematic name for 8-iso-prostanoic acid is 7-[(2β-octyl)cyclopent-1β-yl]heptanoic acid.

The novel prostaglandin analogs of this invention each have an oxa oxygen (—O—) in place of the methylene (—CH$_2$—) moiety at the 3-position or at the 4-position of the prostanoic acid structure (1) or the 8-iso-prostanoic acid structure (VII). The novel prostaglandin analogs of this invention also each have a benzene ring as part of the C-13 to C-20 chain of the prostanoic acid or 8-iso-prostanoic acid structure. That benzene ring is present as a substituted or unsubstituted phenyl moiety attached as a substituent to one of the methylenes between C-15 and the terminal methyl of the prostanoic acid or 8-iso-prostanoic acid structure. Alternatively, the substituted or unsubstituted phenyl moiety is attached to the terminal or omega carbon of the C-16 to C-20 portion of the chain, replacing one of the hydrogens of the terminal methyl, the entire terminal methyl, or the terminal methyl plus 1 to 4 of the methylenes adjacent to that terminal methyl. For example, three of the novel prostaglandin analogs of this invention are represented by the formula:

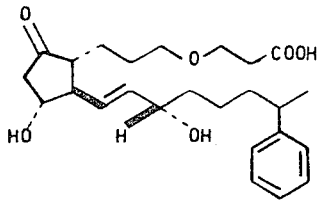   VIII

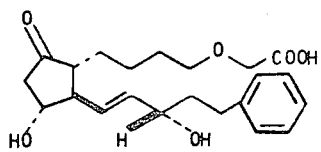   IX

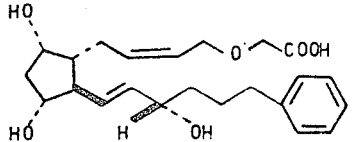   X

Based upon its relationship to PGE$_1$ and prostanoic acid, the compound of formula VIII is named 4-oxa-19-phenyl-PGE$_1$. Similarly, the compound of formula IX is named 3-oxa-17-phenyl-18,19,20-trinor-PGE$_1$, and the compound of formula X is named 3-oxa-18-phenyl-19,20-dinor-PGF$_{2\alpha}$. In those names, 3-oxa and 4-oxa indicate an oxa oxygen (—O—) in place of the 3-methylene and 4-methylene, respectively, of PGE$_1$. Also, in formulas IX and X, trinor and dinor indicate absence of the terminal —CH$_2$—CH$_2$—CH$_3$ and the terminal —CH$_2$—CH$_3$, respectively, of PGE$_1$ and PGF$_{2\alpha}$. The words nor, dinor, trinor, tetranor, and pentanor in the names given here and hereinafter for novel prostaglandins of this invention are to be construed as indicating the number of carbon atoms missing from the C-16 to C-20 position of the prostanoic acid carbon skeleton. The phenyl or substituted phenyl moiety is attached to the remaining portion of the prostanoic acid skeleton, i.e., to C-19 for the nor-compounds, to C-18 for the dinor compounds, to C-17 for the trinor compounds, to C-16 for the tetranor compounds and to C-15 for the pentanor compounds.

Some of the novel prostaglandin analogs of this invention differ structurally in other ways from the known prostanoic acid derivatives, having for example, more or fewer carbon atoms in the C-1 to C-7 chain of prostanoic acid, and having one or more alkyl and/or fluoro substituents in that chain or in the C-13 to C-20 chain of prostanoic acid.

The following formulas represent the novel 3-oxa and 4-oxa phenyl-substituted prostaglandin analogs of this invention:

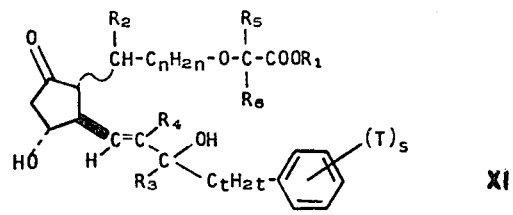   XI

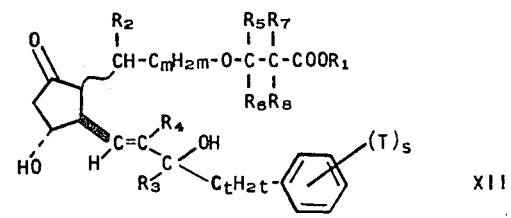   XII

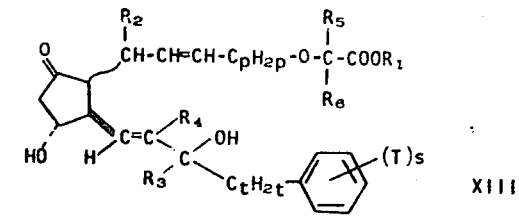   XIII

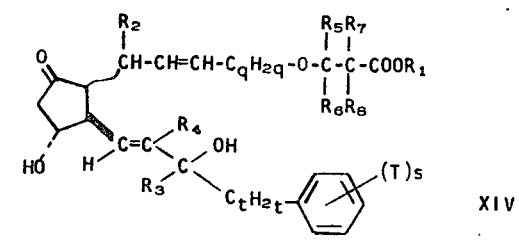   XIV

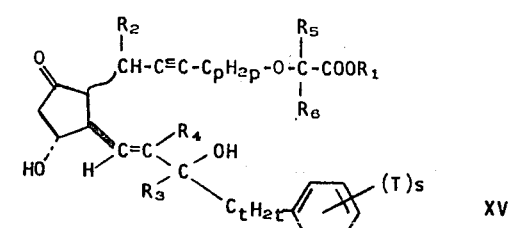   XV

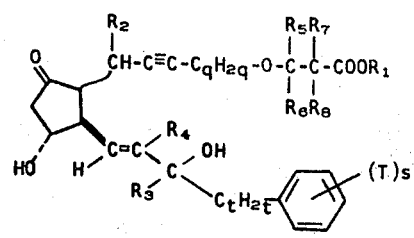 XVI
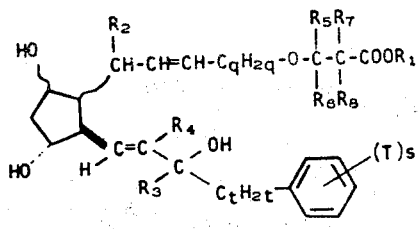 XXII
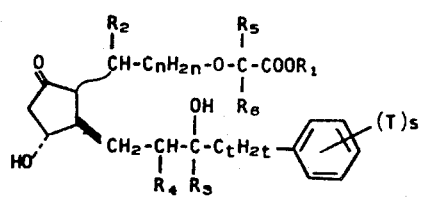 XVII
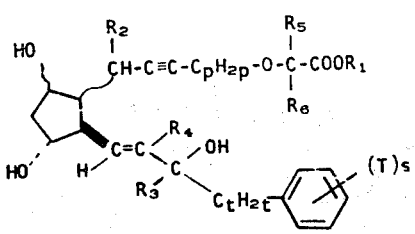 XXIII
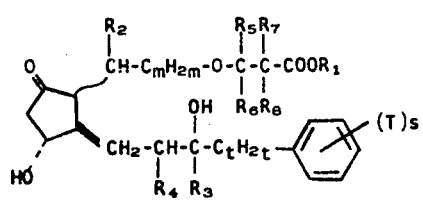 XVIII
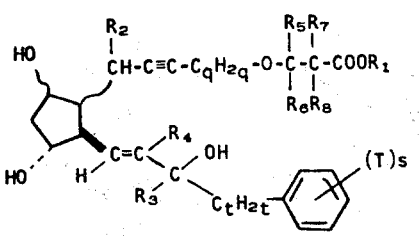 XXIV
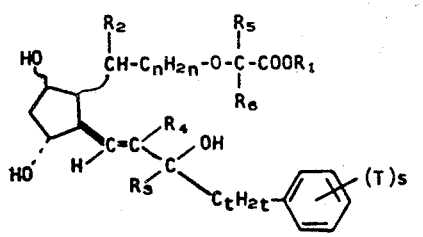 XIX
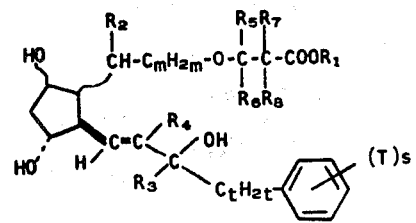 XX
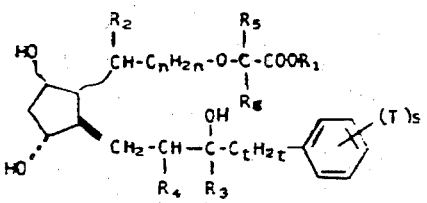 XXV
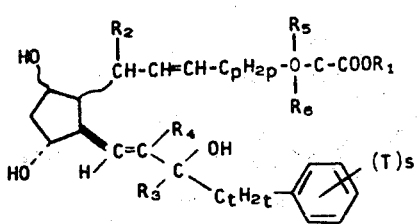 XXI
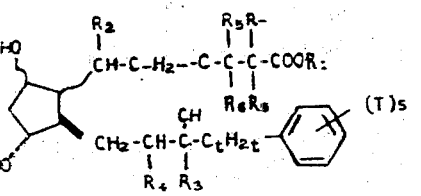 XXVI

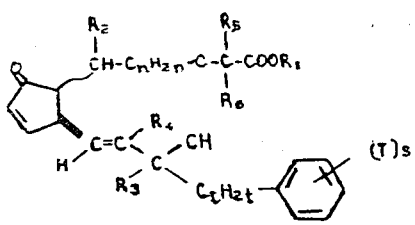 XXVII
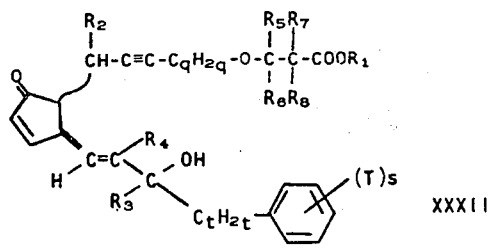 XXXII
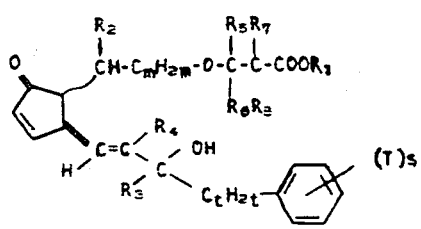 XXVIII
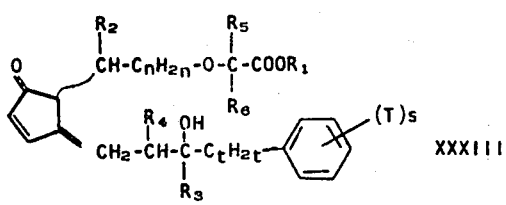 XXXIII
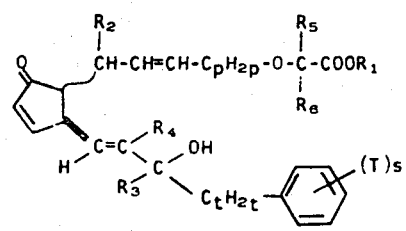 XXIX
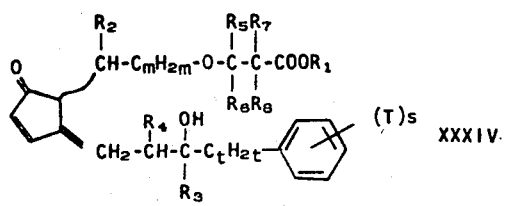 XXXIV
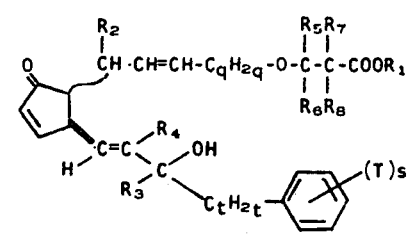 XXX
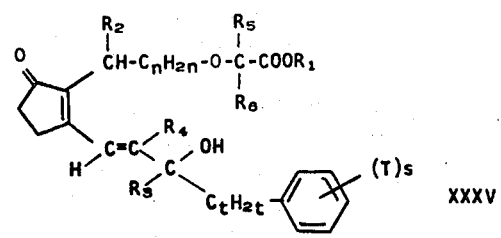 XXXV
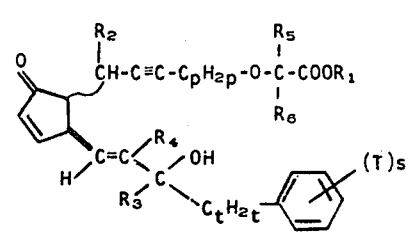 XXXI
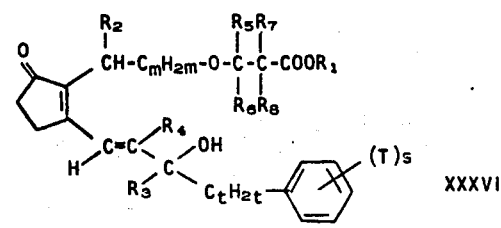 XXXVI

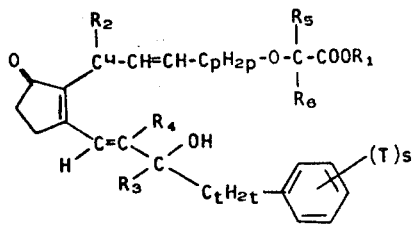

XXXVII

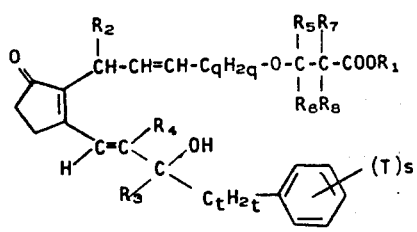

XXXVIII

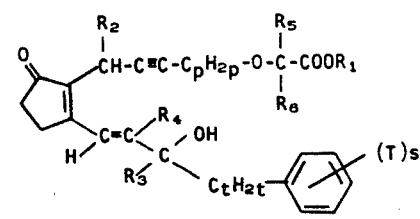

XXXIX

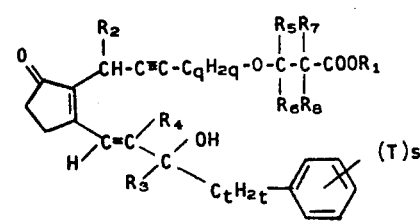

XL

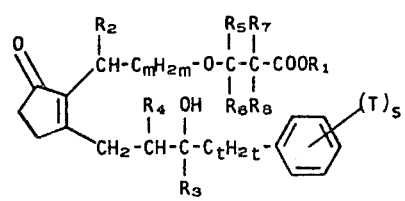

XLII

Formulas XI to XVIII represent 3-oxa and 4-oxa phenyl-substituted compounds of the PGE type. Formulas XIX to XXVI represent 3-oxa and 4-oxa phenyl-substituted compound of the PGF type. Formulas XXVII to XXXIV represent 3-oxa and 4-oxa phenyl-substituted compounds of the PGA type. Formulas XXXV to XLII represent 3-oxa and 4-oxa phenyl-substituted compounds of the PGB type.

In formulas XI to XLII, $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the $\beta$-position with 3 chloro, 2 or 3 bromo, or 1, 2, or 3 iodo. $R_2$, $R_3$, $R_4$, $R_5$, $R_6$, $R_7$, and $R_8$ are hydrogen or alkyl of one to 4 carbon atoms, inclusive. The divalent moiety $-C_nH_{2n}-$ represents alkylene of one to 10 carbon atoms, inclusive, with one to 5 carbon atoms, inclusive, between $-CHR_2-$ and $-O-$. The divalent moiety $-C_mH_{2m}-$ represents alkylene of 1 to 9 carbon atoms, inclusive, with 1 to 4 carbon atoms, inclusive, between $-CHR_2-$ and $-O-$. The divalent moiety $-C_pH_{2p}-$ represents alkylene of one to 8 carbon atoms, inclusive, with one, 2, or 3 carbon atoms between $-CH=CH-$ or $-C\equiv C-$ and $-O-$. The divalent moiety $-C_qH_{2q}-$ represents alkylene of one to 7 carbon atoms, inclusive, with 1 or 2 carbon atoms between $-CH=CH-$ or $-C\equiv C-$ and $-O-$. The moiety $-C_tH_{2t}-$ represents a valence bond, i.e., wherein t is zero, or alkylene of one to 10 carbon atoms, inclusive, i.e., wherein $t$ is one to 10, substituted with zero, one, or 2 fluoro, with one to 7 carbon atoms, inclusive, between $-CR_3OH-$ and the ring. When one or 2 fluoro are present as substituents of $-C_tH_{2t}-$, that moiety will contain 2t-1 or 2t-2 hydrogen atoms, respectively, rather than 2t hydrogen atoms. The symbol T represents alkyl of one to 4 carbon atoms, inclusive, fluoro, chloro, trifluoromethyl, or $-OR_9$, wherein $R_9$ is hydrogen, alkyl of one to 4 carbon atoms inclusive, or tetrahydropyranyl. The symbol s represents zero, one, 2 or 3. Regarding the combination $(T)_s$ attached to the phenyl ring, no more than two T are other than alkyl. Except for that proviso, when two or three T are present as substituents, they are the same or different.

The wavy line ~ in formulas XI to XXXIV indicates attachment of the group to the ring in alpha or beta configuration. In the case of the compounds of formulas XIX to XXVI, there are two wavy lines, and those formulas encompass compounds wherein the configurations of the hydroxy and the carboxyl-terminated moieties are, respectively, $\alpha,\alpha$, $\alpha,\beta$, $\beta,\alpha$, and $\beta,\beta$.

Formulas XI to XLII include lower alkanoates, and also pharmacologically acceptable salts when $R_1$ is hydrogen.

Also included in Formulas XI to XLII are separate isomers wherein the side chain hydroxy is in S or R (epi) configuration.

Included in Formulas XIII, XIV, XXI, XXII, XXIX, XXX, XXXVII, and XXXVIII are both the cis and the trans compounds with respect to the carbon-carbon double bond in the carboxy-terminated side chain. In all of the compounds containing —CH=CR$_4$—, that carbon-carbon double bond is in trans configuration, and the chain containing R$_4$ is attached to the cyclopentane ring in beta configuration in compounds encompassed by Formulas XI to XXXIV.

The novel 3-oxa and 4-oxa phenyl-substituted prostaglandin analogs of this invention include racemic compounds and both optically active enantiomeric forms thereof. As discussed hereinabove, two structural formulas are required to define accurately these racemic compounds. For convenience, only a single structural formula is used, for example, Formulas XI to XLII, to define the racemic form and both enantiomeric forms of each group of novel prostaglandin analogs. Each formula is, however, to be construed as including said racemic forms and both of said optically active enantiomeric forms.

Formula XI represents 3-oxa-17-phenyl-18,19,20-trinorPGE$_1$ (Formula IX hereinabove) when R$_1$, R$_2$, R$_3$, R$_4$, R$_5$, and R$_6$ and each hydrogen, C$_n$H$_{2n}$ is trimethylene ($n$ is 3), C$_t$H$_{2t}$ is ethylene ($t$ is 2), s is zero, the carboxyl-terminated side chain is attached to the cyclopentane ring in alpha configuration, and the configuration of the side chain hydroxy is S.

With regard to Formulas XI to XLII, examples of alkyl of one to 4 carbon atoms, inclusive, are methyl, ethyl, propyl, butyl, and isomeric forms thereof. Examples of alkyl of one to 8 carbon atoms, inclusive, are those given above, and pentyl, hexyl, heptyl, octyl, and isomeric forms thereof. Examples of alkyl of one to 10 carbon atoms, inclusive, are those given above, and nonyl, decyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkylene within the scope of —C$_n$H$_{2n}$—, —C$_m$H$_{2m}$—, —C$_p$H$_{2p}$—, and —C$_q$H$_{2q}$— as defined above, are methylene, ethylene, trimethylene, tetramethylene, pentamethylene, and those alkylene with one or more alkyl substituents on one or more carbon atoms thereof, e.g., —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_2$—, —CH$_2$—CH$_2$—CH(CH$_2$CH$_3$)—, and the like.

Examples of alkylene within the scope of —C$_t$H$_{2t}$— as defined above are those mentioned above, and also hexamethylene and heptamethylene, those with one or more alkyl substituents on one or more carbon atoms thereof, e.g., —CH$_2$—CH$_2$—CH$_2$—CH$_2$—CH$_2$CH(CH$_3$)—, and —CH(CH$_3$)—CH$_2$—CH$_2$—CH$_2$—CH$_2$—CH$_2$—C(CH$_3$)$_2$—, and also alkylene substituted with one or 2 fluoro, e.g., —CH$_2$—CHF—CH$_2$—, —CHF—CH$_2$—, —CHF—CHF—, —CHF—CH$_2$—CH$_2$—CH(CH$_3$)—, and —CHF—CH$_2$—CH(CH$_2$CH$_2$CH$_3$)—CH$_2$—CH$_2$—.

Examples of

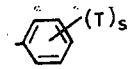

as defined above are phenyl, p-tolyl, m-tolyl, o-tolyl, p-fluorophenyl, m-fluorophenyl, o-fluorophenyl, p-chlorophenyl, m-chlorophenyl, o-chlorophenyl, p-trifluoromethylphenyl, m-trifluoromethylphenyl, o-trifluoromethylphenyl, p-hydroxyphenyl, m-hydroxyphenyl, o-hydroxyphenyl, p-methoxyphenyl, m-methoxyphenyl, o-methoxyphenyl, p-tetrahydropyranyloxyphenyl, m-tetrahydropyranyloxyphenyl, o-tetrahydropyranloxyphenyl o-ethylphenyl, m-isopropylphenyl, p-tert-butylphenyl, p-butoxyphenyl, 3,4-dimethylphenyl, 2,4-diethylphenyl, 2,4,6-trimethylphenyl, 3,4,5-trimethylphenyl, 2,4-dichlorophenyl, 3,4-difluorophenyl, 2-chloro-4-methylphenyl, 2-fluoro-4-methoxyphenyl, 3,5-dimethyl-4-fluorophenyl, 2,6-dimethyl-4-hydroxyphenyl, and 2,4-di(trifluoromethyl)phenyl.

PGE$_1$, PGE$_2$, dihydro-PGE$_1$, and the corresponding PGF$\alpha$, PGF$\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, PGF$\beta$, and PGA compounds as measured, for example, in anesthetized (pentobarbital sodium)pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE and PGA compounds are useful in mammals, including man and certain useful animals, e.g., dogs and pigs to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$ and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection of infusion during puerperium in the range 0.01 to 2 mg. per kg. of body weight per day, the exact dose depending on the age, weight, and condition of the patient or animal.

The PGE, PGA, and PGF$_\beta$ compounds are useful as hypotensive agents to reduce blood pressure in mammals, including man. For this purpose, the compounds are administered by intravenous infusion at the rate about 0.01 to about 50 μg. per kg. of body weight per minute, or in single or multiple doses of about 25 to 500 μg. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGF$_{2\alpha}$, for example, is administered systemically at a dose level in the range 0.01 mg. to about 20 mg. per kg. of body weight of the female mammmal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephric states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg./ml of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitro urazone, and with corticoid steriods, for example, hydrocortisone, prednisolone, methylprednisolone, and fluprednisolone, each of those being used in the combination at the usual concentration suitable for its use alone.

The novel Formula XI-to-XVIII 3-oxa and 4-oxa phenylsubstituted PGE-type compounds, the novel Formula XIX-to-XXVI 3-oxa and 4-oxa phenyl-substituted $PGF_\alpha$ - and $PGF_\beta$ -type compounds, the novel Formula XXVII-to-XXXIV 3-oxa and 4-oxa phenyl-substituted PGA-type compounds, and the novel Formula XXXV-to-XLII 3-oxa and 4-oxa phenyl-substituted PGS-type compounds each cause the biological responses described above for the PGE, $PGF_\alpha$, $PGF_\beta$, PGA, and PGB compounds, respectively, and each of these novel compounds is accordingly useful for the above-described corresponding purposes, and is used for those purposes in the same manner as described above.

The known PGE, $PGF_\alpha$, $PGF_\beta$, PGA, and PGB compounds are all potent in causing multiple biological responses even at low doses. For example, $PGE_1$ and $PGE_2$ are extremely potent in causing vasodepression and smooth muscle stimulation, and also are potent as antilipolytic agents. However, for many applications, these known prostaglandins have an inconveniently short duration of biological activity. In striking contrast, the novel prostaglandin analogs of Formulas XI to XLII are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter. Use of the novel analog for that purpose results in smaller undesired side effects than when the known prostaglandin is used for the same purpose. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of Formulas XI to XLII are preferred. For example, it is preferred that the carboxy-terminated chain in each formula contain a chain of six atoms between the carboxy and the cyclopentane ring. One of those six atoms will be the oxa atom and the other five will be carbon atoms. Accordingly and with reference to Formulas XI to XLII, it is preferred that $-C_nH_{2n}-$ represent a 3-carbon divalent chain, that $-C_mH_{2m}-$ represent a 2-carbon divalent chain, and that $-C_pH_{2p}-$ represent a divalent carbon atom. These preferences do not exclude additional carbon atoms (alkyl groups) as branching.

A seven-atom carboxy-terminated chain is not included in the compounds of Formulas XIV, XVI, XXII, XXIV, XXX, XXXII, XXXVIII, XL, i.e., formulas wherein the carboxy-terminated side chain is 4-oxa and contains a carbon-carbon double or triple bond. In each of those compounds, the $q$ of $-C_qH_{2q}-$ is at least one; and at least seven atoms, one oxygen (oxa) and six carbons, are present between the carboxy and the cyclopentane ring. Preferably, $q$ is one.

Another preference for the compounds of Formulas XI to XLII is that $R_2$, $R_3$, $R_4$, $R_5$, $R_6$, $R_7$, and $R_8$ are hydrogen or methyl. All of those R groups can be hydrogen, all can be methyl, or there can be any of the possible combinations of hydrogen and methyl. It is especially preferred that $R_3$ be methyl.

Another preference for the compounds of Formulas XI to XLII is that $-C_tH_{2t}$ be a valence bond, i.e., $t$ is zero, or straight chain alkylene of one to 4 carbon atoms, i.e., $-(CH_2)_d-$ wherein $d$ is one, 2, 3, or 4, with or without a fluoro or alkyl substituent on the carbon adjacent to the hydroxy-substituted carbon (C-15 in $PGE_1$), e.g., $-CHF-(CH_2)_g-$, $-CH(CH_3)-(CH_2)_g-$, $-CH(C_2H_5)-(CH_2)_g-$, $-C(CH_3)_2-(CH_2)_g-$, $-C(C_2H_5)_2-(CH_2)_g-$, $-C(CH_3)(C_2H_5)-(CH_2)_g-$, where $g$ is zero, 1, 2, or 3. It is also preferred that the phenyl ring, when substituted, i.e., $s$ is not zero, be substituted at least at the para position.

Another advantage of the novel compounds of this invention, especially the preferred compounds defined hereinabove, compared with the known prostaglandins, is that these novel compounds are administered effectively orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 3-oxa and 4-oxa phenyl-substituted PGE, $PGF_\alpha$, $PGF_\beta$, PGA, and PGB type compounds encompassed by Formulas XI to XLII, including the special classes of compounds described above, are used for the purposes described above in the free acid form, in ester form, or in pharmacologically acceptable salt form. When the ester form is used, the ester is any of those within the above definition of $R_1$. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these Formula XI-to-XLII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like,
as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The 3-oxa and 4-oxa phenyl-substituted PGE, $PGF_\alpha$, $PGF_\beta$, PGA, and PGB type compounds encompassed by Formulas XI to XLII, including the special classes of compounds described above, are also used for the purposes described above in free hydroxy form or in the form wherein the hydroxy moieties are transformed to lower alkanoate moieties, e.g., $-OH$ to $-OCOCH_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of Formulas XI to XLII are administered in various ways for various purposes; e.g., intravenously, intramuscularly, subcutaneously, orally, intravaginally, rectally, buccally sublingually, topically, and in the form of sterile implants for prolonged action.

For intravenous injection or infusion, sterile aqueous isotonic solutions are preferred. For that purpose, it is preferred because of increased water solubility that $R_1$ in the Formula XI-to-XLII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

The 3-oxa and 4-oxa phenyl-substituted PGE, $PGF_\alpha$, $PGF_\beta$, PGA, and PGB compounds encompassed by Formulas XI to XLII are produced by the reactions and procedures described and exemplified hereinafter.

The various 3-oxa and 4-oxa phenyl-substituted $PGF_\alpha$-type and $PGF_\beta$-type compounds encompassed by Formulas XIX to XXVI are prepared by carbonyl reduction of the corresponding PGE-type compounds encompassed by Formulas XI to XVIII. For example, carbonyl reduction of 3-oxa-17-phenyl-18,19,20-trinor-$PGE_1$ gives a mixture of 3-oxa-17-phenyl-18,19,20-trinor-$PGF_{1\alpha}$ and 3-oxa-17-phenyl-18,19,20-trinor-$PGF_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta Chem. Scand. 16, 969 (1962), and British Specification No. 1,097,533. Any reducing agent is used which does not react with carboncarbon double bonds or ester groups. Preferred reagents are lithium (tri-tert-butoxy)aluminum hydride, the metal borohydrides, especially sodium, potassium, and zinc borohydrides, and the metal trialkoxy borohydrides, e.g., sodium trimethoxyborohydride or sodium triethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various 3-oxa and 4-oxa phenyl-substituted PGA-type compounds encompassed by Formulas XXVII to XXXIV are prepared by acidic dehydration of the corresponding PGE-type compounds encompassed by Formulas XI to XVIII. For example, acidic dehydration of 3-oxa-17-phenyl-18,19,20-trinor-PGE$_1$ gives 3-oxa-17-phenyl-18,19,20-trinor-PGA$_1$.

These acidic dehydrations are carried out by methods known in the art for acidic dehydrations of known prostanoic acid derivatives. See, for example, Pike et al., Proc. Nobel Symposium II, Stockholm (1966); Interscience Publishers, New York, pp. 162–163 (1967), and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may also cause partial hydrolysis of an ester reactant.

The various 3-oxa and 4-oxa phenyl-substituted PGB-type compounds encompassed by Formulas XXXV to XLII are prepared by basic dehydration of the corresponding PGE-type compounds encompassed by Formulas XI to XVIII, or by contacting the corresponding PGA-type compounds encompassed by Formulas XXVII to XXXIV with base. For example, both 3-oxa-17-phenyl-18,19,20-trinor-PGE$_1$ and 3-oxa-17-phenyl-18,19,20-trinor-PGA$_1$ give 3-oxa-17-phenyl-18,19,20-trinor-PGB$_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE type or PGA type compound is maintained in such a reaction medium until no further PGB type compound is formed, as shown by the characteristic ultraviolet light absorption near 278 m$\mu$ for the PGB type compound.

The various transformations of 3-oxa and 4-oxa phenyl-substituted PGE-type compounds of Formulas XI to XVIII to the corresponding 3-oxa and 4-oxa phenyl-substituted PGF$\alpha$, PGF$\beta$, PGA, and PGB type compounds are shown in Chart A, wherein R$_1$, R$_2$, R$_3$, and $\sim$ are as defined above, wherein E is —CH$_2$CHR$_4$— or trans —CH=CR$_4$—, wherein V is —C$_n$H$_{2n}$—O—CR$_5$R$_6$—, —C$_m$H$_{2m}$—O—CR$_5$R$_6$—CR$_7$R$_8$—, —CH=λCH—C$_p$H$_{2p}$—O—CR$_5$R$_6$— (cis or trans), —CH=λCH—C$_q$H$_{2q}$—O—CR$_5$R$_6$—CR$_7$R$_8$— (cis or trans), —C≡C—C$_p$H$_{2p}$—O—CR$_5$R$_6$—, or —C≡C—C$_q$H$_{2q}$—O—CR$_5$R$_6$—CR$_7$R$_8$—, wherein R$_4$, R$_5$, R$_6$, R$_7$, R$_8$, $n$, $m$, $p$, and $q$ are as defined above, with the proviso that V is —C$_n$H$_{2n}$—O—CR$_5$R$_6$— or —C$_m$H$_{2m}$—O—CR$_5$R$_6$—$_{CR_7}$R$_8$— when E is —CH$_2$—CHR$_4$—, and wherein Q is

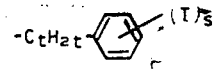

wherein C$_t$H$_{2t}$, T, and $s$ are as defined above.

The various 3-oxa and 4-oxa phenyl-substituted dihydro-PGE$_1$, dihydro-PGF$_{1\alpha}$, dihydro-PGF$_{1\beta}$, dihydro-PGA$_1$, and dihydro-PGB$_1$ type compounds encompassed by Formulas XVII, XVIII, XXV, XXVI, XXXIII, XXXIV, XLI, and XLII are prepared by carbon-carbon double bond reduction of the corresponding PGE, PGF$\alpha$, PGF$\beta$, PGA, and PGB type compound containing a trans double bond in the hydroxy-containing side chain. A cis or trans double bond or an acetylenic bond can also be present in the carboxy-terminated side chain of the unsaturated reactant, and will be reduced at the same time to —CH$_2$CH$_2$—. For example, 13,14-dihydro-3-oxa-17-phenyl-18,19,20-trinor-PGE$_1$ is produced by reduction of 3-oxa-17-phenyl-18,19,20-trinor-PGE$_1$, 3-oxa-17-phenyl-18,19,20-trinor-PGE$_2$, or 5,6-dehydro-3-oxa-17-phenyl-18,19,20-trinor-PGE$_2$.

These reductions are carried out by reacting the unsaturated PGE, PGF$\alpha$, PGF$\beta$, PGA, or PGB type compound with diimide, following the general procedure described by van Tamelen, et al., J. Am. Chem. Soc. 83, 3725, (1961).

CHART A

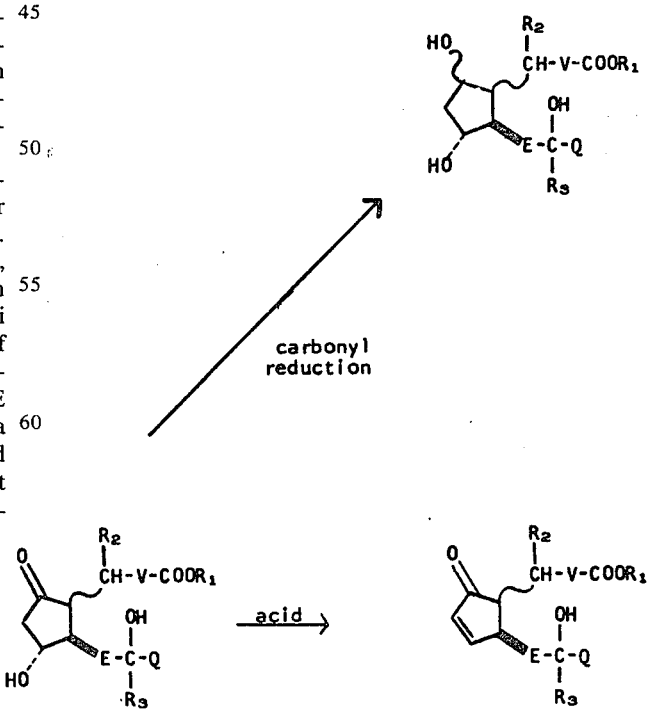

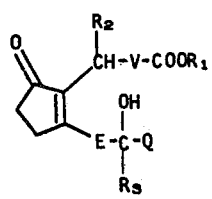

See also Fieser et al., "Topics in Organic Chemistry," Reinhold Publishing Corp., New York, pp. 432–434 (1963) and references cited therein. The unsaturated acid or ester reactant is mixed with a salt of azodiformic acid, preferably an alkali metal salt such as the disodium or dipotassium salt, in the presence of an inert diluent, preferably a lower alkanol such as methanol or ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein $R_1$ is hydrogen is used, the carboxylic acid reactant also serves to acidify an equivalent amount of the azodiformic acid salt. A reaction temperature in the range of about 10° to about 40° C. is usually suitable. Within that temperature range, the reaction is usually complete within less than 24 hours. The desired dihydro product is then isolated by conventional methods, for example, evaporation of the diluent, followed by separation from inorganic materials by solvent extraction.

In the case of the 3-oxa and 4-oxa phenyl-substituted unsaturated PGE, $PGF_\alpha$, and $PGF_\beta$ type reactants, the reductions to the corresponding 3-oxa and 4-oxa phenyl-substituted dihydro-$PGE_1$, dihydro-$PGF_{1\alpha}$, and dihydro-$PGF_{1\beta}$ compounds are also carried out by catalytic hydrogenation. For that purpose, palladium catalysts, especially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 10° to about 100° C. are preferred. The resulting dihydro product is isolated from the hydrogenation reaction mixture by conventional methods, for example, removal of the catalyst by filtration or centrifugation, followed by evaporation of the solvent.

Diimide reductions and catalytic hydrogenations to produce the various novel 3-oxa and 4-oxa phenyl-substituted dihydro compounds of this invention from the corresponding 3-oxa and 4-oxa $PGE_1$, $PGF_{1\alpha}$, $PGF_{1\beta}$, $PGA_1$, and $PGB_1$, type compounds are shown in Chart B, wherein $R_1$, $R_2$, $R_3$, $R_4$, Q, and $\sim$ are as defined above, and W is $-C_nH_{2n}-O-CR_5R_6-$ or $-C_mH_{2m}-O-CR_5R_6-CR_7R_8-$, wherein $n, m, R_5, R_6, R_7$, and $R_8$ are defined above.

Diimide reductions and catalytic hydrogenations to produce the same novel 3-oxa and 4-oxa phenyl-substituted dihydro compounds of this invention from the corresponding 3-oxa and 4-oxa phenyl-substituted $PGE_2$, $PGF_{2\alpha}$, $PGF_{2\beta}$, $PGA_2$, and $PGB_2$ type compounds and also from the corresponding compounds with a trans-ethylenic or an acetylenic linkage in place of the cis-ethylenic linkage in the carboxyl-terminated side chain, are shown in Chart C, wherein $R_1$, $R_2$, $R_3$, $R_4$, Q, and $\sim$ are as defined above, U is cis $-CH=CH-$, trans $-CH=CH-$, or $-C\equiv C-$, and Y is $-C_pH_{2p}-O-CR_5R_6-$ or $-C_qH_{2q}-O-CR_5R_6-CR_7R_8-$, wherein $p, q, R_5, R_6, R_7$, and $R_8$ are as defined above.

CHART B

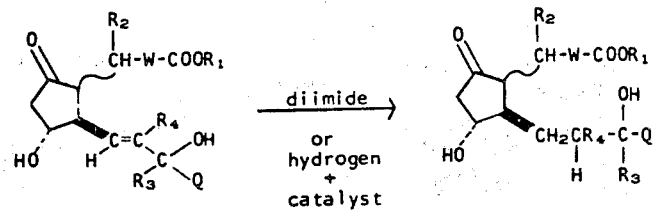

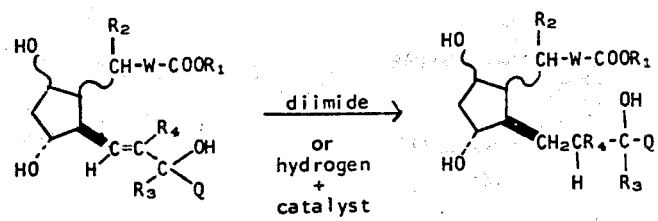

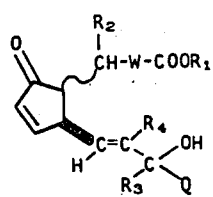 diimide → 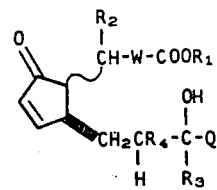
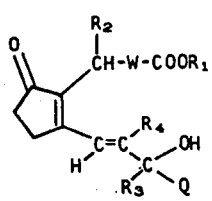 diimide → 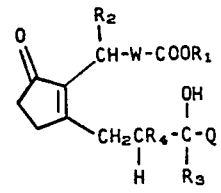
CHART C
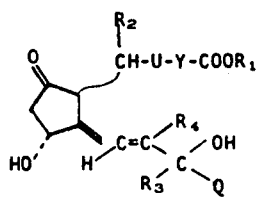 diimide or hydrogen + catalyst → 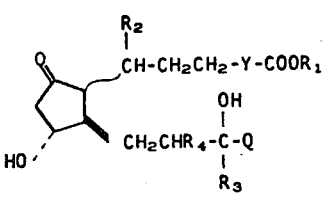
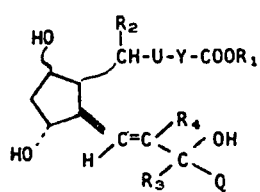 diimide or hydrogen + catalyst → 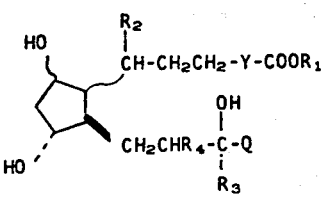
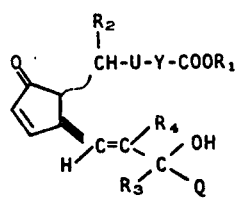 diimide → 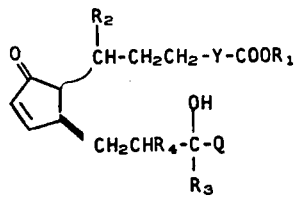
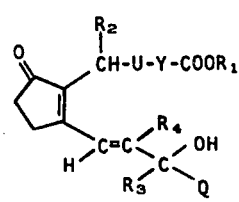 diimide → 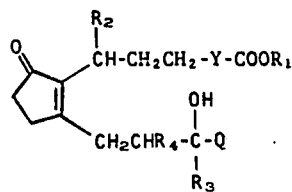

The 3-oxa and 4-oxa phenyl-substituted compounds of the PGE$_2$, PGF$_{2\alpha}$, PGF$_{2\beta}$, PGA$_2$, and PGB$_2$ type wherein the carbon-carbon double bond in the carboxy-terminated side chain is in cis configuration are prepared by reduction of the corresponding acetylenic 3-oxa and 4-oxa phenyl-substituted compounds, i.e., those with a carbon-carbon triple bond in place of said carbon-carbon double bond. For that purpose, there are used any of the known reducing agents which reduce an acetylenic linkage to a cis-ethylenic linkage. Especially preferred for that purpose are diimide, or hydrogen and a catalyst, for example, palladium (5%) on barium sulfate, especially in the presence of pyridine. See Fieser et al., "Reagents for Organic Synthesis," pp. 566–567, John Wiley & Sons, Inc., New York, N.Y. (1967). These reductions are shown in Chart D, wherein R$_1$, R$_2$, R$_3$, R$_4$, Q, Y, and ~ are as defined above. These 3-oxa and 4-oxa phenyl-substituted cis compounds of the PGE$_2$, PGF$_{2\alpha}$, PGF$_{2\beta}$, PGA$_2$, and PGB$_2$ type are also prepared as described hereinafter.

The 3-oxa and 4-oxa phenyl-substituted PGE type compounds of Formulas XI to XVI except wherein R$_1$ is hydrogen, and the 3-oxa and 4-oxa phenyl-substituted PGA type compounds of Formulas XXVII to XXXII except wherein R$_1$ is hydrogen are prepared by the series of reactions shown in Chart E, wherein Q, R$_2$, R$_3$, R$_4$, and V are as defined above; Q' is

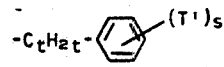

wherein T' is the same as T above except that R$_9$ is not hydrogen; R$_{10}$ is the same as the above definition of R$_1$ except that R$_{10}$ does not include hydrogen; R$_{11}$ and R$_{12}$ are alkyl of one to 4 carbon atoms, inclusive; R$_{13}$ is alkyl of one to 5 carbon atoms, inclusive; and ~ indicates attachment of —CHR$_2$—V—COOR$_{10}$ to the cyclopentane ring in alpha beta configuration, and exo or endo configuration with respect to the moiety attached to the cyclo-propane ring.

CHART D

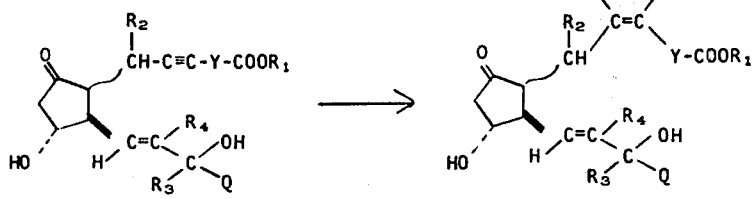

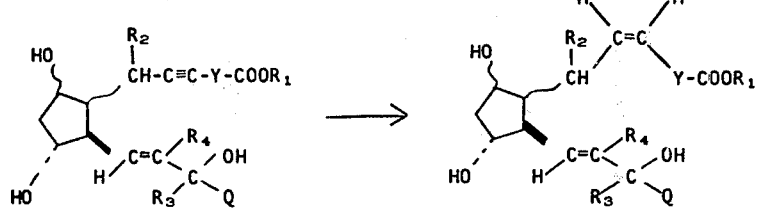

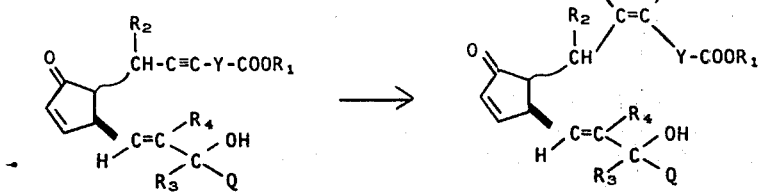

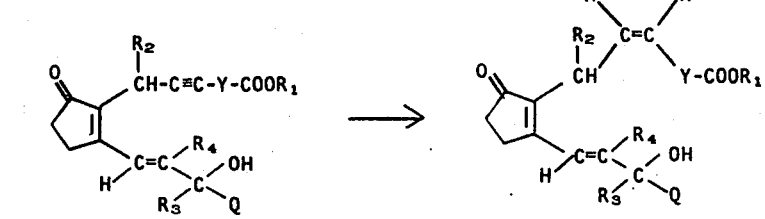

CHART E

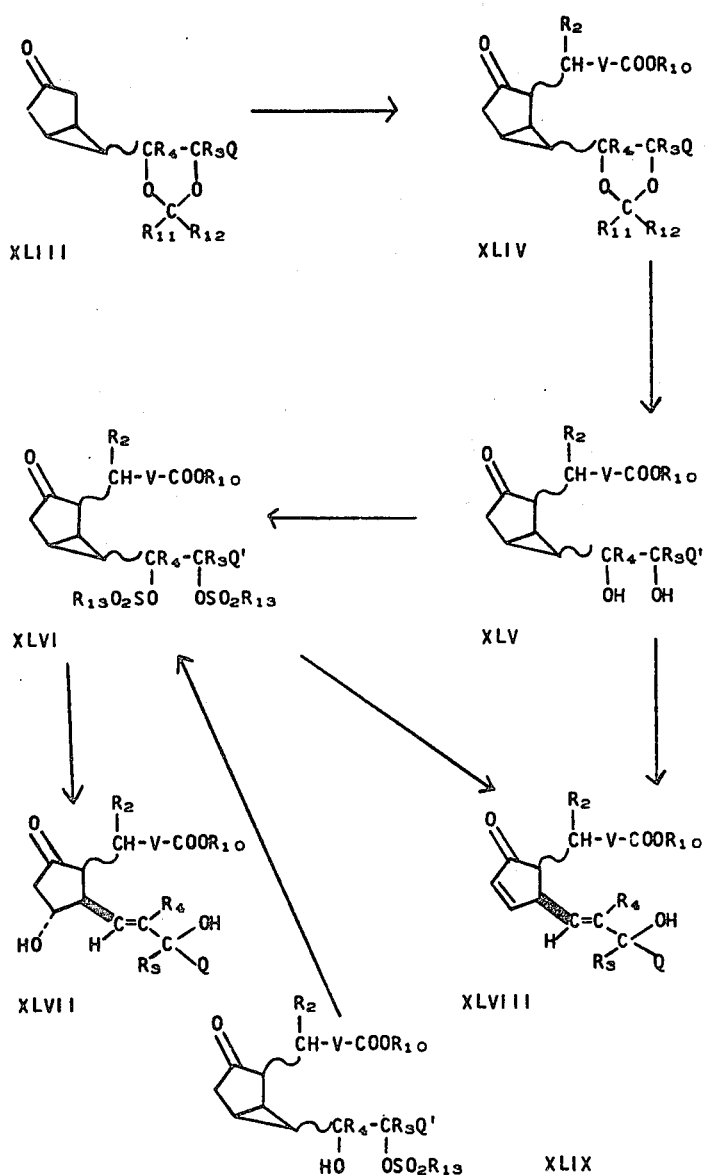

The 3-oxa and 4-oxa phenyl-substituted PGE$_1$ type compounds of Formulas XI and XII, the 3-oxa and 4-oxa phenyl-substituted 5,6-dehydro-PGE$_2$ type compounds of Formulas XV and XVI, the 3-oxa and 4-oxa phenyl-substituted PGA$_1$ type compounds of Formulas XXVII and XXVIII and the 3-oxa and 4-oxa phenyl-substituted 5,6-dehydro-PGA$_2$ type compounds of Formulas XXXI and XXXII are also prepared by the series of reactions shown in Chart F, wherein Q, R$_2$, R$_3$, R$_4$, R$_{10}$, and R$_{13}$, are as defined above; Q' is

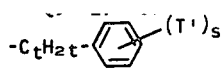

wherein T' is the same as T above except that R$_9$ is not hydrogen; Z is $-C_nH_{2n}-O-CR_5R_6-$, $-C_mH_{2m}-O-CR_5R_6-CR_7R_8-$, $-C\equiv C-C_pH_{2p}-O-CR_5R_6-$, or $-C\equiv C-C_qH_{2q}-O-CR_5R_6-CR_7R_8-$; and ~ indicates attachment of $-CH-R_2-Z-COOR_{10}$ to the cyclopentane ring in alpha or beta configuration, and exo or endo configuration with respect to the moiety attached to the cyclopropane ring.

It should be observed regarding the series of reactions shown in Charts E and F, that the reactions starting with glycol XLV in Chart E are similar to the reactions starting with glycol LII in Chart F. The only differences here are the definitions of the divalent moieties V (Chart E) and Z (Chart F). V includes saturated, cis and trans ethylenic, and acetylenic divalent moieties. Z is limited to the saturated and acetylenic divalent moieties encompassed by V. In other words, final 3-oxa and 4-oxa phenyl-substituted PGE type compounds of Formula XLVII (Chart E) encompass compounds of Formulas XI to XVI.

CHART F

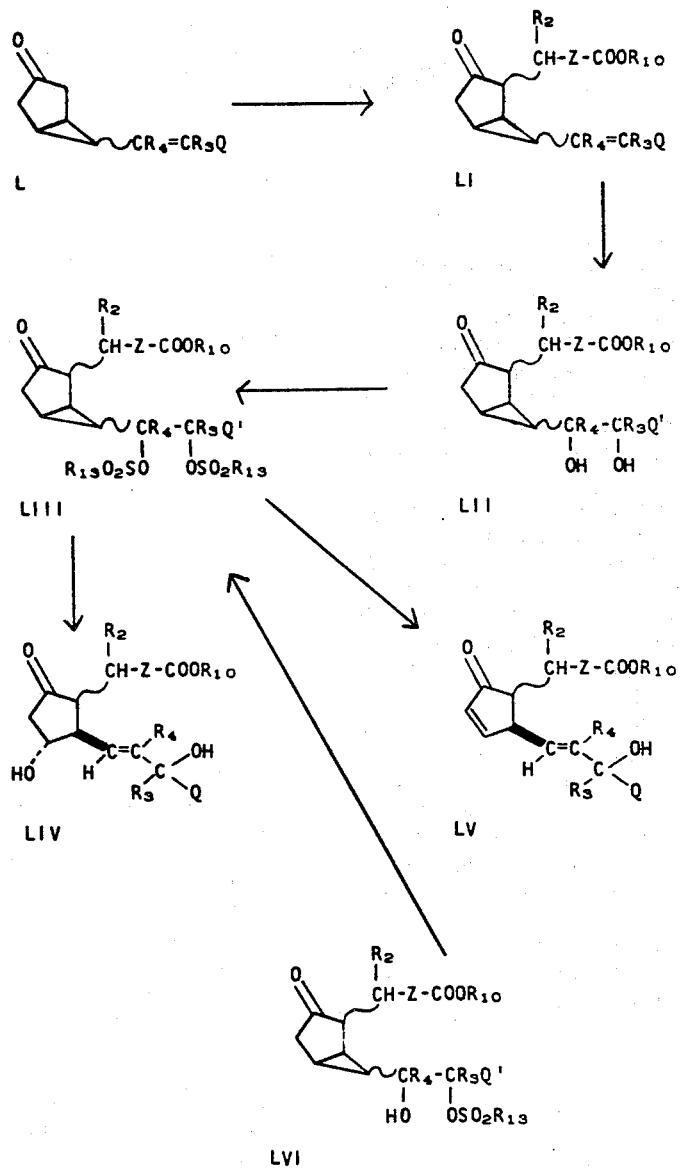

Final 3-oxa and 4-oxa phenyl-substituted PGA type compounds of Formula XLVIII (Chart E) encompass compounds of Formulas XXVII to XXXII. On the other hand, final 3-oxa and 4-oxa phenyl-substituted PGE type compounds of Formula LIV (Chart F) encompass only compounds of Formulas XI, XII, XV, and XVI, and final 3-oxa and 4-oxa phenyl-substituted PGA type compounds of Formula LV (Chart F) encompass only compounds of Formulas XXVII, XXVIII, XXXI, and XXXII.

As will subsequently appear, an acetylenic intermediate of Formulas XLIV, XLV, or LII is transformed by stepwise reduction to the corresponding cis or trans ethylenic intermediates of Formulas XLIV or XLV; and an acetylenic intermediate of Formulas XLIV, XLV, or LII, or a cis or trans ethylenic intermediate of Formulas XLIV or XLV is transformed by reduction to the corresponding saturated intermediate of Formulas XLIV, XLV, or LII.

The initial bicyclo-ketone reactant of Formula L in Chart F is also used as an initial reactant to produce the initial bicyclo-ketone cyclic ketal reactant of Formula XLIII in Chart E. The following reactions will produce cyclic ketal XLIII, wherein THP is tetrahydropyranyl, and O is phenyl:

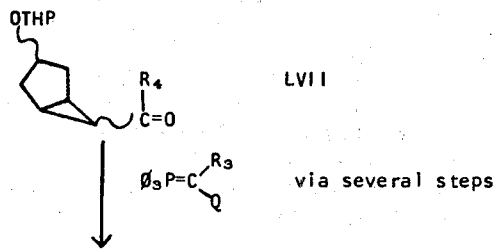

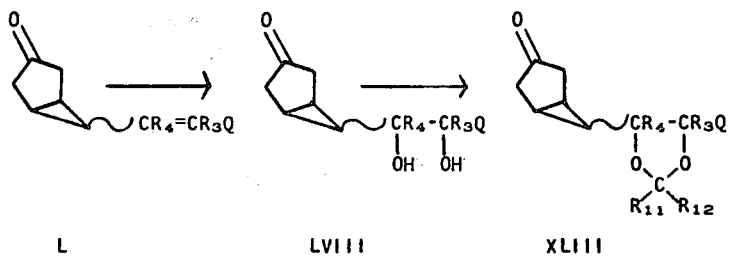

L  LVIII  XLIII

The initial bicyclo-ketone reactant of Formula L exists in four isomeric forms, exo and endo with respect to the attachment of the —CR$_4$=CR$_3$Q moiety, and cis and trans with respect to the double bond in that same moiety. Each of those isomers separately or various mixtures thereof are used as reactants according to this invention to produce substantially the same final 3-oxa and 4-oxa phenyl-substituted PGE or PGA type product mixture.

The process for preparing either the exo or endo configuration of the Formula-L bicyclo-ketone is known to the art. See Belgian patent No. 702,477; reprinted in Farmdoc Complete Specifications, Book 714, No. 30,905, page 313, March 12, 1968. See West Germany Offenlegungsschrift No. 1,937,912; reprinted in Farmdoc Complete Specifications, Book No. 14, No. 6869 R, Weed R$_5$, March 18, 1970.

In said Belgian Pat. No. 702,477, a reaction sequence capable of forming exo ketone L is as follows: The hydroxy of 3-cyclopentenol is protected, for example, with a tetrahydropyranyl group. Then a diazoacetic acid ester is added to the double bond to give an exo-endo mixture of a bicyclo-[3.1.0]hexane substituted at 3 with the protected hydroxy and at 6 with an esterified carboxyl. The exo-endo mixture is treated with a base to isomerize the endo isomer in the mixture to more of the exo isomer. Next, the carboxylate ester group at 6 is transformed to an aldehyde group or ketone group, —CHO or

—C=O, wherein R$_4$ is as defined above. Then, said aldehyde group or said keto group is transformed by the Wittig reaction, in this case to a moiety of the formula —CR$_4$=CR$_3$Q which is in exo configuration relative to the bicyclo ring structure. Next, the protective group is removed to regenerate the 3-hydroxy which is tne oxidized, for example, by the Jones reagent, i.e. chromic acid (see J. Chem. Soc. 39 (1946)), to give said exo ketone L.

Separation of the cis-exo and trans-exo isomers of L is described in said Belgian Pat. No. 702,477. However, as mentioned above, that separation is usually not necessary since the cis-trans mixture is useful as a reactant in the next process step.

The process described in said Belgian Pat. No. 702,477 for producing the exo form of bicyclo-ketone L uses, as an intermediate, the exo form of a bicyclo[3.1.0]hexane substituted at 3 with a protected hydroxy, e.g., tetrahydropyranyloxy, and at 6 with an esterified carboxyl. When the corresponding endo compound is substituted for that exo intermediate, the process in said Offenlegungsschrift No. 1,937,912 leads to the endo form of bicyclo-ketone L. That endo compound to be used has the formula:

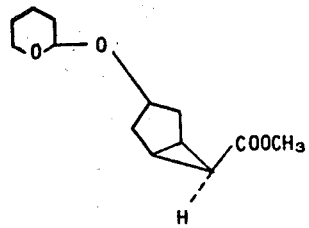

LIX

Compound LIX is prepared by reacting endo-bicyclo[3.1.0]-hex-2-ene-6-carboxylic acid methyl ester with diborane in a mixture of tetrahydrofuran and diethyl ether, a reaction generally known in the art, to give endo-bicyclo[3.1.0]-hexan-3-ol-6-carboxylic acid methyl ester which is then reacted with dihydropyran in the presence of a catalytic amount of POCl$_3$ to give the desired compound. This is then used as described in said Offenlegungsschrift NO. 1,937,912 to produce the endo form of bicyclo-ketone L.

As for exo L, the above process produces a mixture of endo-cis and endo-trans compounds. These are separated as described for the separation of exo-cis and exo-trans L, but this separation is usually not necessary since, as mentioned above, the cis-trans mixture is useful as a reactant in the next process step.

In the process of said Belgian patent and said Offenlegungsschrift, certain organic halides, e.g., chlorides and bromides, are necessary to prepare the Wittig reagents used to generate the generic moiety —CR$_4$=CR$_3$Q of bicyclo-ketone L. These organic chlorides and bromides

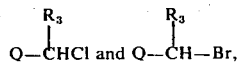

are known in the art or can be prepared by methods known in the art.

To illustrate the availability of these organic chlorides and bromides, consider the above-described 3-oxa and 4-oxa phenyl-substituted PGE type compounds of Formulas XI to XVIII, wherein C$_t$H$_{2t}$ represents a valence bond or alkylene of one to 10 carbon atoms, inclusive, substituted with zero, one, or 2 fluoro, with one to 7 carbon atoms, inclusive, between —CR$_3$OH— and the phenyl ring; wherein T is alkyl of one to 4 carbon atoms, inclusive, fluoro, chloro, trifluoromethyl, or —$OR_9$, wherein $R_9$ is hydrogen, alkyl of one to 4 carbon atoms, inclusive, or tetrahydropyranyl, and s is 0, 1, 2, or 3, with the proviso that not more than two T are other than alkyl; and wherein $R_3$ is hydrogen or alkyl of one of 4 carbon atoms, inclusive. The halides necessary to prepare those compounds, if not readily available, are advantageously prepared by reacting the corresponding primary alcohol,

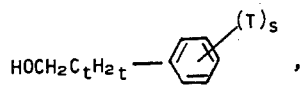

or secondary alcohol

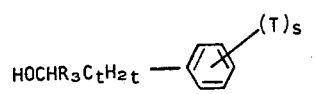

with $PCL_3$, $HBr_3$, HBr, or any of the other halogenating agents known in the art to be useful for this purpose.

In the case of $R_3$ being H, some of the readily available halides are shown in Table I wherein s, T, and t of the formula for the intermediate halides are as defined above, and Hal is chloro, bromo, or iodo. Thus, compound No. 1 of Table I is represented by the formula wherein S and t are zero, and Hal is chloro, i.e.

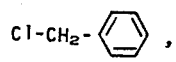

namely α-chlorotoluene or benzyl chloride; compound No. 8 of Table I is represented by the formula wherein s is zero, t is 2, and Hal is bromo, i.e.

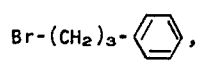

namely 1-bromo-3-phenylpropane or 3-bromopropylbenzene; and compound No. 63 of Table 1 represented by the formula wherein s is 3, T is methyl in the 2-, 4- and 5- positions with respect to the $C_tH_{2t}$ substitution, t is 2, and Hal is bromo, i.e.,

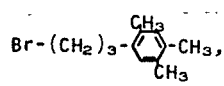

namely 1-(3-bromophenyl)-2,4,5-trimethylbenzene.

TABLE I

Intermediate Halides represented by the formula

Hal—$CH_2$—$C_tH_{2t}$—⟨⟩—$(T)_s$

| No. | s | T | t | Hal |
|---|---|---|---|---|
| 1 | 0 | — | 0 | Cl |
| 2 | 0 | — | 0 | Br |
| 3 | 0 | — | 0 | I |
| 4 | 0 | — | 1 | Cl |
| 5 | 0 | — | 1 | Br |
| 6 | 0 | — | 1 | I |
| 7 | 0 | — | 2 | Cl |
| 8 | 0 | — | 2 | Br |
| 9 | 0 | — | 2 | I |
| 10 | 0 | — | 3 | Cl |
| 11 | 0 | — | 3* | Cl |
| 12 | 0 | — | 3 | Br |
| 13 | 0 | — | 4 | Cl |
| 14 | 1 | 2-$CH_3$ | 0 | Cl |
| 15 | 1 | 2-$C_2H_5$ | 0 | Cl |
| 16 | 1 | 4-$C_2H_5$ | 0 | Cl |
| 17 | 1 | 2-$CF_3$ | 0 | Cl |
| 18 | 1 | 4-$OCH_3$ | 0 | Cl |

TABLE I-continued

Intermediate Halides represented by the formula

Hal—$CH_2$—$C_tH_{2t}$—⟨⟩—$(T)_s$

| No. | s | T | t | Hal |
|---|---|---|---|---|
| 19 | 1 | 3-$CH_3$ | 0 | Br |
| 20 | 1 | 4-$CH_3$ | 0 | Br |
| 21 | 1 | C-$C_5H_{11}$ | 0 | Br |
| 22 | 1 | 4-Cl | 0 | Br |
| 23 | 1 | 2-$CF_3$ | 0 | Br |
| 24 | 1 | 3-$CF_3$ | 0 | Br |
| 25 | 1 | 4-$CH_3$ | 0 | I |
| 26 | 1 | 4-F | 1 | Cl |
| 27 | 1 | 3-Cl | 1 | Br |
| 28 | 1 | 4-Cl | 1 | Br |
| 29 | 1 | 4-F | 1 | Br |
| 30 | 1 | 2-Cl | 2 | Br |
| 31 | 1 | 3-Cl | 2 | Br |
| 32 | 1 | 4-Cl | 2 | Br |
| 33 | 1 | 4-F | 3* | Br |
| 34 | 1 | 2-Cl | 4 | Br |
| 35 | 2 | 2-$CH_3$, 4-$CH_3$ | 0 | Cl |
| 36 | 2 | 2-$CH_3$, 5-$CH_3$ | 0 | Cl |
| 37 | 2 | 2-$CH_3$, 6-$CH_3$ | 0 | Cl |
| 38 | 2 | 3-$CH_2$, 4-$CH_3$ | 0 | Cl |
| 39 | 2 | 2-$CH_3$, 4-Cl | 0 | Cl |
| 40 | 2 | 2-$CH_3$, 5-$CH_3$ | 0 | Br |
| 41 | 2 | 2-$CH_3$, 6-$CH_3$ | 0 | Br |
| 42 | 2 | 3-$CH_3$, 5-t-butyl | 0 | Br |
| 43 | 2 | 3-$CH_3$, 4-Cl | 0 | Br |
| 44 | 2 | 2-$CH_3$, 3-Br | 0 | Br |
| 45 | 2 | 3-$OCH_3$, 4-$OCH_3$ | 0 | Cl |
| 46 | 2 | 3-$OCH_3$, 5-$OCH_3$ | 0 | Cl |
| 47 | 2 | 3-$OCH_3$, 5-$OCH_3$ | 0 | Br |
| 48 | 2 | 2-$CH_3$, 4-$CH_3$ | 1 | Cl |
| 49 | 2 | 2-$CH_3$, 4-$CH_3$ | 1 | Br |
| 50 | 2 | 3-$CH_3$, 4-$CH_3$ | 1 | Br |
| 51 | 2 | 3-$OCH_3$, 4-$OCH_3$ | 1 | Br |
| 52 | 2 | 3-$OCH_3$, 5-$OCH_3$ | 1 | Br |
| 53 | 2 | 3-$OCH_3$, 4-$OCH_3$ | 1 | I |
| 54 | 2 | 3-$OCH_3$, 4-$OCH_3$ | 2 | Br |
| 55 | 2 | 3-$OCH_3$, 5-$OCH_3$ | 2 | Br |
| 56 | 2 | 3-$OCH_3$, 5-$OCH_3$ | 4 | Br |
| 57 | 3 | 2-$CH_3$, 4-$CH_3$, 5-$CH_3$ | 0 | Cl |
| 58 | 3 | 2-$CH_3$, 4-$CH_3$, 6-$CH_3$ | 0 | Cl |
| 59 | 3 | 4-$CH_3$, 2-$OCH_3$, 5-$OCH_3$ | 0 | Cl |
| 60 | 3 | 2-$CH_3$, 3-$CH_3$, 6-$CH_3$ | 0 | Br |
| 61 | 3 | 2-$CH_3$, 4-$CH_3$, 6-$CH_3$ | 0 | Br |
| 62 | 3 | 2-$CH_3$, 3-$OCH_3$, 6-$OCH_3$ | 0 | Br |
| 63 | 3 | 2-$CH_3$, 4-$CH_3$, 5-$CH_3$ | 2 | Br |

*-branched —CH—
              |
              Et

In the case of R₃ being alkyl, some of the readily available halides are shown in Table II. Thus, compound No. 1 of Table II is represented by the formula wherein s and t are zero, R₃ is methyl, and Hal is chloro, i.e.

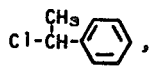

namely (1-chloroethyl)benzene; and compound No, 13 of Table II is represented by the formula wherein s is 2, t is one, R₃ and T are methyl, and Hal is bromo, i.e.

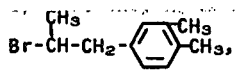

namely 4-(2-bromopropyl)-o-xylene or 1-(2-bromopropyl)-3-methyl-4-methylbenzene.

TABLE II

Intermediate Halides represented by the Formula

Hal—CH—C$_t$H$_{2t}$—⟨⟩—(T)$_s$
       |
       R₃

| No. | s | T | R₃ | t | Hal |
|-----|---|---|-----|---|-----|
| 1 | 0 | — | CH₃ | 0 | Cl |
| 2 | 0 | — | C₂H₅ | 0 | Cl |
| 3 | 0 | — | C₂H₅ | 0 | Br |
| 4 | 0 | — | CH₃ | 0 | I |
| 5 | 0 | — | CH₃ | 1 | Cl |
| 6 | 0 | — | n-C₃H₇ | 1 | Cl |
| 7 | 0 | — | CH₃ | 1 | Br |
| 8 | 0 | — | C₂H₅ | 2 | Cl |
| 9 | 1 | 4-C₂H₅ | CH₃ | 0 | Cl |
| 10 | 1 | 4-F | CH₃ | 0 | Cl |
| 11 | 1 | 4-Cl | C₂H₅ | 0 | Br |
| 12 | 1 | 4-F | C₂H₅ | O | Br |
| 13 | 2 | {3-CH₃, 4-CH₃} | CH₃ | 1 | Br |
| 14 | 2 | {3-OCH₃, 4-OCH₃} | CH₃ | 1 | Br |
| 15 | 2 | {2-OCH₃, 6-OCH₃} | CH₃ | 1 | Br |

Other intermediate halides of the general formula

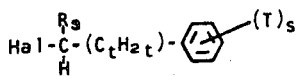

may be obtained from the primary or secondary alcohols as discussed above. These alcohols are in general prepared from corresponding carboxylic acids. Thus, the substituted benzoic acids are selectively reduced to the corresponding benzyl alcohols using any of several hydride reagents, e.g. sodium borohydride/aluminum chloride in diglyme, diborane in tetrahydrofuran, aluminum hydride in tetrahydrofuran, and the like. The secondary alcohols, wherein R₃ is alkyl, are prepared by transforming the COOH of the corresponding carboxylic acid,

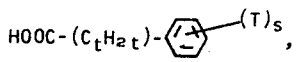

to a ketone by known procedures, e.g. by way of the acyl chloride and a dialkylcadmium. Reduction of the ketone with sodium borohydride then yields the secondary alcohol,

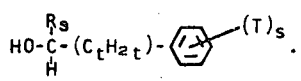

Hydroxyl groups on the aromatic ring are suitably protected during these reactions by first forming the corresponding tetrahydropyranyl ethers with dihydropyran; the hydroxyl groups are restored by mild acid hydrolysis as is well known in the art.

In the case of C$_t$H$_{2t}$ substituted with one or 2 fluoro atoms, there are a number of routes to the intermediate halides. The corresponding alcohols, for example β-fluorophenethyl alcohol, β-fluoro-α-methyl-phenethyl alcohol, β-fluoro- α,β-dimethyl-phenethyl alcohol, and the like, are reacted with PCl₃, PBr or HBr to form the halide. Alternatively, the carboxylic acid having one less carbon atoms in the chain than the desired intermediate halide, i.e.

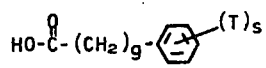

where g is t-1, is converted by a series of known methods to the 2,2-difluorohalide. Thus, the free carboxyl group is transformed first to the acid chloride with thionyl chloride and thence by way of the nitrile to the α-keto-acid. The carboxyl group is reduced to the alcohol with diborane and then converted to the α-keto halide. Finally, by reaction of the keto group with sulfur tetrafluoride, there is obtained

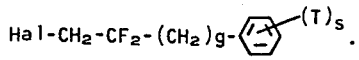

For reactions of SF₄ see U.S. Pat. No. 3,211,723 and J. Org. Chem. 27, 3164 (1962).

As mentioned above, Formula XI-to-XLII compounds with an alpha-fluoro substituent on the carbon adjacent to the hydroxy-substituted carbon (i.e. adjacent to C-15 in PGE₁) represent preferred embodiments among the novel phenyl-substituted compounds of this invention. The Formula-L bicycloketones necessary to produce those mono-fluoro compounds are advantageously prepared by reacting either of the abovementioned bicyclo-aldehydes, exo or endo, with a Wittig reagent prepared from

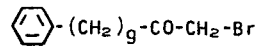

and triphenylphosphine. The aldehyde group is thereby transformed to

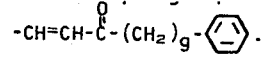

The resulting unsaturated ketone is reduced to the corresponding

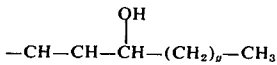

compound. Then -OH in that group is replaced with fluoro by known methods, for example, directly by reaction with 2-chloro-1,1,2-trifluorotriethylamine or indirectly for example, by transforming the hydroxy to tosyloxy or mesyloxy, and reacting the resulting compound with anhydrous potassium fluoride in diethylene glycol.

The transformation of bicyclo-ketone-olefin L to glycol LVIII is carried out by reacting olefin L with a hydroxylation reagent. Hydroxylation reagents and procedures for this purpose are known in the art. See, for example, Gunstone, Advances in Organic Chemistry, Vol. I, pp. 103–147, Interscience Publishers, New York, N.Y. (1960). Various isomeric glycols are obtained depending on such factors as whether olefin L is cis or trans and endo or exo, and whether a cis or a trans hydroxylation reagent is used. Thus endo-cis olefin L gives a mixture of two isomeric erythro glycols of Formula LVIII with a cis hydroxylation agent, e.g., osmium tetroxide. Similarly, the endo-trans olefin L gives a similar mixture of the same two erythro glycols with a trans hydroxylation agent, e.g., hydrogen peroxide. The endo-cis olefins and the endo-trans olefins L give similar mixtures of two threo glycol isomers with cis and trans hydroxylation reagents, respectively. These various glycol mixtures are separated into individual isomers by silica gel chromatography. However, this separation is usually not necessary, since each isomeric erythro glycol and each isomeric threo glycol is useful as an intermediate according to this invention and the processes outlined in Chart E to produce final products of Formulas XLVII and XLVIII, and then, according to Charts A, B, C, and D to produce the other final products of this invention. Thus, the various isomeric glycol mixtures encompassed by Formula LVIII produced from the various isomeric olefins encompassed by Formula L are all useful for these same purposes.

The transformation of glycol LVIII to the cyclic ketal of Formula XLIII (Chart E) is carried out by reacting said glycol with a dialkyl ketone of the formula

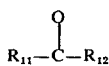

wherein $R_{11}$ and $R_{12}$ are alkyl of one to 4 carbon atoms, inclusive, in the presence of an acid catalyst, for example potassium bisulfate or 70% aqueous perchloric acid. A large excess of the ketone and the absence of water is desirable for this reaction. Examples of suitable dialkyl ketones are acetone, methyl ethyl ketone, diethyl ketone, methyl propyl ketone, and the like. Acetone is preferred as a reactant in this process.

Referring again to Chart E, cyclic ketal XLIII is transformed to cyclic ketal XLIV by alkylating with an alkylation agent of the formula

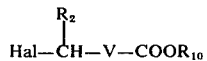

wherein $R_2$, $R_{10}$, and V are as defined above, and Hal is chlorine, bromine, or iodine. Similarly, referring to Chart F, olefin L is transformed to olefin LI by alkylating with an alkylation agent of the formula

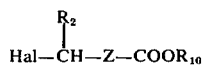

wherein $R_2$, $R_{10}$, Z, and Hal are as defined above.

Any of the alkylation procedures known in the art to be useful for alkylating cyclic ketones with alkyl halides and haloalkanoic esters are used for the transformations of XLIII to XLIV, and of L to LI. See, for example, the abovementioned Belgian Pat. No. 702,477 for procedures useful here and used there to carry out similar alkylations.

For these alkylations, it is preferred that Hal be bromo or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Especially preferred is potassium tert-butoxide. Preferred diluents for this alkylation are tetrahydrofuran and 1,2-dimethoxyethane. Otherwise, procedures for producing and isolating the desired Formula XLIV and -LI compounds are within the skill of the art.

These alkylation procedures produce mixtures of alpha and beta alkylation products, i.e., a mixture of Formula-XLIV products wherein part has the $-CH-R_2-V-COOR_{10}$ moiety attached in alpha configuration, and wherein part has that moiety attached in beta configuration, or a mixture of Formula-LI products with the $-CHR_2-Z-COOR_{10}$ moiety in both alpha and beta configurations. When about one equivalent of base per equivalent of Formula-XLIII or L ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Charts E and F. Silica gel chromatography is preferred for this separation.

The necessary alkylating agents for the above-described alkylations, i.e., compounds of the formulas

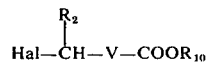

and

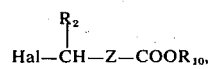

are prepared by methods known in the art. There are eight groups of compounds encompassed by these two genera of alkylating agents.

Alkylating agents of the formula

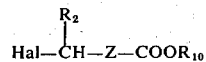

include compounds of the formulas:

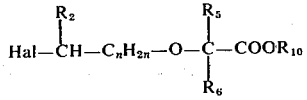  LX

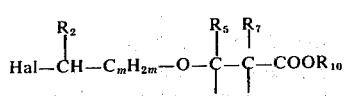  LXI

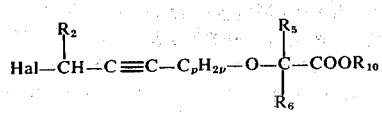  LXII

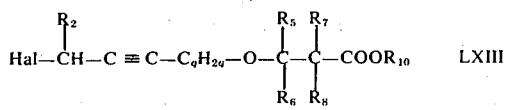

Alkylating agents of the formula

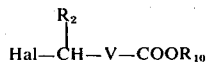

include the above-listed compounds of Formulas LX, LXI, LXII, and LXIII, and also compounds of the following formulas:

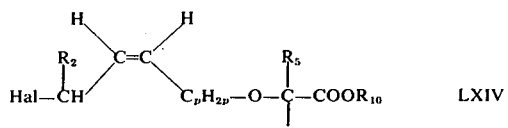

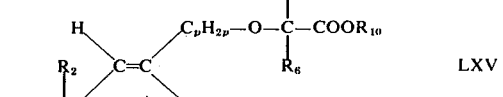

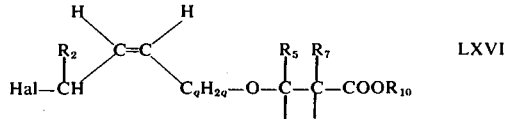

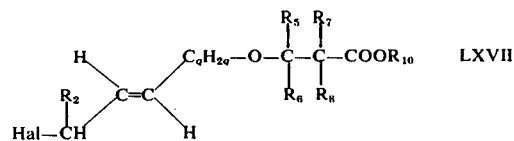

These alkylating agents of Formulas LX to LXVII are accessible to those of ordinary skill in the art. For example, the 3-oxa alkylating agents of Formulas LX, LXII, LXIV, and LXV are advantageously prepared by reacting an alpha-hydroxy ester or acid of the formula HO-CR five R$_6$-COOR$_1$,
wherein R$_1$, R$_5$, and R$_6$ are as defined above, with a compound of the formula,

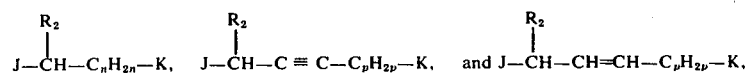

respectively, wherein R$_2$, $n$, and $p$ are as defined above, J is chloro, bromo, iodo, or a group transformable to one of those, for example, tetrahydropyranyloxy or mesyloxy, and K is chloro, bromo, iodo, mesyloxy, tosyloxy, or the like, in the presence of a strong base, for example, sodium hydride when R$_1$ is a carbon-containing group, and lithium diisopropyl amide when R$_1$ is hydrogen. Alternatively, an alpha-bromo ester or acid of the formula Br-CR$_5$R$_6$-COOR$_1$, wherein R$_1$, R$_5$, and R$_6$ are as defined above, is reacted in the presence of a similar strong base with a compound of the formula

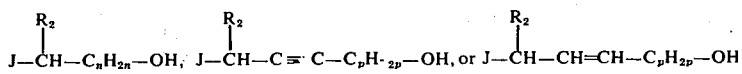

or J—CH—CH=CH—C$_p$H$_{2p}$—OH. When both R$_5$ and R$_6$ in the ester are alkyl, it is preferred to use the hydroxy acid or ester route. When there are two alkyl groups in C$_n$H$_{2n}$ or C$_p$H$_{2p}$ on the carbon to which —OH or —K is attached, it is preferred to use the bromo acid or ester route. When a Formula LX, LXII, LXIV, or LXV alkylating agent is desired wherein both R$_5$ and R$_6$ are alkyl and C$_n$H$_{2n}$ or C$_p$H$_{2p}$ has two alkyl groups attached to the carbon to which —O— is attached, it is preferred that K be mesyloxy or tosyloxy, or that the Br of the bromo acid or ester be replaced with mesyloxy or tosyloxy, and that relatively mild bases and reaction conditions be used, for example, potassium tert-butoxide in dimethyl sulfoxide. Alternatively, this group of tetraalkyl compounds is advantageously prepared by using the hydroxy acid or ester route wherein J is chloro or by using the bromo acid or ester route wherein the bromo is replaced with chloro, using freshly precipated wet magnesium hydroxide in ethanol suspension as the base. Alternatively this group of tetraalkyl compounds is advantageously prepared by the hydroxy acid or ester route wherein J is iodo, and silver oxide is used as the base. Any of these alternative routes is, of course, useful to make the other compounds within the scope of Formulas LX, LXII, LXIV, and LXV.

An alternative procedure generally applicable to the production of the alkylating agents of Formulas LX, LXII, LXIV, and LXV comprises reacting a compound of the formula J—CH—C$_n$H$_{2n}$—OH, J—CH—C≡C—C$_p$H$_{2p}$—OH, or J—CH—CH=CH—C$_p$H$_{2p}$—OH with an ethylene oxide of the formula

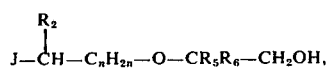

wherein R$_5$ and R$_6$ are as defined above, in the presence of an acid catalyst, e.g., hydrochloric acid, sulfuric acid, or boron trifluoride. The alcohol which is usually the major product,

or cis or trans

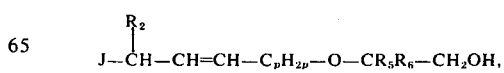

is isolated, oxidized to the corresponding carboxylic acid with Jones reagent, and the acid esterified (R$_{10}$).

The 4-oxa alkylating agents of Formulas LXI, LXIII, LXVI, and LXVII are advantageously prepared as described above for the 3-oxa compounds, combining compounds of the formula

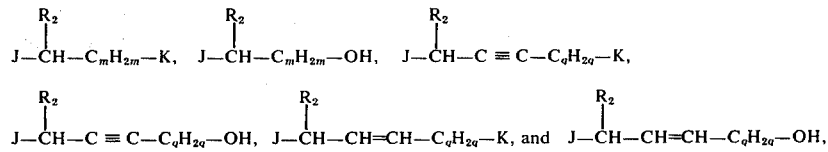

with β-hydroxy acids or esters and β-halo acids or esters of the formulas HO—CR$_5$R$_6$—CR$_7$R$_8$ —$_{COOR1}$ and Br—CR$_5$R$_6$—CR$_7$R$_5$—COOR$_1$, or trimethylene oxides of the formula R—R$_6$C—CR$_7$R$_8$—CH$_2$-0. All of the procedures, preferrences, and alternatives described above for the preparation of the 3-oxa alkylating agents are applicable to the preparation of these 4-oxa alkylating agents.

The alkylating agents of Formulas LX to LXVII are esters. When an alpha or beta hydroxy acid or bromo acid is used as a reactant as described above, the resulting product is a carboxylic acid. This acid is esterified to the corresponding Formula LX-to-LXII alkylating agent by known procedures. As will be described hereinafter, the ester moiety R$_{10}$ is chosen according to the desired type of final 3-oxa or 4-oxa prostaglandin-like product.

The alpha-hydroxy, alpha-halo, beta-hydroxy, and beta halo acids and esters and the ethylene and trimethylene oxides used as described above to produce the Formula LX-to-LXVII alkylating agents are all known in the art or are readily accessible through known methods to those of ordinary skill in the art.

The other reactants of the formulas

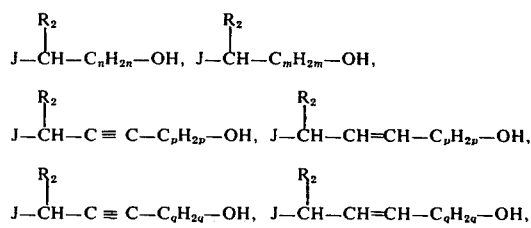

and the corresponding reactants with halogen, mesyloxy, or tosyloxy in place of -OH also are known in the art or are readily accessible through known methods to those of ordinary skill in the art.

For example, consider the compounds

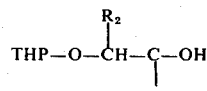

wherein R$_2$ is hydrogen or alkyl of one to 4 carbon atoms, inclusive, as defined above, THP represents 2-tetrahydropyranyl, and each free valence — is attached to hydrogen or to alkyl, with a total of zero to 9 attached alkyl carbon atoms. Said compounds are within the scope of

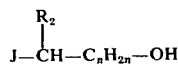

as above defined, and are advantageously prepared by hydroxylating by known methods, olefins of the formula

to give the glycols

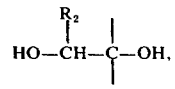

which are transformed by known methods to the above tetrahydropyranyl ethers. These ethers are also transformed by known methods to

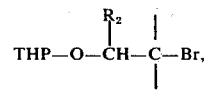

compounds within the scope of

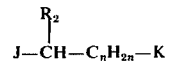

as above defined.

Consider the compounds

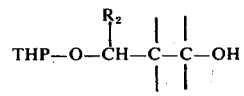

wherein R$_2$ and THP are as above defined, and the free valences are attached to hydrogen or to alkyl, with a total of zero to 8 attached alkyl carbon atoms. Said compounds are within the scope of

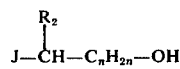

as above defined, and are advantageously prepared by known methods from beta-hydroxyesters of the formula

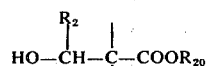

wherein R$_2$ is as defined above, R$_{20}$ is methyl or ethyl and the free valences are attached to hydrogen or to alkyl. Said esters are available through methods known in the art, e.g., the Reformatsky reaction. Said compounds are also transformed by known methods to

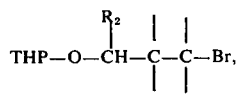

compounds within the scope of

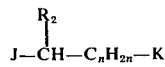

as above defined.

Consider the compounds

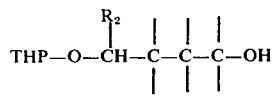

wherein $R_2$ and THP are as defined above and the free valences are attached to hydrogen or to alkyl, with a total of zero to 7 attached alkyl carbon atoms. Said compounds are within the scope of

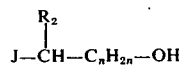

as above defined, and are advantageously prepared by known methods from the known succinic acid half esters of the formula

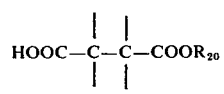

wherein $R_{20}$ is methyl or ethyl, the carboxyl end being transformed to

and then the $-COOR_{20}$ end being transformed to

both by known methods. Said compounds are also transformed by known methods to

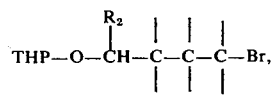

compounds within the scope of

as above defined.

Consider the compounds to

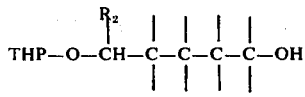

wherein $R_2$ and THP are as defined above and the free valences are attached to hydrogen or to alkyl, with a total of zero to 6 attached alkyl carbon atoms. Said compounds are within the scope of

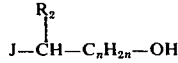

as above defined, and are advantageously prepared by known methods from

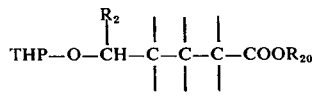

wherein THP, $R_2$, and the free valence attachments are as above defined, and $R_{20}$ is methyl or ethyl. These ester reactants are prepared by known methods from

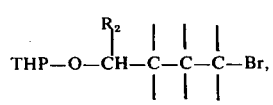

reactants whose preparation is described in the preceeding paragraph. Said compounds are also transformed by known methods to

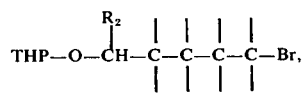

compounds within the scope of

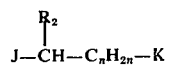

as above defined. In a similar manner, compounds of the formulas

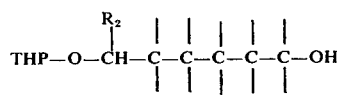

and

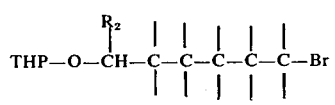

wherein the free valences are attached to hydrogen or to alkyl, with a total of zero to 5 attached alkyl carbon atoms, are prepared from

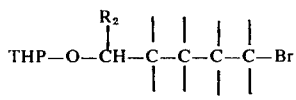

compounds.

Consider the compounds

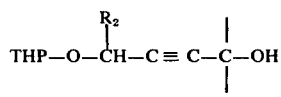

wherein $R_2$ and THP are as above defined, and the free valences are attached to hydrogen or to alkyl, with a total of zero to seven attached alkyl carbon atoms. Said compounds are within the scope of

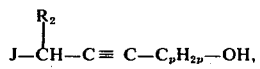

as above defined, and are prepared by known methods from reactants of the formula

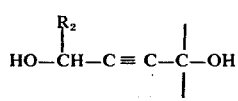

which are known in the art or are prepared by known methods. See, for example, U.S. Pat. No. 3,108,140. Said compounds are also transformed by known methods to

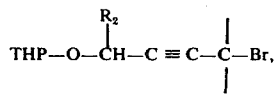

compounds within the scope of

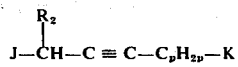

as above defined.

Consider the compounds

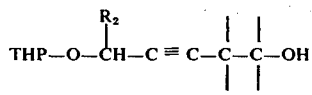

wherein $R_2$ and THP are as above defined, and the free valences are attached to hydrogen or to alkyl, with a total of zero to six attached alkyl carbon atoms. Said compounds are within the scope of

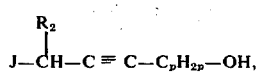

as above defined, and are prepared by known methods from the known or easily accessible beta-hydroxy esters of the formula

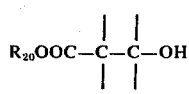

wherein $R_{20}$ is methyl or ethyl. The hydroxy end of those is changed to —O—THP and the $R_{20}OOC$ end is changed to

both by known methods. Then

is changed by known methods first to HC ≡ C— and then to

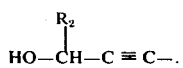

Finally

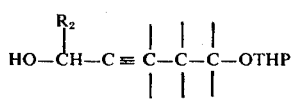

is transformed by known methods to

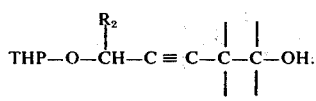

The latter is also transformed by known methods to

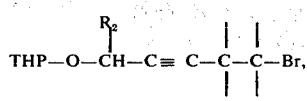

compounds within the scope of

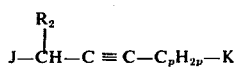

as above defined.

Another route to compounds

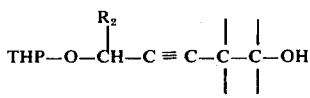

as above defined comprises Reformatsky-type reactions of propargyl bromides of the formula

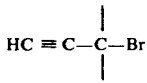

with ketones or aldehydes

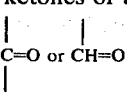

to give

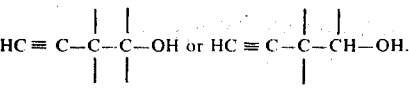

See, for example, J. Chem. Soc. (London) 2696 (1949). Then —OH is changed to —O—THP and HC ≡ C— is changed to $$\text{HO—CH(R}_2\text{)—C} \equiv \text{C—},$$

both by known methods. Finally, $$\text{HO—CH(R}_2\text{)—C} \equiv \text{C—C(—)(—)—C(—)(—)—O—THP}$$

is changed to $$\text{THP—O—CH(R}_2\text{)—C} \equiv \text{C—C(—)(—)—C(—)(—)—OH}$$

by known methods.

Consider the compounds $$\text{THP—O—CH(R}_2\text{)—C} \equiv \text{C—C(—)(—)—C(—)(—)—C(—)(—)—OH}$$

wherein $R_2$ and THP are as above-defined, and the free valences are attached to hydrogen or to alkyl, with a total of zero to 5 attached alkyl carbon atoms. Said compounds are within the scope of $$\text{J—CH(R}_2\text{)—C} \equiv \text{C—C}_p\text{H}_{2p}\text{—OH}$$

as above defined, and are prepared by known methods from the known succinic acid half esters of the formula $$\text{HOOC—C(—)(—)—C(—)(—)—COOR}_{20}$$

wherein $R_{20}$ is methyl or ethyl. The carboxyl end is changed to Br— and the —COOR$_{20}$ end is changed to $$\text{—C(—)(—)—O—THP,}$$

both by known methods. Then, Br— is changed first to HOOC— and then to $$\text{CH}_3\overset{\overset{\text{O}}{\|}}{\text{C}}\text{—},$$

both by known methods. Then $$\text{CH}_3\overset{\overset{\text{O}}{\|}}{\text{C}}\text{—}$$

is changed first to HC ≡ C— and then to $$\text{HO—CH(R}_2\text{)—C} \equiv \text{C—},$$

both by known methods. Finally, $$\text{HO—CH(R}_2\text{)—C} \equiv \text{C—C(—)(—)—C(—)(—)—C(—)(—)—O—THP}$$

is transformed by known methods to $$\text{THP—O—CH(R}_2\text{)—C} \equiv \text{C—C(—)(—)—C(—)(—)—C(—)(—)—OH.}$$

The latter is also transformed by known methods to $$\text{THP—O—CH(R}_2\text{)—C} \equiv \text{C—C(—)(—)—C(—)(—)—C(—)(—)—Br,}$$

compounds within the scope of $$\text{J—CH(R}_2\text{)—C} \equiv \text{C—C}_p\text{H}_{2p}\text{—K}$$

as above defined.

Another route to compounds of the formulas $$\text{THP—O—CH(R}_2\text{)—C} \equiv \text{C—CH(—)—C(—)(—)—OH and THP—O—CH(R}_2\text{)—C} \equiv \text{C—CH(—)—C(—)(—)—C(—)(—)—OH,}$$

both types within the scope of $$\text{J—CH(R}_2\text{)—C} \equiv \text{C—C}_p\text{H}_{2p}\text{—OH}$$

as above defined comprises reaction of $$\text{HO—CH(R}_2\text{)—C} \equiv \text{CH with Br—CH(—)—C(—)(—)—OH}$$

or $$\text{Br—CH(—)—C(—)(—)—C(—)(—)—OH}$$

by known procedures. These latter reactants are known or easily accessible by known methods.

The reactants of formulas $$\text{J—CH(R}_2\text{)—C}_m\text{H}_{2m}\text{—OH and J—CH(R}_2\text{)—C}_m\text{H}_{2m}\text{—K}$$

are prepared as described above for the preparation of the corresponding $C_nH_{2n}$ compounds, due consideration being given to the definition differences between $C_nH_{2n}$ and $C_mH_{2m}$. Similarly, reactants of formulas

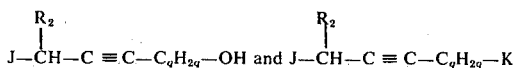

are prepared as described above for the preparation of the corresponding $C_pH_{2p}$ compounds, due consideration being given to the definition differences between $C_pH_{2p}$ and $C_qH_{2q}$.

The cis and trans ethylenic reactants of formulas

are prepared by cis or trans reduction of the corresponding acetylenic reactant prepared as above described, or by cis or trans reduction of any earlier acetylenic intermediate in which both ends of the acetylenic bond are substituted, i.e., not hydrogen as in the moiety $HC \equiv C-$. Alternatively, this cis or trans reduction is carried out on any subsequent acetylenic reaction product leading up to and including the final acetylenic alkylating agent of Formula LXII or LXIII.

For these cis reductions of the acetylenic bonds, it is advantageous to use hydrogen plus a catalyst which catalyzes hydrogenation of $-C \equiv C-$ only to cis $-CH=CH-$. Such catalysts and procedures are well known to the art. See, for example, Fieser et al., "Reagents for Organic Syntheses", pp. 566–567; John Wiley & Sons, Inc., New York, N.Y. (1967). Palladium (5%) on barium sulfate, especially in the presence of pyridine as a diluent, is a suitable catalyst for this purpose. Alternative reagents useful to transform these acetylenic compounds to cis-ethylenic compounds are bis(3-methyl-2-butyl)borane ("disiamylborane") and diisobutylaluminum hydride.

For trans reductions of the acetylenic bond, it is advantageous to use sodium or lithium in liquid ammonia or a liquid alkylamine, e.g., ethylamine. When the moiety $HO-CH_2-C \equiv C-$ is present in the acetylenic compound being reduced, the use of lithium aluminum hydride gives trans reduction of the triple bond. Procedures for these trans reductions are known in the art. See, for example, Fieser et al., above cited, pp. 577, 592–594, and 603, and J. Am. Chem. Soc. 85, 622 (1963).

Referring again to Chart E, after alkylation as discussed above, cyclic ketal LXIV is transformed to glycol XLV by reacting the cyclic ketal with an acid with pK less then 5. Suitable acids and procedures for hydrolyzing cyclic ketals to glycols are known in the art. Suitable acids are formic acid, hydrochloric acid, and boric acid. Especially preferred as diluents for this reaction are tetrahydrofuran and β-methoxyethanol.

Referring again to Chart F, after alkylation as discussed above, olefin LI is hydroxylated glycol LII. As discussed above, the divalent moiety $-Z-$ includes the moieties $-C_nH_{2n}-O-CR_5R_6-$, $-C_mH_{2m}-O-CR_5R_6-CR_7R_8-$, $-C \equiv C-C_pH_{2p}-O-CR_5R_6-$, and $-C \equiv C-C_qH_{2q}-O-CR_5R_6-CR_7R_8-$, wherein $m$, $n$, $p$, $q$, $R_5$, $R_6$, $R_7$, and $R_8$ are as defined above. When Z is $-C_nH_{2n}-O-CR_5R_6-$ or $-C_mH_{2m}-O-CR_5R_6-CR_7R_8-$, this hydroxylation of LI is carried out as described above for the hydroxylation of olefin L to glycol LVIII, i.e., with any of the known reagents and procedures described in Gunstone, above cited. When Z is $-C \equiv C-C_pH_{2p}-O-CR_5R_6-$ or $-C \equiv C-C_qH_{2q}-O-CR_5R_6-CR_7R_8-$, some of the reagents and procedures described by Gunstone tend to attack the acetylenic linkage as well as the ethylenic linkage of the Formula-LI olefin. Therefore it is preferred to use a hydroxylation reagent and procedure which attacks the ethylenic linkage preferentially. For this, it is preferred to carry out hydroxylation of these acetylenic Formula-LI olefins with organic peracids, e.g., performic acid, peracetic acid, perbenzoic acid, and m-chloroperbenzoic acid, as described by Gunstone, above cited, pp. 124–130.

As discussed above regarding the hydroxylation of unalkylated olefin L to unalkylated glycol LVIII various isomeric glycols are obtained by hydroxylation of the Formula-LI alkylated olefin. The particular Formula-LII glycol or glycol mixture obtained depends on such factors as whether the olefin LI is cis or trans and endo or exo, and whether a cis or a trans hydroxylation takes place. However, all of the isomeric Formula-LI erythro and threo glycols and the various glycol mixtures each are useful as an intermediate according to this invention and the processes of Chart F to produce final products of Formulas LIV and LV, and then according to Charts A, B, C, and D, to produce the other final products of this invention. Therefore, it is usually not necessary to separate individual Formula-LI glycol isomers before proceeding further in the synthesis, although that separation is accomplished by silica gel chromatography.

It is preferred that glycols XLV and LII of Charts E and F, respectively, be free of phenolic hydroxyl substituents before the alkanesulfonation step. If any of the intermediate Formula-XLV or Formula-LII compounds have phenolic hydroxyls, these hydroxyls are readily converted to tetrahydropyranyloxy (OTHP) by reaction with dihydropyran, e.g. in the presence of a catalytic amount of $POCl_3$. The $-OTHP$ group is subsequently replaced by OH under neutral or mildly acidic conditions.

Referring again to Charts E and F, bis(alkanesulfonic acid) esters XLVI and LIII are prepared by reacting glycols XLV and LII, respectively, with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25° C. for several hours. The Formula-XLVI and LIII bis(sulfonic acid) esters are then isolated by procedures known to the art.

Referring now to Chart E, bis(sulfonic acid) esters XLVI are transformed either to 3-oxa and 4-oxa phenyl-substituted PGE type compounds XLVII, or to 3-oxa and 4-oxa phenyl-substituted PGA type compounds XLVIII. Referring to Chart F, bis(sulfonic acid) esters LIII are transformed either to 3-oxa and 4-oxa phenyl-substituted PGE type compounds LIV, or to 3-oxa and 4-oxa phenyl-substituted PGA type compounds LV.

The transformations of XLVI and LIII to the PGE type compounds XLVII and LIV, respectively, are carried out by reacting bis-esters XLVI and LIII with water in the range about 0° to about 60° C. In making the 3-oxa and 4-oxa phenyl-substituted PGE$_1$ compounds, 25° C. is a suitable reaction temperature, the reaction then proceeding to completion in about 5 to 20 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of Formula-XLVII or Formula-LIV isomers which differ in the configuration of the side chain hydroxy, that being either S or R. These are separated from byproducts and from each other by silica gel chromatography. A usual byproduct is the mono-sulfonic acid ester of Formula XLIX (Chart E) of Formula LVI (Chart F;. These mono-sulfonic acid esters are esterified to the Formula-XLVI or -LIII bis(-sulfonic acid) esters, respectively, in the same manner described above for the tranformation of glycol XLV or LII to bis-ester XLVI or LIII and thus are recycled back to additional formula XLVII or LIV final product.

The transformations of XLVI and LIII to the PGA type compounds XLVIII and LV, respectively, are carried out by heating bis-esters XLVI and LIII in the range 40° to 100° C. with a combination of water, a base characterized by its water solution having a pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-esters XLVI and LIII to PGE type products XLVII and LIV. The same mono-sulfonic acid esters XLIX and LVI observed as byproducts in those transformations are also observed during preparation of PGA type products XLVIII and LV.

For the transformations of bis(sulfonic acid) esters XLVI and LIII to final products XLVII, XLVIII, LIV, and LV, it is preferred to use the bis-mesyl esters, i.e., compounds XLVI and LIII wherein R$_{13}$ is methyl.

Referring again to Charts E and F, the configuration of the

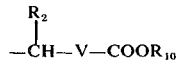

moiety in the Formula-XLVI bis-esters or the configuration of the

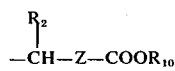

moiety in the Formula-LIII bis-esters does not change during these transformations of XLVI to XLVII, XLVIII, and XLIX, and of LIII to LIV, LV, and LVI.

Therefore, when in Formula XLVI for example, V is —(CH$_2$)$_2$—O—(CH$_2$)$_2$—,

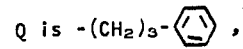

and R$_2$, R$_3$ and R$_4$ are hydrogen, S and R 4-oxa-18-phenyl-19,20-dinor-PGE$_1$ esters (XLVII) are obtained when

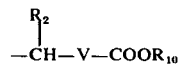

is attached initially (XLVI) in alpha configuration, and S and R 8-iso-4-oxa-18-phenyl-19,20-dinor-PGE$_1$ esters (XLVII) are obtained when that moiety is attached in beta configuration. Similarly, when in Formula XLVI, V is cis-CH=CH—CH$_2$—O—CH$_2$— or —C≡CCH$_2$—C—CH$_2$—, Q is

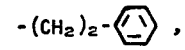

and R$_2$, R$_3$, and R$_4$ are hydrogen, S and R 3-oxa-17-phenyl-18,19,20-trinor-PGE$_2$ esters and S and R 5,6-dehydro-3-oxa-17-phenyl-18,19,20-trinor-PGE$_2$ esters are obtained when

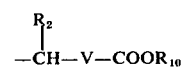

is attached initially in alpha configuration, and the corresponding 8-iso compounds are obtained when that moiety is attached in beta configuration. The same retention of

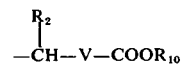

configuration occurs when Formula-XLVIII and XLIX compounds are produced, and a similar retention of

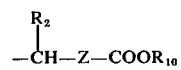

configuration occurs when Formula-LIV, LV, and LVI compounds are produced from Formula-LIII bis-esters.

The Formula-XLVII and LIV 3-oxa and 4-oxa phenyl-substituted PGE type compounds and the Formula-XLVIII and LV 3-oxa and 4-oxa phenyl-substituted PGA type compounds shown in Charts E and F are all R$_{10}$ carboxylic acid esters, wherein R$_{10}$ is as defined above. Moreover, when those PGE-type and PGA-type R$_{10}$ esters are used to prepare the other 3-oxa and 4-oxa phenyl-substituted prostaglandin-like compounds according to Charts A, B, C, and D, corresponding R$_{10}$ esters are likely to be produced, especially in the case of the 3-oxa and 4-oxa phenyl-substituted PGF type compounds. For some of the uses described above, it is preferred that the novel Formula XI-to-XLII 3-oxa and 4-oxa phenyl-substituted prostaglandin-like compounds of this invention be in free acid form, or in salt form which requires the free acid as a starting material.

The PGF-type esters of Formulas XIX to XXVI and the PGB-type compounds of Formulas XXXV to XLII are easily hydrolyzed or saponified to the free acids by the usual known procedures, especially when $R_1$ ($R_{10}$) is alkyl of one to 4 carbons, inclusive, preferably methyl or ethyl.

On the other hand, the PGE type esters of Formulas XI to XVIII and the PGA type esters of Formulas XXVII to XXXIV are difficult to hydrolyze or saponify without causing unwanted structural changes in the desired acids. There are two other procedures to make the free acid forms of these Formula XI-to-XVIII and XXVII-to-XXXIV compounds.

One of those procedures is applicable mainly in preparing the free acids from the corresponding alkyl esters wherein the alkyl group contains one to 8 carbon atoms, inclusive. That procedure comprises subjecting the alkyl ester corresponding to Formulas XI to XVIII and XXVII to XXXIV to the acylase enzyme system of a microorganism species of Subphylum 2 of Phylum III, and thereafter isolating the acid. Especially preferred for this purpose are species of the orders Mucorales, Hypocreales, Moniliales, and Actinomycetales. Also especially preferred for this purpose are species of the families Mucoraceae, Cunninghamellaceae, Nectreaceae, Moniliaceae, Dematiaceae, Tuberculariaceae, Actinomycetaceae, and Streptomycetaceae. Also especially preferred for this purpose are species of the genera Absidia, Circinella, Gongronella, Rhizopus, Cunninghamella, Calonectria, Asperigillus, Penicillium, Sporotrichum, Cladosporium, Fusarium, Nocardia, and Streptomyces.

Examples of microorganisms falling within the scope of those preferred orders, families, and genera are listed in U.S. Pat. No. 3,290,226.

This enzymatic ester hydrolysis is carried out by shaking the Formula XI-to-XVIII or XXVII-to-XXXIV alkyl ester in aqueous suspension with the enzyme contained in a culture of one of the above-mentioned microorganism species until the ester is hydrolyzed. A reaction temperature in the range 20° to 30° C. is usually satisfactory. A reaction time of one to 20 hours is usually sufficient to obtain the desired hydrolysis. Exclusion of air from the reaction mixture, for example, with argon or nitrogen is usually desirable.

The enzyme is obtained by harvest of cells from the culture, followed by washing and resuspension of the cells in water, and cell disintegration, for example, by stirring with glass beads or by sonic or untrasonic vibrations. The entire aqueous disintegration mixture is used as a source of the enzyme. Alternatively and preferably, however, the cellular debris is removed by centrifugation or filtration, and the aqueous supernatant or filtrate is used.

In some cases, it is advantageous to grow the microorganism culture in the presence of an alkyl ester of an aliphatic acid, said acid containing 10 to 20 carbon atoms, inclusive, and said alkyl containing one to 8 carbon atoms, inclusive, or to add such an ester to the culture and maintain the culture without additional growth for one to 24 hours before cell harvest. Thereby, the enzyme produced is sometimes made more effective in transforming the Formula XI-to-XVIII or XXVII-to-XXXIV ester to the free acid. An example of a useful alkyl ester for this purpose is methyl oleate.

This enzymatic hydrolysis is also applicable to the Formula XIX-to-XXXVI PGF type alkyl esters and the Formula XXXV-to-XLII PGB type alkyl esters.

Another procedure for making the free acids of Formula XI-to-XVIII PGE type compounds and Formula XXVII-to-XXXIV PGA type compounds involves treatment of certain haloethyl esters of those acids with zinc metal and an alkanoic acid of 2 to 6 carbon atoms, preferably acetic acid. Those haloethyl esters are the esters wherein $R_{10}$ is ethyl substituted in the $\beta$-position with 3 chloro, 2 or 3 bromo, or one, 2, or 3 iodo. Of those haloethyl moieties, $\beta,\beta,\beta$-trichloroethyl is preferred. Zince dust is preferred as the physical form of the zinc. Mixing the haloethyl ester with the zinc dust at about 25° C. for several hours usually causes substantially complete replacement of the haloethyl moiety of the Formula XI-to-XVIII or XXVII-to-XXXIV ester with hydrogen. The free acid is then isolated from the reaction mixture by procedures known to the art. This procedure is also applicable to the production of Formula XIX-to-XXVI PGF type free acids or Formula XXXV-to-XLII PGB type free acids.

Formula-XLIV cyclic ketals and Formula-LI olefins wherein $R_{10}$ is haloethyl as above defined are necesssary as intermediates for this route to the final PGE, PGF, PGA, and PGB type free acids. These Formula-XLIV and -LI haloethyl ester intermediates can be prepared by alkylation of cyclic ketal XLIII (Chart E) or olefin L (Chart F), respectively, with the appropriate Formula LX-to-LXVII alkylating agent wherein $R_{10}$ is haloethyl as above defined. However, preferred routes to the Formula-XLIV and -LI haloethyl ester intermediates are shown in Charts G and H.

In Charts G and H, $R_2$, $R_3$, $R_4$, Q, $R_{11}$, $R_{12}$, V, Z, and $\sim$ are as defined above. Haloethyl represents ethyl substituted in the $\beta$-position with 3 chloro, 2 or 3 bromo, or 1, 2, or 3 iodo, preferably —$CH_2CCl_3$. $R_{17}$ represents alkyl of one to 4 carbon atoms, inclusive, preferably methyl or ethyl.

Compound LXVIII in Chart G is within the scope of compound XLIV in Chart E. Compound LXXIV in Chart H is within the scope of compound LI in Chart F. Ketones LXVIII and LXXIV are reduced to corresponding hydroxy compounds LXIX and LXXV, respectively, with a carbonyl reducing agent, e.g., sodium borohydride, as described above in discussion of Chart A.

CHART G

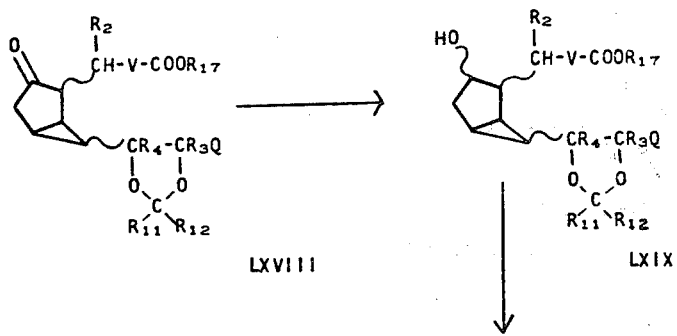

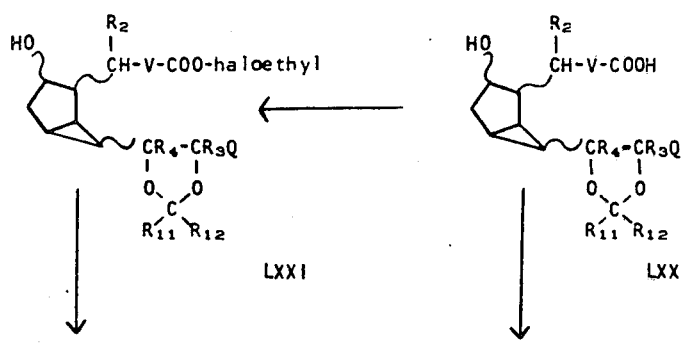
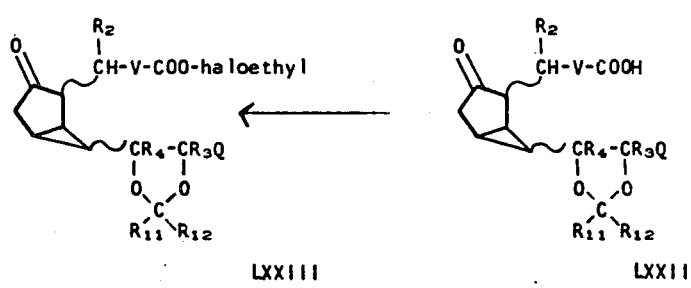
CHART H
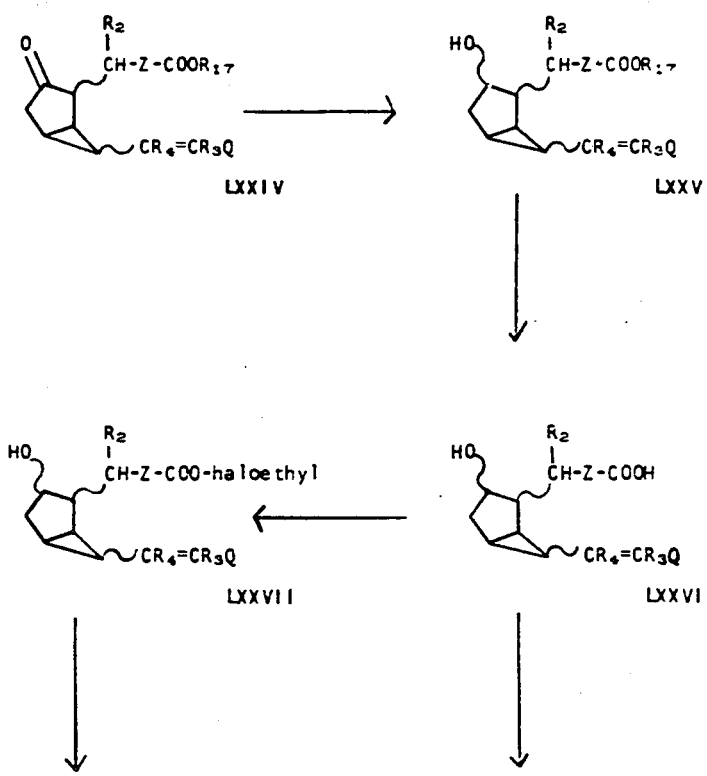
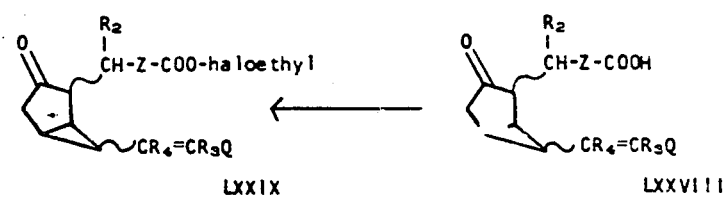

Then, hydroxy esters LXIX and LXXV are saponified by known procedures to hydroxy acids LXX and LXXVI, respectively. These two hydroxy acids are transformed to keto haloethyl esters LXXIII and LXXIX, respectively, by oxidation of the hydroxy group to keto and esterification of the carboxyl group to -COO-haloethyl. As shown in Charts G and H, these two reactions are carried out in either order. However, it is preferred to oxidize first and then esterify.

Hydroxy acids LXX and LXXVI are oxidized to keto acids LXXII and LXXVIII, respectively, and hydroxy haloesters LXXI and LXXVII are oxidized to keto haloesters LXXIII and LXXIX, respectively, by reaction with oxidizing agent which does not attack other parts of these molecules, especially the cyclic ketal group of compounds LXX and LXXI or the ethylenic linkage of compounds LXXVI and LXXVII. An especially useful reagent for this purpose is the Jones reagent, i.e., acidic chromic acid. Acetone is a suitable diluent for this purpose, and a slight excess of oxidant and temperatures at least as low as about 0° C., preferably about −10° to about −20° C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Soc. 87, 5661 (1965).

Haloethyl esters LXXI, LXXIII, LXXVII, and LXXIX are prepared by reacting acids LXX, LXXII, LXXVI, and LXXVIII, respectively, with the appropriate haloethanol, e.g., $\beta$, $\beta$, $\beta$-trichloroethanol, in the presence of a carbodiimide, e.g., dicyclohexylcarbodiimide, and a base, e.g., pyridine, preferably in the presence of an inert liquid diluent, e.g, dichloromethane, for several hours at about 25° C.

As described above, the alkylations of cyclic ketal XLIII to XLIV (Chart E) and olefin L to LI (Chart F) usually produce mixtures of alpha and beta alkylation products with respect to the

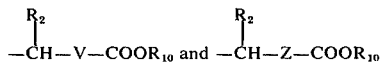

moieties. Also as described above, those two isomers lead to different final products, alpha leading to the PG type series, and beta leading to the 8-iso-PG type series. If a compound in one or the other of those two series is preferred, there are two methods for favoring production of the preferred final product.

One of those methods involves isomerization of the final product of Formulas XI to XVIII. Either the alpha isomer of a Formula XI-to-XVIII compound, ester or free acid, of the corresponding beta isomer is maintained in an inect liquid diluent in the range 0° to 80° C. and in the presence of a base characterized by its water solution having a pH below about 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° takes about one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner by repeated isomerizations and separations, substantially all of the less preferred isomer of the Formula XI-to-XVIII compound is transformed to more preferred isomer.

The second method for favoring production of a preferred Formula XI-to-XVIII isomer involves any one of the keto intermediates of Formulas XLIV, XLV, LI, or LII (Charts E and F). Either the alpha form or the beta form of one of those intermediates is transformed to a mixture of both isomers by maintaining one or the other isomer, alpha or beta, in an inert liquid diluent in the presence of a base and in range 0° to 100° C. until a substantial amount of the starting isomer has been isomerized to the other isomer. Preferred bases for this isomerization are alkali metal amides, alkali metal alkoxides, alkali metal hydrides, and triarylmethyl alkyli metals. Especially preferred are alkali metal tertalkoxides of 4 to 8 carbon atoms, e.g., potassium tertbutoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromatography. The less preferred isomer is then subjected to the same isomerization to produce more of the preferred isomer. In this manner, by repeated isomerizations separations, substantially all of the less preferred isomer of any of these intermediates is transformed to the more preferred isomer. Cyclic ketalketone intermediates of Formula XLIV are preferred over the other intermediates for this isomerization procedure.

The novel 3-oxa and 4-oxa phenyl-substituted PGE, PGF, PGA and PGB type compounds of Formula XI to XLII wherein $R_3$ is alkyl of one to 4 carbon atoms, inclusive, preferably methyl or ethyl, are preferred over the corresponding 3-oxa and 4-oxa phenyl-substituted PGE, PGF, PGA and PGB type compounds in which $R_3$ is hydrogen for the above-described pharmacological purposes.

These 15-alkyl prostaglandin analogs are suprisingly and unexpectedly more useful than the corresponding 15-hydrogen compounds for the reason that they are substantially more specific with regard to potency in causing prostaglandin-like biological responses, and have substantially longer duration of biological activity. For that reason, fewer and smaller doses of these 15-alkyl prostaglandin analogs are needed to attain the desired pharmacological results.

Although the above-mentioned 15-alkyl compounds are produced by the methods outlined above in Charts A–F, the preferred methods are set forth in Chart I and J as follows.

In Chart I is shown the transformation of 15-alkyl PGF-type acids and alkyl esters to the corresponding PGE-type acids and alkyl esters by oxidation. For this purpose, an oxidizing agent is used which selectively oxidizes secondary hydroxy groups to carbonyl groups in the presence of carbon-carbon double bonds.

CHART I

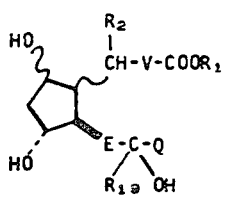

LXXX (Oxidation)

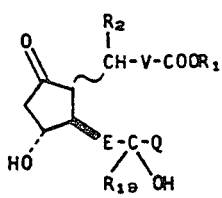

LXXXI

Formula LXXX in Chart I includes optically active compounds as shown and racemic compounds of that formula and the mirror images thereof, and also the 15-epimers of both of those, i.e., wherein the configuration at C-15 is R rather than s as shown. Also in Chart I, E, Q, $R_1$, $R_2$, and V are as defined above, and $R_{19}$ is alkyl of one to 4 carbon atoms.

For the transformation of Chart I, the β-hydroxy isomers of reactant LXXX are preferred starting materials when the carboxyl side chain is alpha, although the corresponding α-hydroxy isomers are also useful for this purpose.

Oxidation reagents useful for the transformation set forth in Chart I are known to the art. An especially useful reagent for this purpose is the Jones reagent, i.e., acidified chromic acid. See J. Chem. Soc. 39 (1946). A slight excess beyond the amount necessary to oxidize one of the secondary hydroxy groups of the Formula-LXXX reactant is used. Acetone is a suitable diluent for this purpose. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the Formula-LXXXI PGE-type product is isolated by conventional methods.

Examples of other oxidation reagents useful for the Chart I transformations are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

The novel 15-alkyl 3-oxa and 4-oxa phenyl-substituted PGF -and PGF -type acids and esters of Formulas XIX to XXVI wherein $R_3$ is one to 4 carbon atoms, inclusive, are preferably prepared from the corresponding 15-hydrogen compounds by the sequence of transformations shown in Chart J, wherein Formulas LXXXII through LXXXVI, inclusive, include optically active and racemic S and R compounds of those formulas and the mirror images thereof. Also in Chart J, $R_{19}$ is alkyl of one to 4 carbon atoms, inclusive, and E, Hal, Q, $R_1$, $R_2$, and V are as heretofore defined; Q'' in Formula LXXXIV is

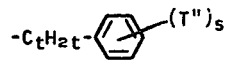

wherein T'' is the same as T above except that, in $R_9$, —Si(G)$_3$ replaces hydrogen. Also in Chart J, G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{14}$ is $R_1$ as defined above or silyl of the formula —Si—(G)$_3$ wherein G is as defined above. The various G's of a —Si(G)$_3$ moiety are alike or different. For example, a —Si(G)$_3$ can be trimethylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

CHART J

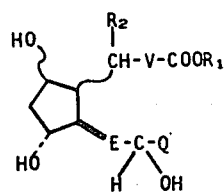

LXXXII (oxidation)

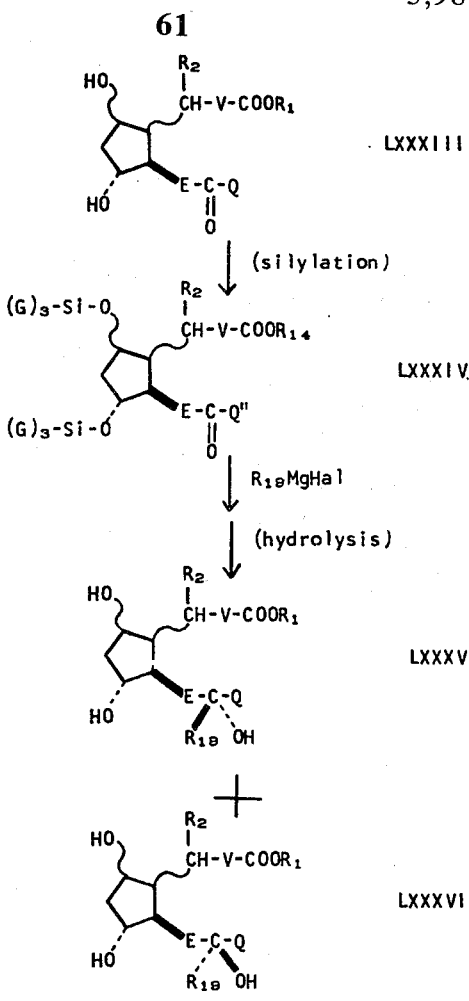

In Chart J, the final PGFα and PGFβ -type products are those encompassed by Formulas LXXXV and LXXXVI, respectively.

The initial optically active or racemic reactants of Formula LXXXII in Chart J. i.e., the 3-oxa and 4-oxa phenyl-substituted PGF$_1$-, PGF$_2$-, dehydro-PGF$_2$-, and dihydro-PGF$_1$-type compounds in their α and β forms, and their esters, are prepared by methods described herein. Thus, racemic 3-oxa and 4-oxa phenyl-substituted dihydro-PGF$_{1\alpha}$ - and -PGF$_{1\beta}$ -type compounds, and their esters are prepared by catalytic hydrogenation of the corresponding racemic 3-oxa and 4-oxa phenyl-substituted PGF$_{1\alpha}$ or PGF$_{2\beta}$, and PGF$_{1\alpha}$ or PGF$_{2\beta}$ type compounds, respectively, e.g. in the presence of 5% palladium-on-charcoal catalyst in ethyl acetate solution at 25° C. and one atmosphere pressure of hydrogen.

The heretofore-described acids and esters of Formula LXXXII are transformed to the corresponding intermediate 15-dehydro acids and esters of Formula LXXXIII, by oxidation with reagents such as 2,3-dichloro-5,6-dicyano-1,4-benzoquinone, activated manganese dioxide, or nickel peroxide (see Fieser et al., "Reagents for Organic Synthesis," John Wiley & Sons, Inc., New York, N.Y. pp. 215, 637, and 731). Alternatively, and especially for the Formula-LXXXII reactants wherein E and V are —CH$_2$CH$_2$-, these oxidations are carried out by oxygenation in the presence of the 15-hydroxyprostaglandin dehydrogenase of swine lung (see Arkiv for Kemi 25, 293 (1963)). These reagents are used according to procedures known in the art. See, for example, J. Biol. Chem. 239, 4097 (1964).

Referring again to Chart J, the intermediate compounds of Formula LXXXIII are transformed to silyl derivatives of Formula LXXXIV by procedures known in the art. See, for example, Pierce, "Silylation of Organic Compounds," Pierce Chemical Co., Rockford, Ill. (1968). Both hydroxy groups of the Formula-LXXXIII reactants are thereby transformed to —O—Si—(G)$_3$ moieties wherein G is as defined above, and sufficient of the silylating agent is used for that purpose according to known procedures. When R$_1$ in the Formula-LXXXIII intermediate is hydrogen, the —COOH moiety thereby defined is simultaneously transformed to —COO—Si—(G)$_3$, additional silylating agent being used for this purpose. This latter transformation is aided by excess silylating agent and prolonged treatment. Likewise, when R$_9$ in T of the Formula-LXXXIII intermediate is hydrogen, the phenolic hydroxyl thereby defined is simultaneously transformed to —O—Si(G)$_3$ in the silylation step. Q'' in Formula LXXXIV, therefore is

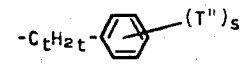

wherein T'' is the same as T above except that, in R$_9$, —Si(G)$_3$ replaces hydrogen. When R$_1$ in Formula LXXXIII is alkyl, then R$_{14}$ in Formula LXXXIV will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

Referring again to Chart J the intermediate silyl compounds of Formula LXXXIV are transformed to the final compounds of Formulas LXXXV and LXXXVI by first reacting the silyl compound with a Grignard reagent of the formula R$_{19}$MgHal wherein R$_{19}$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl, trisilyl, or tetrasilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15—S and 15—R isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15—S and 15—R isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

Although Formula-LXXXV and -LXXXVI compounds wherein E is —CH$_2$CHR$_4$— and V is W as defined above may be produced according to the processes of Chart J, it is preferred to produce those novel dihydro-PGF$_1$ analogs by hydrogenation of one of the corresponding unsaturated compounds, i.e., a compound of Formula LXXXV or LXXXVI wherein E is trans —CH=CR₄— and V is either W, —CH=CH—Y, or —C C—Y—, Y being defined above. This hydrogenation is advantageously carried out catalytically, for example, in the presence of a 5% palladium-on-charcoal catalyst in ethyl acetate solution at 25° C. and one atmosphere pressure of hydrogen.

The novel 15-alkyl 3-oxa and 4-oxa phenyl-substituted PGA-type and PGB-type acids and esters of Formulas XXVII to XLII are prepared from the 15-alkyl 3-oxa and 4-oxa phenylsubstituted PGE compounds, heretofore described, by dehydrations and double bond migrations previously described, as shown in Chart A. Likewise the 15-alkyl PGB-type compounds are prepared by contacting the 15-alkyl PGA-type compounds with base. For the transformation of the 15-alkyl PGE-type compounds to the 15-alkyl PGA-type compounds of this invention (Chart K), it is preferred that a dehydrating agent be used which removes the hydroxy group from the alicyclic ring in the presence of a hydroxy group on a tertiary carbon atom. Formula LXXXVII as shown includes optically active compounds and racemic compounds of that formula and the mirror images thereof, and also the 15-epimers of both of those. Any of the known substantially neutral dehydrating agents is used for these reactions. See Fieser et al., cited above. Preferred dehydrating agents are mixtures of at least an equivalent amount of a carbodiimide and a catalytic amount of a copper (II) salt. Especially preferred are mixtures of at least an equivalent amount of dicyclohexylcarbodiimide and a catalytic amount of copper (II) chloride. An equivalent amount of a carbodiimide means one mole of the carbodiimide for each mole of the Formula-LXXXVII reactant.

CHART K

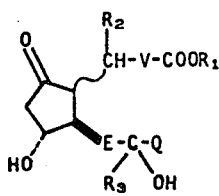

LXXXVII

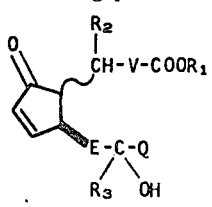

LXXXVIII

To insure completeness of the reaction, it is advantageous to use an excess of the carbodiimide, i.e., 1.5 to 5 or even more equivalents of the carbodiimide.

The dehydration is advantageously carried out in the presence of an inert organic diluent which gives a homogeneous reaction mixture with respect to the Formula-LXXXVII reactant and the carbodiimide. Diethyl ether is a suitable diluent. It is advantageous to carry out the dehydration in an atmosphere of an inert gas, e.g., nitrogen, helium, or argon. The time required for the dehydration will depend in part on the reaction temperature. With the reaction temperature in the range 20° to 30° C., the dehydration usually takes place in about 40 to 60 hours.

The Formula-LXXXVIII product is isolated by methods known in the art, e.g., filtration of the reaction mixture and evaporation of the filtrate. The product is then purified by methods known in the art, advantageously by chromatography on silica gel.

The final Formula XI-to-XLII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the Formula XI-to-XLII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the Formula XI-to-XLII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the Formula XI-to-XLII acid with the stoichiometric amount of the corresponding quaternary ammonium hydroxide in water solution, followed by evaporation of the water.

The final Formula XI-to-XLII acids or esters prepared by the processes of this invention are transformed to lower alkanoates by interaction of the Formula XI-to-XLII hydroxy compound with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure. the Formula XI-to-XVIII PGE type compounds are transformed to dialkanoates, the Formula XIX-to-XXVI PGF type compounds are transformed to trialkanoates, and the Formula XXVII-to-XLII PGA type and PGB type compounds are transformed to monoalkanoates.

When a PGE type dialkanoate is transformed to a PGF type compound by carbonyl reduction as shown in Chart A, a PGF type dialkanoate is formed and is used for the abovedescribed purposes as such or is transformed to a trialkanoate by the above-described procedure. In the latter case, the third alkanoyloxy group can be the same as or different from the two alkanolyoxy groups present before the carbonyl reduction.

Molecules of each of the compounds encompassed by Formulas XI to XLII and, except for L and LVII, of each intermediate formula each have at least one center of asymmetry, and each can exist in racemic form and in either enantiomeric form, i.e., d and l. A formula accurately defining the d form would be the mirror image of the formula which defined the l form. Both formulas are necessary to define accurately the corresponding racemic form. For convenience, the various formulas are to be construed as including racemic, d, and l compounds.

When an optically active (d or l) final compound is desired, that is made by resolution of the racemic compound or by resolution of one of the asymmetric racemic intermediates. These resolutions are carried out by procedures known in the art. For example, when final compound XI to XLII is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of Formula XI to XLII is then obtained by treatment of the salt with an acid by known general procedures. Alternatively, the free acid form of olefin LI, cyclic ketal XLIV, or glycols XLV or LII is resolved into separate d and l forms and then esterified and transformed further to the corresponding optically active form of the final product XI to XLII as described above.

Alternatively, bicyclo ketone reactants XLV or LII, in exo or endo form, are transformed to ketals with an optically active 1,2-glycol, e.g., D—(—)-2,3-butanediol, by reaction of said 1,2-glycol with the Formula-XLV or -LII compound in the presence of a strong acid, e.g., p-toluenesulfonic acid. The resulting ketal is a mixture of diastereoisomers which is separated into the d and l diastereoisomers, each of which is then hydrolyzed with an acid, e.g., oxalic acid, to the original keto compound, now in optically active form. These reactions involving optically active glycols and ketals for resolution purposes are generally known in the art. See, for example, Chem. Ind. 1664 (1961) and J. Am. Chem. Soc. 84,2938 (1962). Dithiols may be used instead of glycols.

The invention can be more fully understood by the following examples and preparations:

All temperatures are in degrees centigrade.

Infrared absorption spectra are recorded on a Perkin-Elmer model 421 infrared spectrophotometer. Except when specified otherwise, undiluted (neat) samples are used.

For all of the preparations and examples herein, the NMR spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

The collection of chromatographic eluate fractions starts when the eluent front reaches the bottom of the column.

PREPARATION 1

Endo-bicyclo[3.1.0]hexan-3-ol-6-carboxylic acid Methyl Ester.

A mixture of endo-bicyclo[3.1.0]hex-2-ene-6-carboxylic acid methyl ester (103 g.) and anhydrous diethyl ether (650 ml.) is stirred under nitrogen and cooled to —5° C. A one molar solution (284 ml.) of diborane in tetrahydrofuran is added dropwise during 30 minutes while keeping the temperature below 0° C. The resulting mixture is then stirred and allowed to warm to 25° C. during 3 hours. Evaporation under reduced pressure gives a residue which is dissolved in 650 ml. of anhydrous diethyl ether. The solution is cooled to 0° C., and 3 normal aqueous sodium hydroxide solution (172 ml.) is added dropwise under nitrogen and with vigorous stirring during 15 minutes, keeping the temperature at 0° to 5° C. Next, 30% aqueous hydrogen peroxide (94 ml.) is added dropwise with stirring during 30 minutes at 0° to 5° C. The resulting mixture is stirred an hour while warming to 25° C. Then, 500 ml. of saturated aqueous sodium chloride solution is added, and the diethyl ether layer is separated. The aqueous layer is washed with four 200-ml. portions of ethyl acetate, the washings being added to the diethyl ether layer, which is then washed with saturated aqueous sodium chloride solution, dried, and evaporated to give 115 g. of a residue. This residue is distilled under reduced pressure to give 69 g. of a mixture of the methyl esters of endo-bicyclo[3.1.0]hexan-3-ol-6-carboxylic acid and endo-bicyclo[3.1.0]hexan-2-ol-6-carboxylic acid; b.p. 86°–95° C. at 0.5 mm.

Preparation 2

Endo-bicyclo[3.1.0]hexan-3-ol-6-carboxylic Acid Methyl Ester Tetrahydropyranyl Ether.

The 2-ol and 3-ol mixture (66 g.) obtained according to Preparation 1 in 66 ml. of dihydropyran is stirred and cooled at 15–20°C. during addition of 3 ml. of anhydrous diethyl ether saturated with hydrogen chloride. The temperature of the mixture is then kept in the range 20° to 30° C. for one hour with cooling, and is then kept at 25° for 15 hours. Evaporation gives a residue which is distilled under reduced pressure to give 66 g. of a mixture of the methyl esterstetrahydropyranyl ethers of endo-bicyclo[3.1.0]hexan-3-ol-6-carboxylic acid and endo-bicyclo[3.1.0]hexan-2-ol-6-carboxylic acid; b.p. 96°–104° C. at 0.1 mm.

Preparation 3

Endo-6-hydroxymethylbicyclo[3.1.0]hexan-3-ol-3-tetrahydropyranyl Ether.

A solution of the mixture (69 g.) of products obtained according to Preparation 2 in 300 ml. of anhydrous diethyl ether is added dropwise during 45 minutes to a stirred and cooled mixture of lithium aluminum hydride (21 g.) in 1300 ml. of anhydrous diethyl ether under nitrogen. The resulting mixture is stirred 2 hours at 25°C., and is then cooled to 0° C. Ethyl acetate (71 ml.) is added, and the mixture is stirred 15 minutes. Water (235 ml.) is then added, and the diethyl ether layer is separated. The water layer is washed twice with diethyl ether and twice with ethyl acetate. A solution of Rochelle salts is added to the aqueous layer, which is then saturated with sodium chloride and extracted twice with ethyl acetate. All diethyl ether and ethyl acetate solutions are combined, washed with saturated aqueous sodium chloride solution, dried, and evaporated to give 61 g. of a mixture of the 3-tetrahydropyranyl ethers of endo-6-hydroxymethylbicyclo[3.1.0]hexane-3-ol and endo-6-hydroxymethylbicyclo[3.1.0]hexan-2-ol.

Preparation 4

Endo-bicyclo[3.1.0]hexan-3-ol-6-carboxaldehyde 3-tetrahydropyranyl Ether.

A solution of the mixture (34 g.) of products obtained according to Preparation 3 in 1000 ml. of acetone is cooled to −10°C. Jones reagent (75 ml. of a solution of 21 g. of chromic anhydride, 60 ml. of water, and 17 ml. of concentrated sulfuric acid), precooled to 0° C., is added dropwise with stirring during 10 minutes at −10° C. After 10 minutes of additional stirring at −10° C., isopropyl alcohol (35 ml.) is added during 5 minutes, and stirring is continued for 10 minutes. The reaction mixture is then poured into 8 l. of an ice and water mixture. The resulting mixture is extracted 6 times with dichloromethane. The combined extracts are washed with aqueous sodium bicarbonate solution, dried, and evaporated to give 27 g. of a mixture of the tetrahydropyranyl ethers of endo-bicyclo[3.1.0]hexan-3-ol-6-carboxaldehyde and endo-bicyclo[3.1.0]hexan-2-ol-6-carboxaldehyde.

Preparation 5

(3-Phenylpropyl)triphenylphosphonium Bromide.

A solution of 597.3 g. of 1-bromo-3-phenylpropane and 786 g. of triphenylphosphine in 1500 ml. of toluene is heated at reflux under nitrogen for 16 hours, then the mixture is cooled and the solid product is separated by filtration. The solid is then slurried with toluene in a Waring blender, separated by filtration, and dried for 18 hours at 70° C. under reduced pressure to give 1068 g. of (3-phenylpropyl)triphenylphosphonium bromide; m.p. 210.5°–211.5° C.

Preparation 6

4-Phenyl-1-butanol.

A solution of 200 g. of 4-phenylbutyric acid in 1500 ml. of anhydrous ether is added with stirring to a suspension of 46.3 g. of lithium aluminum hydride in 1800 ml. of anhydrous ether at a rate sufficient to maintain gentle reflux while the mixture is cooled in an ice bath. Fifteen minutes after the addition is complete the mixture is treated cautiously, under nitrogen, with 93 ml. of water and then 74 ml. of 10% aqueous sodium hydroxide. The mixture is stirred about 18 hours at about 25° C. and dried over sodium sulfate, filtered, and concentrated under reduced pressure to give 171 g. of 4-phenyl-1-butanol; infrared absorption at 3250, 2980, 1610, 1060, 1030, 750 and 700 cm$^{-1}$; NMR peaks at 7.30 (singlet), 3.61 (triplet), 2.65 (multiplet) and 2.75 (singlet) δ.

Preparation 7

4-Phenyl-1-bromobutane.

Phosphorus tribromide (40.5 ml.) is added dropwise to 171 g. of 4-phenyl-1-butanol with cooling to keep the temperature between 0° C. and −5° C. This mixture is allowed to stand 16 hours at 25° C. and is poured into a mixture of ice and aqueous sodium bicarbonate. The mixture is extracted with hexane and the extract is washed with water, aqueous sodium bicarbonate, brine, dried over sodium sulfate and concentrated under reduced pressure to give 196 g. of crude 4-phenyl-1-bromobutane. This is distilled to give 145.2 g. of 4-phenyl-1-bromobutane, b.p. 103°–103.5°/16 mm; NMR peaks at 7.19 (multiplet), 3.14 (triplet) and 2.45 δ.

Preparation 8

(4-Phenylbutyl)triphenylphosphonium Bromide.

A solution of 145 g. of 4-phenyl-1-bromobutane and 179 g. of triphenylphosphine in 350 ml. of toluene is heated at reflux under nitrogen for 16 hours. The mixture is then cooled slowly and ether is added giving a precipitate of (4-phenylbutyl)triphenylphosphonium bromide which is washed thoroughly with benzene/ether and dried 18 hours at 50°C. under reduced pressure, 268 g., m.p. 139°–140° C.

EXAMPLE 1

Endo-6-(cis-4-phenyl-1-butenyl)-bicyclo[3.1.0]hexan-3-one (Formula L: Q is

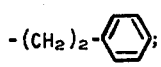

$R_3$ and $R_4$ are hydrogen; and $\sim$ is endo).

A suspension of 314 g. of (3-phenylpropyl)triphenylphosphonium bromide in 3 l. of benzene is stirred at room temperature (25° C.) under nitrogen, and 400 ml. of 1.6 M butyllithium in hexane is added over a 20 min. period. The mixture is heated at 35° C. for 30 minutes, then is cooled to −15° C. and a solution of 100 g. of endo-bicyclo[3.1.0]hexan-3-ol-6-carboxaldehyde 3-tetrahydropyranyl ether in 200 ml. of benzene is added over a 30-min. period. This mixture is heated at 70° C. for 2.5 hours, cooled, and filtered. The filtrate is washed three times with water, dried over sodium sulfate, and evaporated to give 170 g. of crude endo-6-(cis-4-phenyl-1-butenyl)-bicyclo[3.1.0]hexan-3-ol 3-tetrahydropyranyl ether.

A solution of 340 g. (two runs) of this crude endo-6-(cis-4-phenyl-1-butenyl)-bicyclo-[3.1.0]hexan-3-ol 3-tetrahydropyranyl ether and 20 g. of oxalic acid in 3600 ml. of methanol is heated at reflux for 3.5 hours. The mixture is cooled and the methanol is evaporated under reduced pressure. The residue is mixed with dichloromethane, and the dichloromethane solution is washed with aqueous sodium bicarbonate, dried over sodium sulfate, and evaporated to give 272 g. of the endo-6-(cis-4-phenyl-1-butenyl)-bicyclo[3.1.0]hexan-3-ol.

A solution of 93 g. of the above endo-6-(cis-4-phenyl-1-butenyl)bicyclo[3.1.0]hexan-3-ol in 2570 ml. of acetone is cooled to −5° C. and 160 ml. of Jones reagent is added over a period of 30 minutes while cooling to maintain a temperature of −5° C. The mixture is allowed to stand for 10 minutes longer; then 100 ml. of isopropyl alcohol is added and the mixture is swirled for 5 min. The mixture is then diluted with 6 l. of water and extracted several times with dichloromethane. The organic layers are separated, washed with dilute hydrochloric acid, water, dilute aqueous sodium bicarbonate, and brine, then are dried over sodium sulfate, combined and evaporated to give 83 g. of crude endo-6-(cis-4-phenyl-1-butenyl)-bicyclo-[3.1.0]hexan-3-one.

Crude endo-6-(cis-4-phenyl-1-butenyl)-bicyclo[3.1.0]hexan-3-one (162 g., two runs) is dissolved in isomeric hexanes (Skellysolve B) and chromatographed over 5 kg. of silica gel wet-packed with Skellysolve B, eluting successively with 11 l. of Skellysolve B, 62 l. of 2.5% ethyl acetate in Skellysolve B, and 32 l. of 5% ethyl acetate in Skellysolve B. The last 8 l. of the 2.5% ethyl acetate in Skellysolve B eluates and the 32 l. of 5% ethyl acetate in Skellysolve B eluates are combined and evaporated to give 75.8 g. of endo-6-(cis-4-phenyl-1-butenyl)-bicyclo[3.1.0]hexan-3-one; infrared absorption at 3000, 1750, 1610, 1500, 1455, 1405, 1265, 1150, 778, 750, and 702 cm$^{-1}$., N.M.R. peaks at 7.18 (singlet) and 4.75–6.0 (broad multiplet) $\delta$.

EXAMPLE 2

Endo-6-(cis-5-phenyl-1-pentyl)-bicyclo[3.1.0]hexan-3-one. (Formula L: Q is

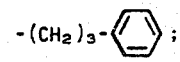

$R_3$ and $R_4$ are hydrogen; and $\sim$ is endo).

A suspension of 242 g. of (4-phenylbutyl)-triphenylphosphonium bromide in 2.3 l. of dry benzene at 25°C. is stirred and 300 ml. of 1.6 M butyllithium in hexane is added over 15 minute period. The mixture is stirred at 30°C. for one hour, then is cooled to 10°C. and a solution of 75 g. of endobicyclo[3.1.0]hexan-3-ol-6-carboxaldehyde 3-tetrahydropyranyl ether is 200 ml. of benzene is added over a 15 minute period. The mixture is heated at 65°–70° C. for 3 hours, cooled and filtered. The filtrate is washed with water and brine, dried over sodium sulfate, and evaporated under reduced pressure to give 117 g. of crude endo-6-(cis-5-phenyl-1-pentyl)-bicyclo[3.1.0]hexan-3-ol tetrahydropyranyl ether showing a single spot, $R_f$ 0.75, on thin layer chromatography with silica gel plates developed with 20% ethyl acetate in cyclohexane.

A solution of 117 g. of the above crude endo-6-(cis-5-phenyl-1-pentenyl)-bicyclo[3.1.0]hexan-3-ol tetrahydropyranyl ether and 6 g. of oxalic acid in 2500 ml. of methanol is heated under reflux for 2.5 hours. The methanol is then removed by distillation under reduced pressure and the residue is diluted with water and extracted with dichloromethane. The dichloromethane extracts are combined, washed with aqueous sodium bicarbonate and brine, dried over sodium sulfate and evaporated under reduced pressure to give 95.7 g. of crude endo-6-(cis-5-phenyl-1-pentenyl)bicyclo-[3.1.0]hexan-3-ol. The entire crude product is chromatographed over 1.5 g. of silica gel wet-packed with Skellysolve B, eluting successively with 5 l. of Skellysolve B, 4 l. of 2.5%, 6 l. of 5%, 9 l. of 7.5%, 12 l. of 10%, 8 l. of 15%, 10 l. of 20% and 10 l. of 30% ethyl acetate in Skellysolve B, taking 600 ml. fractions. The last fraction of 10% ethyl acetate in Skellysolve B, all the 15 and 20% ethyl acetate in Skellysolve B eluates, and the first 3 fractions of 30% ethyl acetate in Skellysolve B are evaporated to give 60.5 g. of purified endo-6-(cis-5-phenyl-1-pentenyl)bicyclo-[3.1.0]hexane-3-ol.

A solution of 60.5 g. of the above purified alcohol in 1600 ml. of acetone is cooled to −10°C. and 103 ml. of Jones reagent is added dropwise. After addition is complete the mixture is stirred for 10 minutes at 0°C. and 65 ml. of isopropyl alcohol is added. The mixture is poured into 8 l. of water and extracted several times with dichloromethane. The dichloromethane extracts are combined, washed with dilute hydrochloric acid, aqueous sodium bicarbonate and brine, dried over sodium sulfate and evaporated under reduced pressure to give 56 g. of crude endo-6-(cis-5-phenyl-1-pentenyl)bicyclo[3.1.0]hexan-3-one. The crude ketone is slurried in Skellysolve B and chromatographed over 2300 g. of silica gel wet packed in Skellysolve B, eluting successively with 6 l. of Skellysolve B, 16 l. of 2.5% ethyl acetate in Skellysolve B, then gradient elution with 5 l. of 2.5% and 5 l. of 5% ethyl acetate in Skellysolve B and finally 16 l. of 5% ethyl acetate in Skellysolve B, taking 625 ml. fractions. The last fraction of the gradient eluates and the first 19 fractions of 5% ethyl acetate in Skellysolve B are concentrated to give 23.6 g. of endo-6-(cis-5-phenyl-1-pentenyl)bicyclo[3.1.0]hexan-3-one; infrared absorption at 2980, 1745, 1600 1490, 1450, 1400, 1260, 1145, 770, 750 and 702 cm$^{-1}$., N.M.R. peaks at 7.17 (singlet), 6.0–5.4 (multiplet), and 5.2–4.7 (broad multiplet) δ.

Following the procedures of Examples 1 and 2, but using intermediate quaternary phosphonium halides prepared as in Preparation 5 from α-bromotoluene, (2-bromoethyl)benzene, (5-chloropentyl)benzene, (6-bromohexyl)benzene, and (7-iodoheptyl)benzene in place of 1-bromo-3-phenylpropane, there are obtained the 2-phenyl-1-ethenyl, 3-phenyl-1-propenyl, 6-phenyl-1-hexenyl, 7-phenyl-1-heptenyl, and 8-phenyl-1-octenyl compounds corresponding to the products of Examples 1 and 2.

Also following the procedures of Examples 1 and 2, but using intermediate quaternary phosphonium halides prepared as in Preparation 5 from (1-chloroethyl)benzene, (1-bromopropyl)benzene, (2-bromopropyl)benzene, (3-chloropentyl)benzene, (4-bromopentyl)benzene, (6-bromononyl)benzene and (7-bromononyl)benzene in place of 1-bromo-3-phenylpropane, there are obtained the 2-methyl-2-phenyl-1-ethenyl, 2-ethyl-2-phenyl-1-ethenyl, 2-methyl-3-phenyl-1-propenyl, 2-ethyl-4-phenyl-1-butenyl, 2-methyl-5-phenyl-1-pentenyl, 2-propyl-7-phenyl-1-heptenyl, and 2-ethyl-8-phenyl-1-octenyl compounds corresponding to the products of Examples 1 and 2.

Also following the procedures of Examples 1 and 2, but using intermediate quaternary phosphonium halides prepared as in Preparation 5 from (2-bromo-1-fluoroethyl)benzene, (2-bromo-1-fluoropropyl)benzene, (2-chloro-1-fluoro-1-methylpropyl)benzene, (5-bromo-4-fluoropentyl)benzene, (7-iodo-6-fluoropentyl)benzene, (4-bromo-3,3-difluorobutyl)benzene, and (6-bromo-5,5-difluorohexyl)benzene in place of 1-bromo-3-phenylpropane, there are obtained the 3-fluoro-3-phenyl-1-propenyl, 3-fluoro-1-methyl-3-phenyl-1-propenyl, 3-fluoro-2,3-dimethyl-3-phenyl-1-propenyl, 3-fluoro-6-phenyl-1-hexenyl, 3-fluoro-8-phenyl-1-octenyl, 3,3-difluoro-5-phenyl-1-pentenyl, and 3,3-difluoro-7-phenyl-1-heptenyl compounds corresponding to the products of Examples 1 and 2.

Also following the procedures of Examples 1 and 2, but using intermediate quaternary phosphonium halides prepared as in Preparation 5 from α-bromo-m-xylene, α-chloro-p-ethyltoluene, α-bromo-p-chlorotoluene, α'-chloro-α,α,α-trifluorom-xylene, 1-(2-bromoethyl)-4-fluorobenzene, 1-(5-bromopentyl)2-chlorobenzene, 4-(3-iodopropyl)-1,2-dimethyoxybenzene, and 1-(3-bromohexyl)-2,4,6-trimethylbenzene in place of 1-bromo-3-phenylpropane, there are obtained the 2-(2-methylphenyl)-1-ethenyl, 2-(4-ethylphenyl)-1-ethenyl, 2-(4-chlorophenyl)-1-ethenyl, 2-[3-(trifluoromethyl)phenyl]-1-ethenyl, 3-(4-fluoro-phenyl)-1-propenyl, 6-(2-chlorophenyl)-1-hexenyl, 4-(3,4-dimethoxyphenyl)-1-butenyl, and 7-(2,4,6-trimethylphenyl)-1-heptenyl compounds corresponding to the products of Examples 1 and 2.

Also following the procedures of Example 1, but using quaternary triphenyl phosphonium halides prepared from other primary and secondary halides of the formula

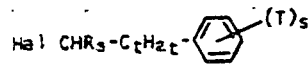

wherein Hal, R$_3$, -C$_t$H$_{2t}$-, T and s are defined above in place of 1-bromo-3-phenylpropane, there are obtained compounds corresponding to the products of Example 1 with

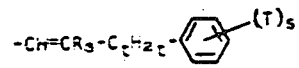

in place of the 4-phenyl-1-butenyl moiety.

Also following the procedure of Example 1, but using bicyclo[3.1.0]hexane reactants with

in place of

wherein R$_4$ is as defined above, there are obtained compounds corresponding to the products of Example 1 with

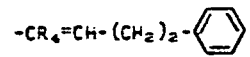

in place of the 4-phenyl-1-butenyl moiety.

Also following the procedures of Examples 1 and 2 but using exo-biocyclo[3.1.0]hexane reactants in place of each of the endo reactants defined in Examples 1 and 2 and above, the exo products are obtained corresponding to the endo products of Examples 1 and 2 and above.

By the above-described procedures, each of the reactants encompassed by Formula L, above, is prepared.

Example 3

Ethyl 7-[Endo-6-(cis-4-phenyl-1-butenyl)-3-oxobicyclo[3.1.0]hex-2α-yl]-3-oxaheptanoate (Formula LI: Q is

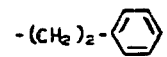

R$_2$, R$_3$, and R$_4$ are hydrogen; R$_{10}$ is ethyl; Z is -(CH$_2$)$_3$-O-CH$_2$-; and ~ is endo and alpha).

To a solution of endo-6-(cis-4-phenyl-1-butenyl)-bicyclo[3.1.0]hexan-3-one (11.3 g.), ethyl 7-iodo-3-oxaheptanoate (41 g.), and dicyclohexyl-18-crown-6 [J. Am. Chem. Soc. 89, 7017 (1967)], (4.6 g.) in 270 ml. of tetrahydrofuran freshly distilled from lithium aluminum hydride is added, at room temperature with stirring under nitrogen, a solution of potassium t-butoxide (6.7 g.) in 550 ml. of tetrahydrofuran (treated as above) over a period of 50 min. Three minutes after the addition of the butoxide solution is completed, 50 ml.

of 5% aqueous hydrochloric acid is added, then 5 ml. of pyridine. The mixture is then concentrated under reduced pressure by heating it in a water bath at 35°C. until most of the tetrahydrofuran is removed. The aqueous residue is extracted with dichloromethane and the extract is washed with ice-cold dilute hydrochloric acid, water, dilute aqueous sodium thiosulfate, and brine, then dried over sodium sulfate and concentrated under reduced pressure to give an oil. The oil is dissolved in 100 ml. of ethyl acetate-cyclohexane (10:90) and chromatographed over 2 kg. of silica gel wet-packed in ethyl acetate-cyclohexane (10:90), eluting with 8 l. of 10% and 7 l. of 20% ethyl acetate in cyclohexane, taking 200-ml. fractions. Fractions 50-65 are evaporated under reduced pressure to give 7.2 g. of the desired ethyl 7-[endo-6-(cis-4-phenyl-1-butenyl)- 3-oxobicyclo[3.1.0]hex-2α-yl]-3-oxaheptanoate; mass spectral peaks at 384, 342 and 293.

Following the procedure of Example 3 but using a larger amount of potassium tert-butoxide (16 g.) and maintaining the reaction mixture for 8 hours at 25°C. before addition of hydrochloric acid, a product is obtained which contains substantial amounts of both the above-described 2α-yl isomer and the corresponding 2β-yl isomer. These isomers are separated by the above-described silica gel chromatography.

EXAMPLE 4

Ethyl 2,2-Dimethyl-7-[exo-6-(cis-4-phenyl-1-butenyl)-3-oxobicyclo[3.1.0]hex-2α-yl]-3-oxaheptanoate (Formula LI: Q is

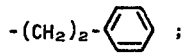 ;

$R_2$, $R_3$, and $R_4$ are hydrogen; $R_{10}$ is ethyl; Z is —$(CH_2)_s$—O—$C(CH_3)_2$—; ∼ is endo and alpha).

Following the procedures of Example 3 but substituting ethyl 2,2-dimethyl-7-iodo-3-oxaheptanoate for ethyl 7-iodo-3-oxaheptanoate, and substituting exo-6-(cis-4-phenyl-1-butenyl)-bicyclo[3.1.0]hexan-3-one for endo-6-(cis-4-phenyl-1-butenyl)-bicyclo[3.1.0]hexan-3-one, and substituting ethyl acetate for dichloromethane, there are obtained ethyl 2,2-dimethyl 7-[exo-6-(cis-4-phenyl-1-butenyl)-3-oxobicyclo[3.1.0]hex-2α-yl]-3-oxaheptanoate and the corresponding -2β-yl isomer.

Following the procedures of Examples 3 and 4, but using in place of the bicyclo[3.1.0]hexane reactant, each of endo and exo forms of the various Formula-L bicyclo[3.1.0]hexane reactants whose preparation is described following Example 2, for example, Formula-L bicyclo compounds wherein Q, $R_3$, $R_4$, and ∼ are as defined above, those being prepared as described above, there are obtained alpha and beta exo and endo Formula-LI compounds corresponding to the products of Example 3 with one of these Q moieties in place of the

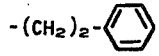

moiety (the Q portion of those products). Accordingly, using Formula-L bicyclo compounds wherein —$C_tH_{2t}$— represents alkylene substituted with oe or 2 fluoro, for example the bicyclo compound prepared by the procedures of Preparation 5 and Example 1 from (2-bromo-1-fluoroethyl)benzene, (5-bromo-4-fluoropentyl)benzene, and (6-bromo-5,5-difluorohexyl)benzene there are obtained Formula-LI compounds corresponding to the products of Examples 3 and 4 wherein —$C_tH_{2t}$— represents alkylene substituted with one or 2 fluoro. Accordingly, using the Formula-L bicyclo compounds wherein $(T)_s$ on the phenyl ring is alkyl of one to 4 carbon atoms, inclusive, fluoro, chloro, trifluoromethyl, or $OR_9$ wherein $R_9$ is hydrogen, alkyl of one to 4 carbon atoms, inclusive, or tetrahydropyranyl, and $s$ is one, 2, or 3, for example Formula-L bicyclo compounds wherein $(T)_s$ is 2-methyl, 2,4,6-trimethyl,2-chloro,3-trifluoromethyl, or 3,4-dimethoxy, there are obtained Formula-LI compounds corresponding to the products of Examples 3 and 4. As for Example 3, with excess base and a longer reaction time, these alternative products contain substantial amounts of the corresponding beta isomer which is separated from the alpha isomer as described above.

Also following the procedure of Examples 3 and 4, but using in place of the iodo alkylating agents of those Examples, ethyl 7-iodo-4-oxaheptanoate, ethyl 7-iodo-3-oxa-5-heptynoate, and ethyl 8-iodo-4-oxa-6-octynoate, there are obtained alpha and beta exo and endo Formula-LI compounds corresponding to the products of Examples 3 and 4 with —$(CH_2)_3OCH_2CH_2COOEt$, —$CH_2C \equiv CCH_2OCH_2COOEt$, and —$CH_2C \equiv CC-H_2OCH_2CH_2COOEt$, respectively, wherein Et is ethyl, in place of the —$(CH_2)_4OCH_2COOEt$ and —$CH_2$-$)_4OC(CH_3)_2COOEt$ moieties of the products of Examples 3 and 4. As described above, both alpha and beta products are so obtained. In the same manner but using, according to Examples 3 and 4, other esters of the Examples 3 and 4 alkylating agents and of the other above-mentioned alkylating agents within the scope of $R_{10}$ as above-defined, e.g., the methyl, isopropyl, tert-butyl, octyl, cyclohexyl, benzyl, and phenyl esters, there are obtained the corresponding esters of the alpha and beta bicyclo[3.1.0]hexane alkylation products.

Also following the procedure of Examples 3 and 4 but using in combination each of the above-described alternative Formula-L bicyclo[3.1.0]hexane reactants and each of the above-described alternative omega-halo alkylation reactants, there are obtained Formula-LI compounds corresponding to the products of Examples 3 and 4 but different therefrom with respect to both the carboxylate-terminated side chain and the side chain attached to the cyclopropane ring of the product.

Also following the procedure of Examples 3 and 4, but using in place of the iodo alkylating agents of those Examples, each of the other alkylating agents within the scope of

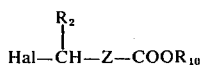

as above defined, i.e., alkylating agents of Formulas LX, LXI, LXII, and LXIII as above-described, there are obtained alpha and beta exo and endo Formula-LI compounds corresponding to the products of Examples 3 and 4 with each of the other

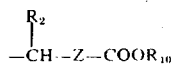

side chains in place of the —(CH$_2$)$_4$OCH$_2$COOEt and —(CH$_2$)$_4$OC(CH$_3$)$_2$COOEt side chains of the Examples 3 and 4 products. For example, using as alkylating agents in the Example 3 and 4 procedure, I(CH$_2$)$_4$OCH(CH$_3$)COOEt, ICH(CH$_3$)—(CH$_2$)$_3$OCH$_2$COOEt, I(CH$_2$)$_3$OCH$_2$COOEt, I(CH$_2$)$_5$OCH$_2$COOEt, ICH$_2$CH(CH$_3$)CH$_2$CH$_2$OCH$_2$COOEt, ICH$_2$CH$_2$C(CH$_2$CH$_3$)$_2$CH$_2$OCH$_2$COOEt, I(CH$_2$)$_3$C(CH$_3$)$_2$OCH$_2$COOEt, I(CH$_2$)$_3$OCH$_2$CH$_2$COOEt, I(CH$_2$)$_2$OCH$_2$CH$_2$COOEt, I(CH$_2$)$_4$OCH$_2$CH$_2$COOEt, I(CH$_2$)$_3$OCH(CH$_3$)CH$_2$COOEt, I(CH$_2$)$_3$OC(CH$_3$)$_2$CH$_2$COOEt, I(CH$_2$)$_3$OCH$_2$C(CH$_3$)$_2$COOEt, ICH(CH$_3$)CH$_2$CH$_2$OCH$_2$CH$_2$COOEt, ICH$_2$CH(CH$_3$)CH$_2$OCH$_2$CH$_2$COOEt, ICH$_2$CH$_2$C(CH$_3$)$_2$OCH$_2$CH$_2$COOEt, ICH$_2$C(CH$_2$CH$_3$)$_2$CH$_2$OCH$_2$CH$_2$COOEt, ICH$_2$C≡CCH$_2$OCH$_2$COOEt, ICH(CH$_3$)C≡CCH$_2$OCH$_2$COOEt, ICH$_2$C≡CCH$_2$CH$_2$OCH$_2$COOEt, ICH$_2$C≡CCH$_2$OCH(CH$_3$)COOEt, ICH$_2$C≡CCH$_2$OC(CH$_3$)$_2$COOEt, ICH$_2$C≡CCH(CH$_3$)OCH$_2$COOEt, ICH$_2$C≡CC(CH$_3$)$_2$OCH$_2$COOEt, ICH$_2$C≡C-CH$_2$OCH$_2$CH$_2$COOEt, ICH(CH$_3$)C≡CCH$_2$OCH$_2$CH$_2$COOEt, ICH$_2$C≡CCH$_2$CH$_2$OCH$_2$CH$_2$COOEt, ICH$_2$C≡CCH$_2$OCH(CH$_3$)CH$_2$COOEt, ICH$_2$C≡CCH$_2$OC(CH$_3$)$_2$CH$_2$COOEt, ICH$_2$C≡CCH(CH$_3$)$_2$CH$_2$COOEt, ICH$_2$C≡CCH(CH$_3$)OCH$_2$CH$_2$COOEt, ICH$_2$C≡CC(CH$_3$)$_2$OCH$_2$CH$_2$COOEt, ICH$_2$C≡CCH$_2$OCH$_2$C(CH$_3$)$_2$COOEt there are obtained exo and endo alpha and beta alkylated bicyclo[3.1.0]hexanes each having a carboxylate-terminated side chain corresponding to one of the above specific omega-iodo alkylating agents. For example, the side chain will be alpha or beta —(CH$_2$)$_4$OCH(CH$_3$)COOEt when the alkylating agent is I(CH$_2$)$_4$OCH(CH$_3$)COOEt.

Also following the procedure of Examples 3 and 4, but using in combination each of the alternative alkylating agents within the scope of

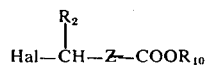

including the specific examples of those just mentioned, and each of the above-described Formula-L alternative bicyclo[3.1.0]hexane reactants, there are obtained Formula-LI exo and endo alpha and beta compounds corresponding to the products of Examples 3 and 4 but different therefrom with respect to both the carboxylate-terminated side chain and the side chain attached to the cyclopropane ring of the product. In the same manner, alternative alkylating agents within the scope of

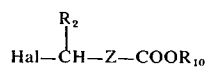

wherein R$_{10}$ is other than ethyl, e.g., methyl, isopropyl, tert-butyl, octyl, cyclohexyl, benzyl, phenyl, and β, β, β-trichloroethyl are used.

EXAMPLE 5

Ethyl 7-[Endo-6-(1,2-dihydroxy-4-phenylbutyl)-3-oxobicyclo[3.1.0]hex-2α-yl]-3-oxaheptanoate (Formula LII: Q is

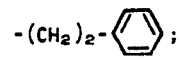

R$_2$, R$_3$, and R$_4$ are hydrogen; R$_{10}$ is ethyl; Z is —(CH$_2$)$_3$—O—CH$_2$—; and ~ is endo and alpha.

A solution of potassium chlorate (12.4 g.) in 150 ml. of water is added to a solution of ethyl 7-[endo-6-(cis-4-phenyl-1-butenyl)-3-oxobicyclo[3.1.0]hex-2αyl]-3-oxaheptanoate (15.9 g.) in 365 ml. of tetrahydrofuran at 50°C., then 0.73 g. of osmium tetroxide is added and the mixture is stirred at 50°C. for 2.25 hours., then concentrated under reduced pressure until most of the tetrahydrofuran is removed. The aqueous residue is extracted with dichloromethane and the extract is washed with water and then brine, dried over sodium sulfate, and concentrated under reduced pressure to give an oil. The oil is chromatographed over 2 kg. of silica gel wet-packed with ethyl acetate-cyclohexane (1:1 vol/vol), eluting with 6 l. of 2:1 and 4 l. of 3:1 ethyl acetate-cyclohexane and 5.6 l. of ethyl acetate, taking 200 ml. eluate fractions, then one 1000 ml. ethyl acetate fraction. Fractions 48-78 plus the 1000 ml. fraction are concentrate under reduced pressure to give 12.5 g. of the desired ethyl 7-[endo-6-(1,2-dihydroxy-4-phenylbutyl)-3-oxo-bicyclo[3.1.0]-hex-2α-yl]-3-oxaheptanoate as a mixture of erythro and threo glycols; mass spectral peaks at 418, 400 and 283; NMR peaks at 7.22, 4.37–4.02, 3.61–3.39, 3.08–2.59, 2.33, 1.66–1.42, and 1.36–1.13 δ.

Following the procedure of Example 5 but using the hex-2β-yl isomer in place of the hex-2α-yl isomer of the bicyclo reactant ethyl 7-[endo-6-(1,2-dihydroxy-4-phenylbutyl)-3-oxo-bicyclo[3.1.0]hex-2β-yl]-3-oxaheptanoate is obtained.

Also following the procedure of Example 5, each of the Formula-LI exo and endo, alpha and beta, saturated and acetylenic bicyclo[3.1.0]hexane olefinic esters defined above after Examples 3 and 4 is oxidized to mixtures of the corresponding isomeric Formula-LII dihydroxy compounds.

EXAMPLE 6 dl-3-Oxa-17-phenyl-18,19,20-trinor-PGE$_1$ Ethyl Ester, and dl-15-Epi-3-oxa-17-phenyl-18,19,20-trinor-PGE$_1$, Ethyl Ester (Formula XI: C$_n$H$_{2n}$ is —(CH$_2$)$_3$—; C$_t$H$_{2t}$ is ethylene; R$_1$ is ethyl; R$_2$, R$_3$, R$_4$, R$_5$, and R$_6$ are hydrogen; s is zero; and ~ is alpha).

The steps shown in Chart F are followed. A solution of ethyl 7-[endo-6-(1,2-dihydroxy-4-phenylbutyl)-3-oxobicyclo[3.1.0]hex-2α-yl]-3-oxaheptanoate (mixture of isomeric glycols) (12.4 g.) in 150 ml. of dry pyridine is cooled to −5°C. and to it is added 15 ml. of methanesulfonyl chloride at such a rate that the reaction temperature does not exceed 0°C. The mixture is stirred for 2.5 hours at 0°C. following addition of the methanesulfonyl chloride. Then water is added dropwise, with continued cooling to keep the temperature below 5°C., to decompose excess methanesulfonyl chloride. The mixture is diluted with 300 ml. of ice water and extracted with dichloromethane. The extract is washed successively with ice-cold dilute hydrochloride acid, dilute aqueous sodium bicarbonate, and brine, then dried over sodium sulfate and evaporated under reduced pressure to give an oil. The oil is dissolved in 50 ml. of 3:1 (vol./vol.) ethyl acetate-cyclohexane and chromatographed over 1.5 kg. of silica gel wet-packed in 3:1 ethyl acetate-cyclohexane, eluting with 1.5 l. of 3:1 ethyl acetate-cyclohexane, 3 l. of ethyl acetate, 3 l. of 2%, 2.4 l. of 5% and 2 l. of 10% ethyl alcohol in ethyl acetate, taking 150-ml. fractions. Fractions 46-63 are evaporated under reduced pressure to give 1.6 g. of the desired dl-15-epi-3-oxa-17-phenyl-18,19,20-trinor-PGE$_1$ ethyl ester; mass spectral peaks at 400 and 382. NMR peaks at 7.22, 5.78–5.63, 4.35–3.99 (multiplet), 3.62–3.37, 2.97–2.60 (multiplet), 1.66–1.42, 1.36–1.13 (multiplet) δ.

Fractions 58–68 (5% ethyl alcohol in ethyl acetate) and the 10% ethyl alcohol fractions are combined and evaporated to give dl-3-oxa-17-phenyl-18,19,20-trinor-PGE$_1$ ethyl ester mixed with the 15-epi isomer. This is rechromatographed as above to give 1.41 g. of the desired dl-3-oxa-17-phenyl-18,19,20-trinor-PGE$_1$ ethyl ester; mass spectral peaks at 400 and 382. NMR peaks at 7.22, 5.73–5.56, 4.35–4.02 (multiplet), 3.53–3.33, 2.82–2.39 (multiplet), 2.03–1.76 (multiplet), 1.66–1.42, and 1.36–1.13 (multiplet) δ.

Following the procedures of Example 6, each of the Formula-LII endo-1,2-dihydroxy-3-oxa esters and endo-1,2-dihydroxy-4-oxa esters following Example 5 is transformed to the corresponding endo-1,2-dimesyloxy-3(or -4)-oxa ester, and thence to the corresponding PGE type compound or its isomers.

Also following the procedures of Example 6, each of the Formula-LII exo-1,2-dihydroxy-3-(or -4)-oxa esters corresponding to the above endo-1,2-dihydroxy-3(or -4)-oxa esters is transformed to the corresponding exo-1,2-dimesyloxy-3(or -4)-oxa ester, and thence to the corresponding PGE type compound or its isomers.

By the above-outlined procedures, following the steps of Chart F, there are obtained the specific PGE type esters represented by FIGS. XI, XII, XV, and XVI, e.g. the esters of 3-oxa (or 4-oxa)-17-phenyl-18,19,20-trinor-PGE$_1$;
3-oxa (or 4-oxa)-18-phenyl-18,19,20-dinor-PGE$_1$;
5,6-dehydro-3-oxa (or 4-oxa)-17-phenyl-18,19,20-trinor-PGE$_2$;
5,6-dehydro-3-oxa (or 4-oxa)-18-phenyl-19,20-dinor-PGE$_2$; including their 8-iso and 15-epi forms.

For example, β,β,β-trichloroethyl 2,2,3,3-tetramethyl-7-[endo-6-(3-fluoro-3-phenyl-1-propenyl)-3-oxo-bicyclo[3.1.0]-hex-2α-yl]-7-methyl-4-oxaheptanoate yields β,β,β-trichloroethyl 2,2,3,3-tetramethyl-7-[endo-6-(3-fluoro-1,2-dihydroxy-3-phenyl-propyl)-3-oxo-bicyclo[3.1.0]hex-2α-yl]-4-oxa-heptanoate in its isomeric forms, and thence the corresponding bis(mesylate) and thence the corresponding PGE$_1$ type compound and its 15-epimer, as represented by the following formulas:

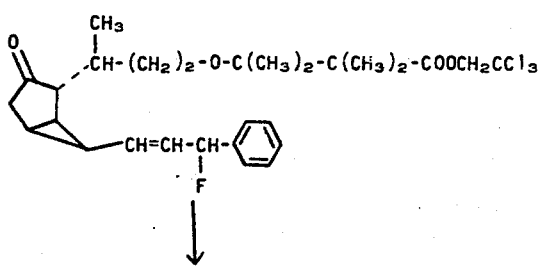

Likewise, methyl 2,2-dimethyl-7-{exo-6-[1,2-dimethyl-5-(4-methoxyphenyl)-1-pentenyl]-3-oxo-bicyclo[3.1.0]hex-2β-yl}-3-oxa-5-heptynoate yields methyl 2,2-dimethyl-7-{exo-6-[1,2-dihydroxy-5-(4-methoxyphenyl)-1-pentane]-3-oxo-bicyclo[3.1.0]hex-2β-yl}-3-oxa-5-heptynoate in its isomeric forms, and thence the corresponding bis(mesylate) and thence the corresponding dehydro-PGE$_2$ type compound and its 15-epimers, as represented by the following formulas:

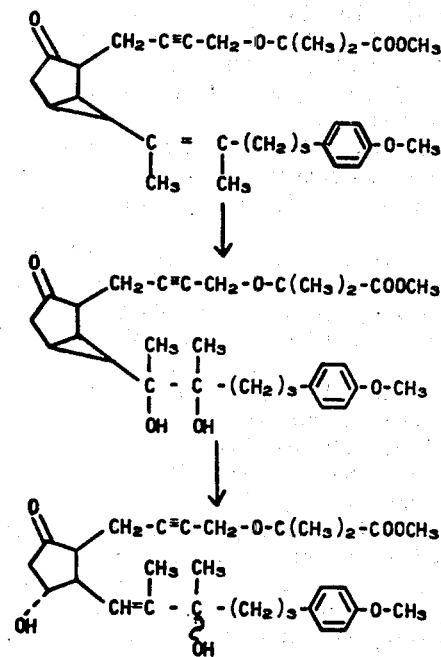

Also following the procedure of Example 6, but replacing methanesulfonyl chloride with an alkanesulfonyl chloride or bromide or with an alkanesulfonic acid anhydride, wherein the alkane moiety contains 2 to 5 carbon atoms, inclusive, there is obtained from each dihydroxy compound the corresponding bis(sulfonic acid) esters encompassed by Formula LIII.

In each of the above transformations in Example 6, the monosulfonic acid ester is also obtained as a by-

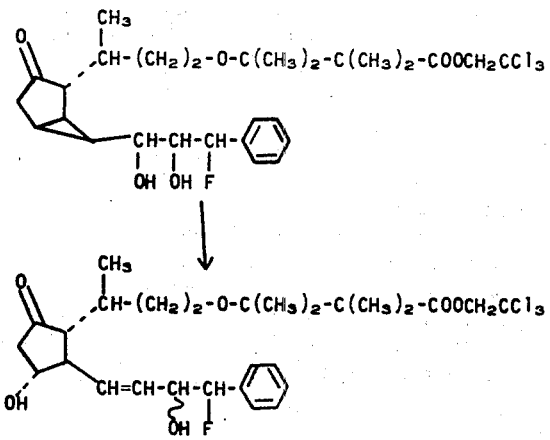

product, which is reacted with additional alkanesulfonyl halide or alkanesulfonic acid anhydride to give the corresponding bis(sulfonic acid) ester and thence recycled back to additional Formula-LIV product.

For satisfactory yields of the bis-sulfonic acid ester, $R_{10}$ is not hydrogen. Those intermediate compounds in which $R_{10}$ is haloethyl, e.g., $\beta,\beta,\beta$-trichloroethyl, are especially useful in the sequence of reactions leading to the acid form of the prostaglandin-like products. Each of the exo and endo, alpha and beta, saturated and unsaturated 3-oxa or 4-oxa phenyl-substituted bis(alkanesulfonic acid) esters is transformed to the corresponding 3-oxa or 4-oxa phenyl-substituted PGE type compound corresponding by Formula LIV.

Example 7 dl-3-Oxa-17-phenyl-18,19,20-trinor-PGE$_1$ (Formula XI: $C_nH_{2n}$ is —$(CH_2)_3$—; $C_tH_{2t}$ is ethylene; $R_1$, $R_2$, $R_3$, $R_4$, $R_5$, and $R_6$ are hydrogen; s is zero; and $\sim$ is alpha).

Zinc dust (420 mg.) is added to a solution containing 3-oxa-17-phenyl-18,19,20-trinor-PGE$_1$ $\beta,\beta,\beta$-trichloroethyl ester (100 mg.) in 5 ml. of a mixture of acetic acid and water (9:1 v/v). This mixture is stirred under nitrogen 2 hours at 25° C. Ethyl acetate (4 volumes) is then added, followed by addition of one normal hydrochloric acid (one volume). The ethyl acetate layer is separated, washed with water and then with saturated aqueous sodium chloride solution, dried, and evaporated. The residue is chromatographed on 15 g. of acid-washed silica gel (Silicar CC4), being eluted with 100 ml. of 50%, 100 ml. of 80%, and 200 ml. of 100% ethyl acetate in Skellysolve B, collecting 20-ml. fractions. The fractions containing dl-3-oxa-17-phenyl-18,19,20-trinor-PGE$_1$ and no starting material or dehydration products as shown by TLC are combined and evaporated to give dl-3-oxa-17-phenyl-18,19,20-trinor-PGE$_1$.

Following the procedure of Example 7, each of the $\beta,\beta,\beta$-tribromoethyl, -triiodoethyl, $\beta,\beta$-dibromoethyl, -diiodoethyl, and the $\beta$-iodoethyl esters of 3-oxa-17-phenyl-18,19,20-trinor-PGE$_1$ is converted to the free acid of 3-oxa-17-phenyl-18,19,20-trinor-PGE$_1$ by reaction with zinc dust and acetic acid. Likewise, the corresponding 4-oxa compounds are converted to 4-oxa-17-phenyl-18,19,20-trinor-PGE$_1$.

Following the procedure of Example 7, the $\beta,\beta,\beta$-trichloroethyl ester of 3-oxa-18-phenyl-19,20-dinor-PGE$_2$ following Example 23 below is converted to the respective free acid compound using zinc dust with either propionic, butyric, pentanoic, or hexanoic acid instead of acetic acid. Likewise the corresponding 4-oxa compounds are converted to 4-oxa-18-phenyl-19,20-dinor-PGE$_2$.

Following the procedure of Example 7, the $\beta,\beta,\beta$-trichloroethyl ester of each of the PGE, PGA and PGB type compounds represented by Formulas XI-XLII in their various structural configurations and optical isomers is treated with zinc dust and acetic acid to obtain the corresponding free acid form of the compound. The esters are prepared by the procedures disclosed herein, using as intermediates Formula-XLIV cyclic ketals or Formula-LI olefins wherein $R_{10}$ is haloethyl, e.g., $\beta,\beta,\beta$-trichloroethyl. These intermediates are prepared either by alkylation of the respective Formula-XLIII cyclic ketal (Chart E) or Formula-L olefin (Chart F) with the appropriate alkylating agent wherein $R_{10}$ is haloethyl, or by the transformation of the alkylated cyclic ketal or olefin by the steps shown in Charts G and H using procedures disclosed herein, yielding intermediates LXXI, LXXIII, LXXVII, or LXXXIX.

EXAMPLE 8 dl-3-Oxa-17-phenyl-18,19,20-trinor-PGF$_{1\alpha}$ Ethyl Ester and dl-3-Oxa-17-phenyl-18,19,20-trinor-PGF$_{1\beta}$ Ethyl Ester (Formula XIX: $C_nH_{2n}$ is —$(CH_2)_3$—; $C_tH_{2t}$ is ethylene; $R_1$ is ethyl; $R_2$, $R_3$, $R_4$, $R_5$, and $R_6$ are hydrogen; s is zero; and $\sim$ is alpha or beta).

A solution of sodium borohydride (300 mg.) in 6 ml. of ice-cold methanol is added to a solution of dl-3-oxa-17-phenyl-18,19,20-trinor-PGE$_1$ ethyl ester (650 mg.) in 30 ml. of methanol at $-5°$ C. the mixture is stirred for 0.5 hours at 0° C. and 5 ml. of acetone is added, after which the mixture is stirred for 5 minutes and made slightly acid with acetic acid. The mixture is evaporated under reduced pressure until most of the methanol and acetone are removed, then the residue is extracted with dichloromethane. The extract is washed with water, dilute aqueous sodium bicarbonate, and brine, then dried over sodium sulfate and evaporated under reduced pressure to give a residue (690 mg.). This residue is chromatographed over 105 g. of silica gel wet-packed in ethyl acetate, eluting with 750 ml. of 2%, 500 ml. of 4%, 625 ml. of 7.5% and 875 ml. of 10% ethanol in ethyl acetate, taking 25 ml. fractions. Fractions 54–71 are evaporated to a residue, which is recrystallized from ether-pentane to give 140 mg. of the desired dl-3-oxa-17-phenyl-18,19,20-trinor-PGF$_{1\beta}$ ethyl ester, m.p. 76°–80° C.; mass spectral peaks at 402, 384, and 366; NMR peaks at 7.22, 5.63–5.41, 4.35–3.97 (multiplet), 3.70, 3.49–3.30, 2.78–2.53 (multiplet), 1.66–1.42, and 1.36–1.13 (multiplet) δ.

Fractions 26–53 are evaporated under reduced pressure and the residue is rechromatographed as above to give 139 mg. of the desired dl-3-oxa-17-phenyl-18,19,20-trinor-PGF$_{1\beta}$ ethyl ester as an oil; mass spectral peaks at 420, 402, 384 and 366; NMR peaks at 7.22, 5.60–5.42, 4.35–3.97 (multiplet), 3.70, 3.49–3.23, 2.80–2.53 (multiplet), 1.66–1.42, and 1.36–1.13 (multiplet) δ.

Following the procedure of Example 8, 4-oxa-17-phenyl-18,19,20-trinor-PGE$_1$ ethyl ester is transformed to 4-oxa-17-phenyl-18,19,20-trinor-PGF$_{1\alpha}$ and -PGF$_{1\beta}$ ethyl esters. Likewise, 3-oxa-18-phenyl-19,20-dinor-PGE$_1$ ethyl ester and 4-oxa-18-phenyl-19,20-dinor-PGE$_1$ ethyl ester are transformed to the corresponding PGF$_{1\alpha}$ and PGF$_{1\beta}$ type ethyl esters.

EXAMPLE 9 dl-3-Oxa-17-phenyl-18,19,20-trinor-PGF$_{1\alpha}$ and dl-3-Oxa-17-phenyl-18,19,20-trinor-PGF$_{1\beta}$ (Formula XIX: $C_nH_{2n}$ is —$(CH_2)_3$—; $C_tH_{2t}$ is ethylene; $R_1$, $R_2$, $R_3$, $R_4$, $R_5$, and $R_6$ are hydrogen; s is zero; and $\sim$ is alpha or beta).

A solution of 146 mg. of dl-3-oxa-17-phenyl-18,19,20-trinor-PGF$_{1\alpha}$ ethyl ester in a mixture of 4.5 ml. of methanol and 1.5 ml. of water is cooled to 5° C. and 0.6 ml. of 45% aqueous potassium hydroxide is added. The mixture is allowed to stand 3.5 hours at 25° C., then is diluted with 75 ml. of water and extracted once with ethyl acetate to remove any neutral material. The aqueous layer is separated, made acid with dilute hydrochloric acid and extracted 4 times with ethyl acetate. The extracts are combined and washed 3 times with water, once with brine, dried over sodium sulfate, and evaporated to give dl-3-oxa-17-phenyl-18,19,20-trinor-PGF$_{1\alpha}$.

A solution of 251 mg. of dl-3-oxa-17-phenyl-18,19,20-trinor-PGF$_{1\beta}$ methyl ester in a mixture of 7.5 ml. of methanol and 2.5 ml. of water is cooled to 5° C. and 1.0 ml. of 45% aqueous potassium hydroxide is added. The mixture is allowed to stand 2.5 hours at 25° C. and is diluted with water and extracted with ethyl acetate to remove neutral material. The aqueous layer is made acid with dilute hydrochloric acid and extracted with ethyl acetate. The ethyl acetate extracts are washed with water, and brine, dried over sodium sulfate and evaporated to give dl-3-oxa-17-phenyl-18,19,20-trinor-PGF$_{1\beta}$.

Following the procedures of Example 9, the corresponding 4-oxa methyl or ethyl esters are transformed to dl-4-oxa-17-phenyl-18,19,20-trinor-PGF$_{1\alpha}$ and -PGF$_{1\beta}$. Likewise the 3-oxa (or 4-oxa)-18-phenyl-19,20-dinor-PGF$_{1\beta}$ ethyl esters are transformed to the dl-3-oxa (or -4-oxa)-18-phenyl-19,20-dinor-PGF$_{1\alpha}$ and -PGF$_{1\beta}$.

EXAMPLE 10 dl-15-Epi-3-oxa-17-phenyl-18,19,20-trinor-PGF$_{1\alpha}$ Ethyl Ester and
dl-15-Epi-3-oxa-17-phenyl-18,19,20-trinor-PGF$_{1\beta}$ Ethyl Ester (Formula XIX: C$_n$H$_{2n}$ is —(CH$_2$)$_3$—; C$_t$H$_{2t}$ is ethylene; R$_1$ is ethyl; R$_2$, R$_3$, R$_4$, R$_5$, and R$_6$ are hydrogen; $s$ is zero; and ~ is alpha or beta).

A solution of dl-15-epi-3-oxa-17-phenyl-18,19,20-trinor-PGE$_1$ ethyl ester (650 mg.), hexamethyl disilazane (5 ml.) and trimethylchlorosilane (1 ml.) in 25 ml. of tetrahydrofuran is allowed to stand for 20 hours at about 25° C. The mixture is concentrated under reduced pressure to give the 11,15-bis(trimethylsilyl)ether of dl-15-epi-3-oxa-17-phenyl-18,19,20-trinor-PGE$_1$ ethyl ester as a viscous oil. This ether is dissolved in 135 ml. of methanol, cooled to −5° C., and a solution of sodium borohydride (0.5 g.) in 25 ml. of ice-cold methanol is added. The mixture is allowed to stand 30 minutes at 0° C., then 10 ml. of acetone is added, and the mixture is made slightly acidic with acetic acid. This mixture is stirred at about 25° C. for 3 hours, then concentrated under reduced pressure to remove the methanol and acetone. The aqueous residue is extracted with ethyl acetate and the extract is washed with water and brine, dried over sodium sulfate, and evaporated under reduced pressure to give a residue. This residue is chromatographed over 140 g. of silica gel wet-packed in ethyl acetate, eluting with 150 ml. of 3%, 450 ml. of 5%, and 450 ml. of 7.5% ethanol in ethyl acetate, taking 15-ml. fractions. Fractions 29–41 are evaporated to give 344 mg. of dl-15-epi-3-oxa-17-phenyl-18,19,20-trinor-PGF$_{1\alpha}$ ethyl ester; mass spectral peaks at 420, 402, 384 and 330.

Fractions 54–65 are evaporated to give 86 mg. of dl-15-epi-3-oxa-17-phenyl-18,19,20-trinor-PGF$_{1\beta}$ ethyl ester.

Also following the procedures of Examples 8 and 10, the methyl ester and free acid forms of Formula XIX-to-XXVI PGF compounds in their various spatial configurations, e.g., 8-iso-3-oxa (or 4-oxa)-17-phenyl-18,19,20-trinor-PGF$_{1\alpha}$ and -PGF$_{1\beta}$, 8-iso-15-epi-3-oxa (or 4-oxa)-17-phenyl-18,19,20trinor-PGF$_{1\alpha}$ and -PGF$_{1\beta}$, 3-oxa (or 4-oxa)-17-phenyl-18,19,20-trinor-PGF$_{2\alpha}$ and -PGF$_{2\beta}$, 15-epi-3-oxa (or 4-oxa)-17-phenyl-18,19,20-trinor-PGF$_{2\alpha}$ and -PGF$_{2\beta}$, 8-iso-3-oxa (or 4-oxa)-17-phenyl-18,19,20-trinor-PGF$_{2\alpha}$ and -PGF$_{2\beta}$, 8-iso-15-epi-3-oxa (or 4-oxa)-17-phenyl-18,19,20-trinor-PGF$_{2\alpha}$ and -PGF$_{2\beta}$, trans-5,6-dehydro-3-oxa (or 4-oxa)-17-phenyl-18,19,20-trinor-PGF$_{1\alpha}$ and -PGF$_{1\beta}$, trans-5,6-dehydro-15-epi-3-oxa (or 4-oxa)-17-phenyl-18,19,20-trinor-PGF$_{1\alpha}$ and -PGF$_{1\beta}$, trans-5,6-dehydro-8-iso-3-oxa (or 4-oxa)-17-phenyl-18,19,20-trinor-PGF$_{1\alpha}$ and -PGF$_{1\beta}$, trans-5,6-dehydro-8-iso-15-epi-3-oxa (or 4-oxa)-17-phenyl-18,19,20-trinor-PGF$_{1\alpha}$ and -PGF$_{1\beta}$, 5,6-dehydro-3-oxa (or 4-oxa)-17-phenyl-18,19,20-trinor-PGF$_{2\alpha}$ and PGF$_{2\beta}$, 5,6-dehydro-15-epi-3-oxa (or 4-oxa)-17-phenyl-18,19,20-trinor-PGF$_{2\alpha}$ and -PGF$_{2\beta}$, 5,6-dehydro-8-iso-3-oxa (or 4-oxa)-17-phenyl-18,19,20-trinor-PGF$_{2\alpha}$ and -PGF$_{2\beta}$, 5,6-dehydro-8-iso-15-epi-3-oxa (or 4-oxa)-17-phenyl-18,19,20-trinor-PGF$_{2\alpha}$ and -PGF$_{2\beta}$, 13,14-dihydro-3-oxa (or 4-oxa)-17-phenyl-18,19,20-trinor-PGF$_{1\alpha}$ and -PGF$_{1\beta}$, 13,14-dihydro-15-epi-3-oxa (or 4-oxa)-17-phenyl-18,19,20-trinor-PGF$_{1\alpha}$ and -PGF$_{1\beta}$, 13,14-dihydro-8-iso-3-oxa (or 4-oxa)-17-phenyl-18,19,20-trinor-PGF$_{1\alpha}$ and -PGF$_{1\beta}$, 13,14-dihydro-8-iso-15-epi-3-oxa (or 4-oxa)-17-phenyl-18,19,20-trinor-PGF$_{1\alpha}$ and -PGF$_{1\beta}$, 15-epi-3-oxa (or 4-oxa)-18-phenyl-19,20-dinor-PGF$_{1\alpha}$ and -PGF$_{1\beta}$, 8-iso-3-oxa (or 4-oxa)-18-phenyl-19,20-dinor-PGF$_{1\alpha}$ and -PGF$_{1\beta}$, 8-iso-15-epi-3-oxa (or 4-oxa)-18-phenyl-19,20-dinor-PGF$_{2\alpha}$ and -PGF$_{2\beta}$, trans-5,6-dehydro-3-oxa (or 4-oxa)-18-phenyl-19,20-dinor-PGF$_{1\alpha}$ and -PGF$_{1\beta}$, trans-5,6-dehydro-15-epi-3-oxa (or 4oxa)-18-phenyl-19,20-dinor-PGF$_{1\alpha}$ and -PGF$_{1\beta}$, trans-5,6-dehydro-8-iso-3-oxa (or 4-oxa)-18-phenyl-19,20-dinor-PGF$_{1\alpha}$ and -PGF$_{1\beta}$, trans-5,6-dehydro-8-iso-15-epi-3-oxa (or 4-oxa)-18-phenyl-19,20-dinor-PGF$_{1\alpha}$ and -PGF$_{1\beta}$, 5,6-dehydro-3-oxa (or 4-oxa)-18-phenyl-19,20-dinor-PGF$_{2\alpha}$ and -PGF$_{2\beta}$, 5,6-dehydro-15-epi-3-oxa (or 4-oxa)-18-phenyl-19,20-dinor-PGF$_{2\alpha}$ and -PGF$_{2\beta}$, 5,6-dehydro-8-iso-3-oxa (or 4-oxa)-18-phenyl-19,20-dinor-PGF$_{2\alpha}$ and -PGF$_{2\beta}$, 5,6-dehydro-8-iso-15-epi-3-oxa (or 4-oxa)-18-phenyl-19,20-dinor-PGF$_{2\alpha}$ and -PGF$_{2\beta}$, 13,14-dihydro-3-oxa (or 4-oxa)-18-phenyl-19,20-dinor-PGF$_{1\alpha}$ and -PGF$_{1\beta}$, 13,14-dihydro-15-epi-3-oxa (or 4-oxa)-18-phenyl-19,20-dinor-PGF$_{1\alpha}$ and -PGF$_{1\beta}$, 13,14-dihydro-8-iso-3-oxa (or 4-oxa)-18-phenyl-19,20-dinor-PGF$_{1\alpha}$ and -PGF$_{1\beta}$, 13,14-dihydro-8-iso-15-epi-3-oxa (or 4-oxa)-18-phenyl-19,20-dinor-PGF$_{1\alpha}$ and -PGF$_{1\beta}$, are prepared by reduction of the corresponding 3-oxa or 4-oxa 17-phenyl-18,19,20-trinor- or 18-phenyl-19,20-dinor-PGE type methyl ester or free acid.

Also following the procedure of Examples 8 and 10, each of the other 3-oxa or 4-oxa phenyl-substituted PGE-type esters and free acids defined above in and after Examples 6 and 7, and hereafter in Examples 14 and 15, is transformed to the corresponding 3-oxa or 4-oxa phenyl-substituted PGF α-type and PGF β-type ester and free acid.

EXAMPLE 11 dl-15-dehydro-3-oxa-17-phenyl-18,19,20-trinor-PGF$_{1\alpha}$ Ethyl Ester (Formula LXXXIII (Chart J): E is trans —CH=CH—; Q is

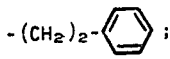

R$_1$ is ethyl; R$_2$ is hydrogen; V is —(CH$_2$)$_3$—O—CH$_2$—; and ~ is alpha).

A solution of dl-15-epi-3-oxa-17-phenyl-18,19,20-trinor-PGF$_{1\alpha}$ ethyl ester (566 mg.) in 24 ml. of dioxane is stirred at 50° C. under nitrogen and 2,3-dichloro-5,6-dicyano-1,4-benzoquinone (0.37 g.) is added. The mixture is stirred at 50° C. for 24 hours, cooled to room temperature, and filtered. The filter cake is washed with tetrahydrofuran, and the filtrate and wash are combined and concentrated under reduced pressure. The residue is taken up in dichloromethane and washed with brine, then dried over sodium sulfate and evaporated under reduced pressure. The residue is chromatographed over 90 g. of silica gel wet-packed in 8% ethanol in dichloromethane, eluting with 300 ml. of 2%, 300 ml. of 3%, 225 ml. of 7.5% and 245 ml. of 10% ethanol in dichloromethane, taking 15-ml. fractions. Fractions 65–71 are evaporated to give 413 mg. of the desired dl-15-dehydro-3-oxa-17-phenyl-18,19,20-trinor-PGF$_{1\alpha}$ ethyl ester: NMR peaks at 7.22, 6.95–6.30 (multiplet), 4.35–3.97 (multiplet), 3.65–3.45 (triplet), 291, 1.66–1.42, and 1.36–1.13 (multiplet) δ.

EXAMPLE 12 dl-15-Methyl-3-oxa-17-phenyl-18,19,20-trinor-PGF$_{1\alpha}$ Ethyl Ester (Formula XIX: C$_n$H$_{2n}$ is —(CH$_2$)$_3$—; C$_t$H$_{2t}$ is ethylene; R$_1$ is ethyl; R$_2$, R$_4$, R$_5$, and R$_6$ are hydrogen; R$_3$ is methyl; s is zero; and ~ is alpha).

The steps shown in Chart J are followed. A solution of dl-15-dehydro-3-oxa-17-phenyl-18,19,20-trinor-PGF$_{1\alpha}$ ethyl ester (413 mg.), hexamethyldisilazane (3 ml.) and trimethylchlorosilane (0.5 ml.) in 20 ml. of tetrahydrofuran is allowed to stand at about 25° C. for 20 hours. The mixture is filtered twice through a bed of diatomaceous earth (Celite Filter Aid) and the filtrate is concentrated by evaporation under reduced pressure. Xylene (10 ml.) is added to the residue and removed by evaporation under reduced pressure. The residue is dissolved in anhydrous ether and 0.43 ml. of 3 M methyl magnesium bromide in ether is added. The mixture is allowed to stand 20 minutes at about 25° C. and poured into 100 ml. of saturated aqueous ammonium chloride. The ether layer is separated, the aqueous layer is extracted with ether, and the ether extracts are combined and washed with brine, dried over sodium sulfate, and evaporated under reduced pressure. The residue is dissolved in 300 ml. of ethanol and 30 ml. of water containing 3 drops of glacial acetic acid, and the mixture is stirred for 2 hours at about 25° C. The mixture is concentrated under reduced pressure to an aqueous residue and the residue is extracted with dichloromethane. The dichloromethane extract is evaporated under reduced pressure to give a residue which is chromatographed over 60 g. of silica gel wet-packed in 8% ethanol in dichloromethane, eluting with 200 ml. of 5% and 800 ml. of 10% ethanol in dichloromethane and taking 10-ml. fractions. Fractions 48–62 are evaporated to give 93 mg. of the desired dl-15-methyl-3-oxa-17-phenyl-18,19,20-trinor-PGF$_{1\alpha}$ ethyl ester: NMR peaks at 7.23, 5.64–5.52 (multiplet), 4.37–4.13 (multiplet), 4.08, 1.5, 1.35, 1.38–1.15 (multiplet) δ. Other fractions yield the 15-epi compound.

Following the procedures of Examples 11 and 12, but using dl-15-epi-3-oxa-17-phenyl-18,19,20-trinor-PGF$_{1\beta}$ ethyl ester instead of the PGF$_{1\alpha}$ compound, there is obtained first the 15-dehydro PGF$_{1\beta}$ compound, and finally the 15-methyl-3-oxa-17-phenyl-18,19,20-trinor-PGF$_{1\beta}$ ethyl ester, and its 15-epimer.

Likewise, using the corresponding 4-oxa PGF$_{1\alpha}$ or PGF$_{1\beta}$ compounds instead of the 3-oxa compounds, there are obtained the corresponding 15-dehydro 4-oxa PGF$_{1\alpha}$ or PGF$_{1\beta}$ compounds, and finally the 15-methyl-4-oxa-17-phenyl-18,19,20-trinor-PGF$_{1\alpha}$ or -PGF$_{1\beta}$ ethyl esters and their 15-epimers.

Likewise, using the corresponding 18-phenyl-19,20-dinor-PGF$_{1\alpha}$ or PGF$_{1\beta}$ compounds instead of the above 17-phenyl-18,19,20-trinor-PGF$_{1\alpha}$ or PGF$_{1\beta}$ compounds, there are obtained the corresponding 15-dehydro and 15-methyl 18-phenyl-19,20-dinor-PGF$_{1\alpha}$ or -PGF$_{1\beta}$ compounds, and their 15-epimers.

EXAMPLE 13

Ethyl 7-[Endo-6-(1,2-dihydroxy-4-phenylbutyl)3-oxobicyclo[3.1.0]hex-2α-yl]-3-oxa-cis-5-heptenoate (Formula XLV: Q is

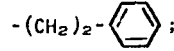

R$_2$, R$_3$, and R$_4$ are hydrogen; R$_{10}$ is ethyl; V is cis—CH=CH—CH$_2$—O—CH$_2$—; and ~ is endo and alpha).

The series of steps shown in Chart E is employed. The compound represented by Formula LVIII is prepared prior to forming the ketal XLIII.

A solution of potassium chlorate (10.0 g.) and osmium tetroxide (0.65 3.1.0]in 250 ml. of water is added with stirring to a solution of the Formula-L product (approximately 10.0 g.) of Example 1. The mixture is stirred vigorously for 5 hours at 50° C. Then, the cooled mixture is concentrated under reduced pressure. The residue is extracted repeatedly with dichloromethane, and the combined extracts are dried and evaporated. The residue is chromatographed on about 1000 g. of silica gel, and eluted successively with 3 l. of 10% ethyl acetate in a mixture of isomeric hexanes (Skellysolve B), with 5 l. of 25% ethyl acetate is Skellysolve B, and then with 50% ethyl acetate in Skellysolve B, collecting 500 ml. eluate fractions. Fractions 13–19 (50% ethyl acetate) are combined and evaporated to dryness to give endo-6(1,2-dihydroxy-4-phenylbutyl)-bicyclo[3.1.0]hexan-3-one (Formula LVIII).

A solution of the Formula-LVIII dihydroxy compound above (about 8.0 g.) and 700 mg. of potassium bisulfate in 140 ml. of acetone is stirred at 25° C. for 64 hours. Then, sodium carbonate monohydrate (710 mg.) is added, and the mixture is stirred 10 minutes. The acetone is evaporated at reduced pressure, and water is added. The aqueous solution is extracted respectedly with dichloromethane, and the extracts are combined, washed with water, dried, and evaporated.

The residue is chromatographed on 400 g. of silica gel, being eluted with 2 l. of 10% ethyl acetate in Skellysolve B, and then with 4 l. of 15% ethyl acetate in Skellysolve B. The 15% ethyl acetate eluates are evaporated to give endo-6-(1,2-dihydroxy-4-phenylbutyl)-bicyclo[3.1.0]hexan-3-one acetonide (Formula XIII).

Following the procedure of Example 3, but using the Formula-XLIII compound above instead of the endo-6-(cis-4-phenyl-1-butenyl)-bicyclo[3.1.0]hexan-3-one compound, the Formula-XLIII compound is alkylated with ethyl 7-iodo-3-oxa-cis-5-heptenoate to give ethyl 7-[endo-6-(1,2-dihydroxy-4-phenylbutyl)-3-oxobicyclo[3.1.0]hex-2α-yl]-3-oxa-cis-5-heptenoate acetonide (Formula XLIV).

Concentrated hydrochloric acid (2.5 ml.) is added to a solution of the Formula-XLIV product above (about 2.0 g.) in a mixture of 50 ml. of tetrahydrofuran and 2.5 ml. of water. The mixture is stirred at 25° C. under nitrogen for 6 hours. The resulting mixture is then evaporated under reduced pressure, and the residue is extracted with ethyl acetate. The extract is washed with saturated aqueous sodium chloride solution, dried, and evaporated to give ethyl 7-[endo-6-(1,2-dihydroxy-4-phenylbutyl)-3-oxobicyclo[3.1.0]hex-2α-yl]-3-oxa-cis-5-heptenoate (Formula XLV). Following the procedure of Example 13; but using Formula L exo reacts in place of the endo reactant from Example 1, there are obtained exo products in each intermediate and final step of Example 13.

With excess base (e.g., 26 g.) and a longer reaction time (e.g., 24 hours at 25°C.) during the alkylation step, the production of a substantial amount of the beta isomer is assured.

Following the procedure of Example 13, but using the intermediate Formula-L compound of Example 2, viz., endo6-(cis-5-phenyl-1-pentenyl)bicyclo[3.1.0]hexan-3-one, instead of the 4-phenyl-1-butenyl compound of EXAMPLE 1, there is obtained the Formula-XLV product, ethyl 7-[endo-6-(1,2-dihydroxy-5-phenylpentyl)-3-oxobicyclo[3.1.0]hex-2α-yl]-3-oxa-cis-5-heptenoate.

Also following the procedure of Example 13 but using the Formula-L products following Example 2 instead of the 4-phenyl-1-butenyl compound of Example 1, there are obtained other compounds corresponding to the Formula-XLV product of Example 13. For example, the 3-fluoro-3-phenyl-1-propenyl Formula-L compound yields ethyl 7-[endo-6-(1,2-dihydroxy-3-fluoro-3-phenylpropyl)-3-oxo-bicyclo[3.1.0]hex2α-yl]-3-oxa-cis-5-heptenoate. Depending upon the reactants and the conditions employed, as disclosed hereinabove, there are obtained products in the alpha or beta exo or endo configuration.

Also following the procedure of Example 13 but using in place of ethyl cis-7-iodo-3-oxa-cis-5-heptenoate in the alkylation step, ethyl 7-iodo-4-oxa-heptanoate, ethyl 3-fluoro-7-iodo-4-oxa-heptanoate, ethyl 7-iodo-3-oxa-trans5-heptenoate, and ethyl 7-iodo-3-oxa-5-heptynoate, there are obtained alpha and beta exo and endo compounds corresponding to the product of Example 13 with -(CH$_2$)$_3$-O-(CH$_2$)$_2$COOEt, -(CH$_2$)$_3$-O-CHF-CH$_2$COOEt, trans-CH$_2$CH=CH-CH$_2$-O- CH$_2$-COOEt, and -CH$_2$C≡C-CH$_2$-O-CH$_2$COOEt, respectively, wherein Et is ethyl, in place of the cis--CH$_2$CH=CH-CH$_2$-O-CH$_2$- moiety of the Example 13 product. In the same manner, but using FormulaLX-to-LXVII alkylating agents within the scope of the formula

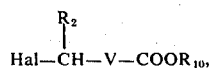

there are obtained the corresponding Formula-XLV products.

In the same manner, but using, according to Example 13, other esters of the Example 1 alkylating agent and of the other above-mentioned alkylating agents within the scope of R$_{10}$ as above-defined, e.g., the methyl, isopropyl, tertbutyl, octyl, β,β,β-trichloroethyl, cyclohexyl, benzyl, and phenyl esters, there are obtained the corresponding esters of these alpha and beta exo and endo Formula-XLIV bicyclo[3.1.0]hexane cyclic ketal alkylation products.

Also following the procedure of Example 13 but using in combination each of the above-described alternative FormulaXLIII bicyclo[3.1.0]hexane cyclic ketal reactants and each of the above-described omega-halo alkylation reactants within the scope of

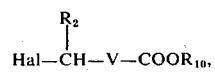

there are obtained FormulaXLIV compounds corresponding to the product of Example 13 but different therefrom with respect to both the carboxylateterminated side chain and the side chain attached to the cyclopropane ring of the product, and in their respective alpha or beta and exo or endo configuration.

Following the procedure of Example 13 but using in place of the acetonide each of the specific Formula-XLIV exo and endo, alpha and beta, saturated, cis and trans ethylenic, and acetylenic bicyclo[3.1.0]hexane cyclic ketal esters defined above, there are obtained the corresponding Formula-XLV dihydroxy compounds. R$_{10}$ persists unchanged during this transformation, e.g., the Formula-XLV β,β,β-trichloroethyl dihydroxy ester is obtained from the FormulaXLIV β,β,β-trichloroethyl cyclic ketal ester.

EXAMPLE 14

3-Oxa or 4-Oxa Phenyl-substituted PGE$_1$, PGE$_2$, dehydro PGE$_2$, and dihydro PGE$_1$type Esters.

The steps of Chart E are followed. Thus, following the procedure of Example 6, each of the Formula-XLV dihydroxy compounds of Example 13 is transformed to the corresponding Formula-XLVI bis-mesyl ester and thence to the Formula-XLVII PGE type compound. There are thus obtained the specific PGE type esters represented by FIGS. XI-XVIII, inclusive, e.g. the esters of 3-oxa (or 4-oxa)-17-phenyl-18,19,20-trinor-PGE$_1$; 3-oxa (or 4-oxa)-18-phenyl-19,20-dinor-PGE$_1$; 3-oxa (or 4-oxa)-17-phenyl-18,19,20-trinor-PGE$_2$; 3-oxa (or 4-oxa)-18-phenyl-19,20-dinor-PGE$_2$; 5,6-dehydro-3-oxa (or 4-oxa)-17-phenyl-18,19,20-trinor-PGE$_2$; 5,6-dehydro-3-oxa (or 4-oxa)-18-phenyl-19,20-dinor-PGE$_2$; 13,14-dihydro-3-oxa (or 4-oxa)-17-phenyl-18,19,20-trinor-PGE$_1$; and 13,14-dihydro-3-oxa (or 4-oxa)-18-phenyl-19,20-dinor-PGE$_1$; including their cis and trans forms, their 8-iso, and their 15-epi forms.

EXAMPLE 15

13,14-Dihydro-3-oxa-17-phenyl-18,19,20-trinor-PGE$_1$ (Formula XVII: C$_n$H$_{2n}$ is —(CH$_2$)$_3$—; C$_t$H$_{2t}$ is ethylene; R$_1$, R$_2$, R$_3$, R$_4$, R$_5$, and R$_6$ are hydrogen; s is zero; and ~ is alpha).

The procedures shown in Charts B and C are followed. A solution of 3-oxa-17-phenyl-18,19,20-trinor-PGE$_1$ (100 mg.) in 10 ml. of ethyl acetate is shaken with hydrogen at about one atmosphere pressure at 25°C. in the presence of 5% palladium on charcoal (15 mg.). One equivalent of hydrogen is absorbed in about 90 minutes. The hydrogenation is then stopped, and the catalyst is removed by filtration. The filtrate is evaporated, and the residue is chromatographed on 25 g. of silica gel, eluting with 50–100% ethyl acetate gradient in Skellysolve B. Those fractions shown by TLC to contain the desired product free of the starting product and dehydration products are combined and evaporated to give 13,14-dihydro-3-oxa-17-phenyl-18,19,20-trinor-PGE$_1$.

Following the procedure of Example 15, 3-oxa-17-phenyl-18,19,20-trinor-PGE$_1$ ethyl ester is reduced to 13,14-dihydro3-oxa-17-phenyl-18,19,20-trinor-PGE$_1$ ethyl ester. Likewise, 4-oxa-17-phenyl-18,19,20-trinor-PGE$_1$ ethyl ester is reduced to 13,14-dihydro-4-oxa-17-phenyl-18,19,20-trinor-PGE$_1$ ethyl ester. Also following the procedure of Example 15, 3-oxa-18-phenyl-19,20-dinor-PGE$_1$ ethyl ester is reduced to 13,14-dihydro-3-oxa-18-phenyl-19,20-dinor-PGE$_1$ ethyl ester.

Also following the procedure of Example 15, 3-oxa-17-phenyl-18,19,20-trinor-PGE$_2$, trans-5,6-dehydro-3-oxa-17-phenyl-18,19,20-trinor-PGE$_1$, and 5,6-dehydro-3-oxa-17-phenyl-18,19,20-trinor-PGE$_2$ are each reduced to 13,14-dihydro-3-oxa-17-phenyl-18,19,20-trinor-PGE$_1$, using two equivalents of hydrogen for the first two reactions, and three equivalents of hydrogen for the third. Likewise, the corresponding 4-oxa compounds are reduced to 13,14-dihydro-4-oxa-17-phenyl-18,19,20-trinor-PGE$_1$.

Also following the procedure of Example 15, the ethyl ester and the free acid form of the Formula XI-to-XVI PGE compounds in their various spatial configurations are transformed to the corresponding 13,14-dihydro PGE$_1$ compound by catalytic hydrogenation, using equivalents of hydrogen appropriate to the degree of unsaturation of the reactant, i.e., one equivalent for the PGE$_1$ type, two equivalents for the PGE$_2$ type and trans-5,6-dehydro-PGE$_1$ type, and three equivalents for the 5,6-dehydro-PGE$_2$ type.

Also following the procedure of Example 15, 3-oxa-phenyl-18,19,20-trinor-PGF$_{1\alpha}$ and its ethyl ester are reduced to 13,14-dihydro-3-oxa-17-phenyl-18,19,20-trinor-PGF$_{1\alpha}$ and its ethyl ester, respectively.

Also following the procedure of Example 15, the ethyl ester and the free acid form of the Formula XIX-to-XXIV PGF compounds in their various spatial configurations are transformed to the corresponding 13,14-dihydro PGF$_{1\alpha}$ or PGF$_{1\beta}$ compound by catalytic hydrogenation, using equivalents of hydrogen appropriate to the degree of unsaturation of the reactant.

EXAMPLE 16

13,14-Dihydro-3-oxa-17-phenyl-18,19,20-trinorPGA$_1$ (Formula XXXIII: C$_n$H$_{2n}$ is —(CH$_2$)$_3$—; C$_t$H$_{2t}$ is ethylene; R$_1$, R$_2$, R$_3$, R$_4$, R$_5$, and R$_6$ are hydrogen; s is zero; and ~ is alpha).

The procedures shown in Charts B and C are followed. A suspension of disodium azodiformate (50 mg.) in 5 ml. of absolute ethanol is added to a stirred solution of 3-oxa-17-phenyl-18,19,20-trinor-PGA$_1$ (50 mg.) in 10 ml. of absolute ethanol under nitrogen at 25° C. The mixture is made acid with glacial acetic acd, and then is stirred under nitrogen at 25° C. for 8 hours. The resulting mixture is evaporated under reduced pressure, and the residue is mixed with a mixture of diethyl ether and water (1:1). The diethyl ether layer is separated, dried, and evaporated to give the product 13,14-dihydro-3-oxa-17-phenyl-18,19,20-trinor-PMA$_1$.

Following the procedure of Example 16, 3l-oxa-17-phenyl-18,19,20-trinor-PGA$_1$ methyl ester is reduced to 13,14-dihydro-3-oxa-17-phenyl-18,19,20-trinor-PGA$_1$ methyl ester.

Also following the procedure of Example 16, 3-oxa-17-phenyl-18,19,20-trinor-PGA$_2$, trans-5,6-dehydro-3-oxa-17-phenyl-18,19,20-trinor-PGA$_1$, and 5,6-dehydro-3-oxa-17-phenyl-18,19,20-trinor-PGA$_2$ are each reduced to 13,14-dihydro-3-oxa-17-phenyl-18,19,20-trinor-PGA$_1$, using amounts of the disodium azodiformate reactant appropriate to the degree of unsaturation of the reactant.

Also following the procedure of Example 16, the methyl exter and the free acid form of the Formula XI-to-XVI PGE type compounds, the Formula XIX-to-XXIV PGF type compounds, the Formula XXVII-to-XXXII PGA type compounds, and the Formula XXXV-to-LX PGB type compounds are transformed to the corresponding 13,14-dihydro PGE$_1$, PGF$_1$, PGA$_1$, or PGB$_1$ type compound of diimide reduction, using amounts of disodium azodiformate reactant appropriate to the degree of unsaturation of the PGE, PGF, PGA, or PGB type reactant.

EXAMPLE 17 dl-4-Oxa-17-phenyl-18,19,20-trinor-PGF$_{2\alpha}$ Methyl Ester (Formula XXII: C$_q$H$_{2q}$ is methylene: C$_t$H$_{2t}$ is ethylene; R$_1$ is methyl; R$_2$, R$_3$, R$_4$, R$_5$, R$_6$, R$_7$, and R$_8$ are hydrogen; s is zero; and ~ is alpha.

The transformation shown in Chart D is used. dl-5,6-Dehydro-4-oxa-17-phenyl-18,19,20-trinor-PGF$_{2\alpha}$ methyl ester (200 mg.) in pyridine (4 ml.) and methanol (10 ml.) is hydrogenated in the presence of a 5%-palladium-on-barium sulfate catalyst (200 mg.) at 25° and atmospheric pressure. The reaction is terminated when one equivalent of hydrogen is absorbed. The mixture is filtered and evaporated. Ethyl acetate is added and residual pyridine is removed by addition of ice and 3 N. hydrochloric acid. The ethyl acetate layer is washed with 1 N. hydrochloric acid and then with saturated aqueous sodium chloride solution, dried, and evaporated to yield dl-4-oxa-17-phenyl-18,19,20-trinor-PGF$_{2\alpha}$ methyl ester.

Following the procedure of Example 17, the specific 5,6-dehydro-3-oxa (or 4-oxa) phenyl-substituted compounds following Example 10 are reduced to the corresponding PGF$_2$ compounds. Likewise, the specific 5,6-dehydro-3-oxa (or 4-oxa) phenyl-substituted PGE, PGA, and PGB compounds herein are reduced to the corresponding PGE$_2$, PGA$_2$, and PGB$_2$ compounds.

EXAMPLE 18

3-Oxa-17-phenyl-18,19,20-trinor-PGA$_1$ Ethyl Ester and Free Acid (Formula XXVII: C$_n$H$_{2n}$ is —(CH$_2$)$_3$—; C$_t$H$_{2t}$ is ethylene; R$_1$ is ethyl or hydrogen; R$_2$, R$_3$, R$_4$, R$_5$, and R$_6$ are hydrogen; s is zero; and ~ is alpha).

The procedures shown in Chart A are followed.

I. Using hydrochloric acid. A solution of 3-oxa-17-phenyl-18,19,20-trinor-PGE$_1$ ethyl ester (400 mg.) in a mixture of tetrahydrofuran (5 ml.) and 0.5 N hydrochloric acid (5 ml.) is maintained under nitrogen at 25° C. for 5 days. The resulting mixture is diluted with 1 volume of saturated aqueous sodium chloride solution and extracted with a mixture of diethyl ether and dichloromethane (3:1). The extract is washed with saturated aqueous sodium chloride solution, dried, and evaporated. The residue is dissolved in diethyl ether, and the solution is extracted with cold 5% aqueous sodium bicarbonate solution to give an aqueous layer A and a diethyl ether layer B. Aqueous layer A is acidified with dilute hydrochloric acid and then extracted with dichloromethane. This extract is washed with saturated aqueous sodium chloride solution, dried, and evaporated to give the product free acid. Diethyl ether layer B is evaporated to give the product ethyl ester.

II. Using acetic acid. A solution of 3-oxa-17-phenyl-18,19,20-trinor-PGE$_1$ ethyl ester in a mixture of a glacial acetic acid (9 ml.) and water (1 ml.) is heated under nitrogen at 60° C. for 18 hours. Then, the acetic acid and water are evaporated under reduced pressure, and the residue is chromatographed on 50 g. of acid-washed silica gel, eluting with a 25–100% gradient of ethyl acetate in Skellysolve B. The fractions containing the desired product free of starting material as shown by TLC are combined and evaporated to give the product, 3-oxa-17-phenyl-18,19,20-trinor-PGA$_1$ ethyl ester.

Following the procedure of Example 18, the 4-oxa-17-phenyl-18,19,20-trinor-PGE$_1$ free acid is transformed to 4-oxa-17-phenyl-18,19,20-trinor-PGA$_1$ free acid.

Also following the procedure of Example 18, the Formula XI-to-XVIII PGE compounds in their various spatial configurations are transformed to the corresponding Formula XXVII-to-XXXIV PGA compounds, either as esters or as free acids.

EXAMPLE 19

3-Oxa-17-Phenyl-18,19,20-trinor-PGA$_1$ Methyl Ester (Formula XXVII: C$_n$H$_{2n}$ is —(CH$_2$)$_3$—; C$_t$H$_{2t}$ is ethylene; R$_1$ is methyl; R$_2$, R$_3$, R$_4$, R$_5$, and R$_6$ are hydrogen; s is zero; and ~ is alpha).

The procedure shown in Chart E to prepare the compounds of Formula XLVIII is used. A solution of methyl 7-[endo-6-(1,2-dihydroxy-4-phenylbutyl)-3-oxobicyclo[3.1.0]hex-2α-yl]-3-oxa heptanoate bis(methanesulfonate) of Example 6 (Formula XLVI) (about 10 g.) in 75 ml. of acetone is mixed with 10 ml. of water and 20 ml. of saturated aqueous sodium bicarbonate solution. The mixture is refluxed under nitrogen for 4 hours. Then, the mixture is cooled, acidified with 5% hydrochloric acid, and extracted with ethyl acetate. The extract is washed with saturated aqueous sodium chloride solution, dried, and evaporated to give 3-oxa-17-phenyl-18,19,20-trinor-PGA$_1$ methyl ester.

Following the procedure of Example 19, each of the bismesylates defined in Example 14 is transformed to the corresponding PGA-type ester, including the β,β,β-trichloroethyl esters. Thereafter, each of the β,β,β-trichloroethyl esters is transformed to the corresponding PGA-type free acid by the procedure of Example 7.

EXAMPLE 20

3-Oxa-17-phenyl-18,19,20-trinor-PGB$_1$ (Formula XXXV: C$_n$H$_{2n}$ is —(CH$_2$)$_3$—; C$_t$H$_{2t}$ is ethylene; R$_1$, R$_2$, R$_3$, R$_4$, R$_5$, and R$_6$ are hydrogen; and s is zero).

The procedure shown in Chart A is followed. A solution of 3-oxa-17-phenyl-18,19,20-trinor-PGE$_1$ (200 mg.) in 100 ml. of 50% aqueous ethanol containing 10 grams of potassium hydroxide is kept at 25° C. for 10 hours under nitrogen. Then, the solution is cooled to 10° C. and neutralized by addition of 3 normal hydrochloric acid at 10° C. The resulting solution is extracted repeatedly with ethyl acetate, and the combined ethyl acetate extracts are washed with water and then with saturated aqueous sodium chloride solution, dried, and evaporated to give 3-oxa-17-phenyl-18,19,20-trinor-PGB$_1$.

Following the procedure of Example 20, 3-oxa-17-phenyl-18,19,20-trinor-PGA$_1$ is transformed to 3-oxa-17-phenyl-18,19,20-trinor-PGB$_1$.

Following the procedure of Example 20, the Formula XI-to-XVIII PGE compounds and the Formula XXVII-to-XXXIV PGA compounds are transformed to the corresponding PGB compounds.

EXAMPLE 21

7-[Endo-6-(1,2-dihydroxy-4-phenylbutyl)-3-oxobicyclo[3.1.0]hex-2α-yl]-3-oxa-5-heptenoic acid acetonide (Formula LXXII: Q is

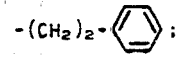

R$_2$, R$_3$, and R$_4$ are hydrogen; R$_{11}$ and R$_{12}$ are methyl; V is —CH=CH—CH$_2$—O—CH$_2$—; and ~ is endo and alpha.

The steps of this preparation are shown in Chart G. A solution of sodium borohydride (1.5 g.) in 10 ml. of water is added with stirring to a solution of Formula-LXVIII ethyl 7-[endo-6-(1,2-dihydroxy-4-phenyl-butyl)-3-oxobicyclo[3.1.0]hex-2α-yl]-3-oxa-5-heptenoate acetonide (5.0 g.) in 110 ml. of absolute ethanol at 0° C. The mixture is stirred for 2.5 hours at 0° to 5° C. Then, 40 ml. of acetone is added, and, after 5 minutes, the mixture is evaporated under reduced pressure. The residue is extracted with dichloromethane, and the extract is washed successively with dilute hydrochloric acid and saturated aqueous sodium chloride solution, dried, and evaporated to give the Formula-LXIX compound, ethyl 7-[endo-6-(1,2-dihydroxy-4-phenylbutyl)-3-hydroxy- bicyclo[3.1.0]hex-2α-yl]-3-oxa-5-heptenoate acetonide.

This cyclic ketal hydroxy ester is dissolved in a mixture of methanol (100 ml.) and 45% aqueous potassium hydroxide solution (30 ml.), and the solution is stirred under nitrogen at 25° C. for 15 hours. Two volumes of water are then added, and the mixture is acidified with cold hydrochloric acid and then extracted with a mixture of dichloromethane and diethyl ether (1:3). The extract is washed with saturated aqueous sodium chloride solution, dried, and evaporated to give the Formula-LXX compound, 7-[endo-6-(1,2-dihydroxy-4-phenylbutyl)-3-hydroxybicyclo[3.1.0-]hex-2α-yl]-3-oxa-5-heptenoic acid acetonide.

Jones reagent (7 ml.; Preparation 4) is added to a solution of this hydroxy acid in 120 ml. of acetone at 0° C. The mixture is stirred 5 minutes at 0° C. Then, 5 volumes of water are added, and the mixture is extracted with a mixture of dichloromethane and diethyl ether (1:3). The extract is washed successively with dilute hydrochloric acid and saturated aqueous sodium chloride solution, dried, and evaporated to give the Formula-LXXII compound, 7-[endo-6-(1,2-dihydroxy-4-phenylbutyl)-3-oxo-bicyclo[3.1.0]hex-2α-yl]-3-oxa-5-heptenoic acid acetonide.

Following the procedure of Example 21 but substituting for the Formula-LXVIII 3-oxobicyclo[3.1.0]hexane ester acetonide, each of the specific endo and exo, alpha and beta, saturated, cis and trans ethylenic, and acetylenic ester cyclic ketals described in and after Example 13 is reduced with sodium borohydride to give the corresponding Formula-LXIX 3-hydroxybicyclo[3.1.0]hexane ester cyclic ketal. That hydroxy ester is then saponified as in Example 21 to the corresponding Formula-LXX hydroxy acid. That hydroxy acid is then oxidized as in Example 21 to the corresponding Formula-LXXII 3-oxobicyclo[3.1.0]hexane acid cyclic ketal.

EXAMPLE 22

7-[Endo-6-(cis-4-phenyl-1-butenyl)-3-oxo-bicyclo[3.1.0]hex-2α-yl]-4oxaheptanoic acid (Formula LXXVIII: Q is

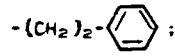

R$_2$, R$_3$, and R$_4$ are hydrogen; Z is —(CH$_2$)$_2$—O—(CH$_2$)$_2$—; and ~ is endo, and alpha.

The steps of this preparation are shown in Chart H. Following the procedure of Example 21, the Formula-LXXIV compound, methyl 7[endo-6-(cis-4-phenyl-1-butenyl)-3-oxobicyclo[3.1.0]hex-2α-yl]-4-oxa heptanoate is reduced with sodium borohydride to the Formula-LXXV compound, methyl 7-[endo-6-(cis-4-phenyl-1-butenyl)-3-hydroxybicyclo[3.1.0]hex-2α-yl]-4-oxaheptanoate. That hydroxy ester is then saponified as described in Example 21 to the Formula-LXXVI compound, 7-[endo-6-(cis-4-phenyl-1-butenyl)-3-hydroxybicyclo[3.1.0]hex-2α-yl]-4-oxa heptanoic acid. That hydroxy acid is then oxidized as described in Example 21 to the Formula-LXXVIII product, 7-[endo-6-(cis-4-phenyl-1butenyl)3-oxobicyclo[3.1.0]hex-2α-yl]-4-oxa heptanoic acid.

Following the procedure of Example 22, but using in place of the Formula-LXXIV 3-oxobicyclo[3.1.0]hexane ester, each of the specific Formula-LXXIV endo and exo, alpha and beta, saturated and acetylenic esters described in and following Examples 3 and 4 is reduced with sodium borohydride to give the corresponding Formula-LXXV 3-hydroxybicyclo[3.1.0] hexane ester. That hydroxy ester is then saponified as described in Example 21 to the corresponding Formula-LXXVI 3-hydroxybicyclo[3.1.0]hexane acid. That hydroxy acid is then oxidized as described in Example 21 to the corresponding Formula-LXXVIII 3-oxobicyclo[3.1.0-]hexane acid.

EXAMPLE 23

β,β,β- Trichloroethyl 7-[endo-6-(1,2-dihydroxy-4-phenybutyl)-3-hydroxybicyclo[3.1.0]hex-2α-yl]-3-oxa-5-heptenoate acetonide (Formula LXXI: Q is

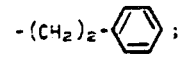

R$_2$, R$_3$, and R$_4$ are hydrogen; R$_{11}$ and R$_{12}$ are methyl; haloethyl is β,β,β-trichloroethyl; V is —CH=CH—CH$_2$—O—CH$_2$—; and ~ is endo, and alpha.

Successively, β,β,β-trichloroethanol (25 ml.), pyridine (15 ml.) and dicyclohexylcarbodiimide (4.0 g.) are added to a solution of Formula-LXX compound 7-[endo-6-(1,2-dihydroxy-4-phenylbutyl)-3-hydroxybicyclo[3.1.0]hex-2α-yl]-3-oxa-5-heptenoic acid acetonide (2.0 g.) in 100 ml. of dichloromethane. This mixture is stirred 3 hours under nitrogen at 25° C. Water (50 ml.) is then added, and the mixture is stirred 10 minutes. The dichloromethane is evaporated under reduced pressure, and the residue is extracted repeatedly with ethyl acetate. The combined extracts are washed with ice-cold 3N hydrochloric acid. Then, the extracts are washed successively with aqueous sodium bicarbonate solution and saturated aqueous sodium chloride solution, dried, and evaporated under reduced pressure. The residue is chromatographed on 600 g. of silica gel, eluting with 10 l. of a 20-100% ethyl acetate-Skellysolve B gradient, collecting 250-ml. fractions. The middle fractions which show the presence of a product on TLC (thin-layer chromatography) with the A-IX system are combined and evaporated under reduced pressue. The residue is chromatographed on 200 g. of silica gel impregnated with silver nitrate, eluting with 4 l. of a 20–100% ethyl acetate-Skellysolve B gradient, collecting 50-ml. fractions. The middle fractions which show a product free of starting materials on TLC with the A-IX system are combined and evaporated under reduced pressure to give the product, β,β,β-trichloroethyl 7-[endo-6-(1,2-dihydroxy-4-phenylbutyl)-3-hydroxybicyclo[3.1.0]hex-2α-yl]-3-oxa-5-heptenoate acetonide.

Following the procedure of Example 23, but using in place of the Formula-LXX 3-hydroxybicyclo[3.1.0-]hexane acid acetonide, each of the specific endo and exo, alpha and beta, saturated and unsaturated Formula-LXX hydroxy acid ketals defined after Example 21, there are obtained the corresponding β,β,β-trichloroethyl esters of those 3-hydroxybixyclo[3.1.0-]hexane acids.

Following the procedure of Example 23, but using in place of the Formula-LXX 3-hydroxybicyclo[3.1.0-]hexane acid ketal, each of the specific Formula-LXXII 3-oxo-acid ketals defined after Example 21, there are obtained the corresponding Formula-LXXIII β,β,β-trichloroethyl esters of those 3-oxo-acid ketals.

Following the procedure of Example 23 but using in place of the Formula-LXX 3-hydroxy-acid ketal, each of specific Formula-LXXVI 3-hydroxy and Formula-LXXVIII 3-oxo acids defined after Example 22, there are obtained the corresponding Formula-LXXVII and Formula-LXXIX $\beta,\beta,\beta$-trichloroethyl esters of those acids, respectively.

Following the procedures of Example 13 and 14, each of the Formula-LXXIII cyclic ketal haloethyl esters of Example 23 is transformed to the corresponding Formula-XLVII 3-oxa or 4-oxa phenyl-substituted PGE$_2$ $\beta,\beta,\beta$-trichloroethyl ester. Thence, following the procedure of Example 7, each of the esters is transformed to the 3-oxa or 4-oxa phenyl-substituted PGE$_2$ acid compound wherein R$_{10}$ of Formula XLVII is replaced with hydrogen.

Following the procedure of Examples 5 and 6 each of the Formula-LXXIX olefin haloethyl esters of Example 22 is transformed to the corresponding Formula-XLVII 3-oxa or 4-oxa phenyl-substituted PGE$_1$ $\beta,\beta,\beta$-trichloroethyl ester. Thence, following the procedure of Example 7, each of the esters is transformed to the 3-oxa or 4-oxa phenyl-substituted PGE$_1$ acid compound wherein R$_{10}$ of Formula XXXIII is replaced with hydrogen.

EXAMPLE 24 dl-15-Methyl-3-oxa-17-phenyl-18,19,20-trinor-PGE$_1$ Methyl Ester (Formula XI: C$_n$H$_{2n}$ is —(CH$_2$)$_3$—; C$_t$H$_{2t}$ is ethylene; R$_1$, and R$_3$ are methyl; R$_2$, R$_4$, R$_5$, and R$_6$ are hydrogen; $s$ is zero; and $\sim$ is alpha.

The process depicted in Chart I is used.

A solution of 15-methyl-3-oxa-17-phenyl-18,19,20-trinor-PGF$_1$ methyl ester (95 mg.) in 40 ml. of acetone is cooled to $-10°$ C. To it is added Jones reagent (0.1 ml. of a solution of 21 g. of chromic anhydride, 60 ml. of water, and 17 ml. of concentrated sulfuric acid), precooled to 0° C., with vigorous stirring. After 5 minutes at $-10°$ C., thin layer chromatography on silica gel (acetic acid:methanol: chloroform; 5:5:90) of a small portion of the reaction mixture indicates about 50% reaction completion. An additional 0.06 ml. of Jones reagent is added to the still cold reaction mixture with stirring, and the mixture is stirred an additional 5 minutes at $-10°$ C. Isopropyl alcohol (1 ml.) is added to the cold reaction mixture. After 5 minutes, the mixture if filtered through a layer of diatomaceous earth (Celite). The filtrate is concentrated at reduced pressure, and the residue is mixed with 5 ml. of saturated aqueous sodium chloride solution. The mixture is extracted repeatedly with ethyl acetate, and the combined extracts are washed with saturated aqueous sodium chloride solution, dried with anhydrous sodium sulfate, and concentrated at reduced pressure. The residue is chromatographed on 20 g. of neutral silica gel, eluting with 50% ethyl acetate in Skellysolve B. Evaporation of the eluates gives the product, dl-15-methyl-3-oxa-17-phenyl-18,19,20-trinor-PGE$_1$ methyl ester.

Following the procedure of Example 24, there is substituted for the 15-methyl-3-oxa-17-phenyl-18,19,20-trinor-PGF$_{1\alpha}$ methyl ester, the free acid, the propyl ester, the octyl ester, the cyclopentyl ester, the benzyl ester, the phenyl ester, the 2,4-dichlorophenyl ester, the 2-tolyl ester, or the $\beta,\beta,\beta$-trichloroethyl ester, there is obtained the corresponding dl-15-methyl-3-oxa-17-phenyl-18,19,20-trinor-PGE$_1$ compound.

Following the procedure of Example 24, but substituting for the 15-methyl-3-oxa-17-phenyl-18,19,20-trinor-PGF$_{1\alpha}$ methyl ester, the methyl ester of each of the 15-methyl-3-oxa-17-phenyl-18,19,20-trinor-PGF$_1\beta$, -PGF$_2\alpha$, -PGF$_2\beta$, -5,6-dehydro-PGF$_2\alpha$, -5,6-dehydro-PGF$_2\beta$, -dihydro-PGF$_1\alpha$, and -dihydro-PGF$_1\beta$ compounds in their various R or S configurations and optical isomers is transformed to the corresponding PGE type compound.

Following the procedure of Example 24, each of the various 15-alkyl-3-oxa-17-phenyl-18,19,20-trinor-PGF$_{1\alpha}$ methyl ester compounds, including the 15-ethyl, 15-propyl, 15-butyl, and 15-substituted isomeric forms of propyl and butyl, is transformed to the corresponding PGE type compound.

Also following the procedure of Example 24, each of the 15-alkyl PGF-type acids and esters within the scope of Formula LXXX (Chart I) is transformed to a 15-alkyl PGE-type acid or ester encompassed by Formula LXXXI.

EXAMPLE 25

15-Methyl-4-oxa-18-phenyl-19,20-dinor-PGA$_1$ Methyl Ester (Formula XXVII: C$_n$H$_{2n}$ is ethylene; C$_t$H$_{2t}$ is —(CH$_2$)$_3$—; R$_1$ and R$_3$ are methyl; R$_2$, R$_4$, R$_5$, and R$_6$ are hydrogen; $s$ is zero; and $\sim$ is alpha).

The process depicted in Chart K is used.

A mixture of 15-methyl-4-oxa-18-phenyl-19,20-dinor-PGE$_1$ methyl ester (6 mg.), dicyclohexylcarbodiimide (20 mg.), copper (II) chloride dihydrate (2 mg.), and diethyl ether (2 ml.) is stirred under nitrogen at 25° C. for 16 hours. Then, additional dicyclohexylcarbodiimide (20 mg.) is added, and the mixture is stirred an additional 32 hours at 25° C. under nitrogen. The resulting mixture is filtered, and the filtrate is evaporated under reduced pressure. The residue is chromatographed by preparative thin laye chromatography with the A-IX system to give 15-methyl-4-oxa-18-phenyl-19,20-dinor-PGA$_1$ methyl ester.

Following the procedure of Example 25, but substituting for the 4-oxa phenyl-substituted PGE$_1$ compound; the methyl esters of 15-methyl-4-oxa-17-phenyl-18,19,20-trinor-PGE$_2$, -5,6-dehydro-PGE$_2$, and -dihydro-PGE$_1$, there are obtained the corresponding Formula-LXXXVIII compounds, viz., the methyl esters of 15-methyl-4-oxa-17-phenyl-18,19,20-trinor-PGA$_2$, -5,6-dehydro-PGA$_2$, and -dihydro-PGA$_1$.

Also following the procedure of Example 25, but substituting for the phenyl-substituted PGE$_1$ compound, the methyl esters of 15-methyl-3-oxa-18-phenyl-19,20-dinor-PGE$_1$, -PGE$_2$, -5,6-dehydro-PGE$_2$, and -dihydro-PGE$_1$, there are obtained the corresponding Formula-LXXXVII compounds, viz., the methyl esters of 15-methyl-3-oxa-18-phenyl-19,20-dinor-PGA$_1$, -PGA$_2$, -5,6-dehydro-PGA$_2$, and -dihydro-PGA$_1$.

Also following the procedure of Example 25, each of the Formula-LXXXVII (Chart K) compounds defined above in Example 24 is transformed to the corresponding Formula-LXXXVIII compound.

EXAMPLE 26

Enzymatic Hydrolysis of 3-oxa-17-phenyl-18,19,20-trinor-PGE$_1$ Methyl Ester.

A. Enzyme preparation

A medium is prepared consisting of 2% corn steep liquor (a mixture of equal parts of cerelose and glucose in tap waer. This is brought to pH 4.5 by adding hydrochloric acid, and 1% of methyl oleate is added. Four 500 ml. flasks each containing 100 ml. of the above medium are inoculated with Cladosporium resinae (Cl-11, ATCC 11,274; and are placed on a shaker at room temperature (about 28° C.) for 4 days. The culture is then placed in 40 ml. centrifuge tubes and centrifuged at about 2000 rpm. in a clinical centrifuge. The liquid is decanted from the centrifuge tubes and the collected cells are washed with cold water. The washed cells from 2 centrifuge tubes are suspended in 50 ml. of ice cold 0.05 M pH 7.0 phosphate buffer and placed in small Waring blender cup chilled with ice. Glass beads are added and the suspended cells are churned in the blender for 15 minutes. The resulting suspension of broken cells is centrifuged in a clinical centrifuged at about 2000 r.p.m. for 15 minutes at room temperature, then the supernatant liquid is collected. This supernatant liquid contains Cladosporium resinae acylase and is used directly for the hydrolysis of alkyl esters or is stored, preferably frozen, until needed.

B. Esterase hydrolysis

Ten milliliters of the supernatant liquid containing Cladosporium resinae acylase, prepared as described in part A of this example and 50 mg. of 3-oxa-17-phenyl-18,19,29-trinor-$PGE_1$ methyl ester are shaken at room temperature under nitrogen for about 19 hours., then 70 ml. of acetone is added and the mixture is filtered giving a filtrate and an insoluble residue. The filtrate is evaporated under reduced pressure to a residue comprising 3-oxa-17-phenyl-18,19,20-trinor-$PGE_1$. This residue is chromatographed over 10 g. of acid-washed silica gel (Silicar CC-4, Mallinckrodt). Elution is with mixed hexanes (Skellysolve B) containing increasing amounts of ethyl acetate, collecting 50 ml. fractions. Those fractions containing 3(oxa-17-phenyl-18,19,20-trinor-$PGE_1$ are combined and evaporated to yield the product.

Following the procedure of Example 26, each of the specific methyl, ethyl, and other alkyl esters defined above in and after Examples 6, 14, and 15 is hydrolyzed enzymatically to the corresponding 3-oxa or 4-oxa phenyl-substituted PGE-type free acid.

Example 27

4-Oxa-17-phenyl-18,19,20-trinor-$PGB_1$Methyl Ester (Formula XXXVI: $C_mH_{2m}$ and $C_tH_{2t}$ are ethylene; $R_1$ is methyl; $R_2$, $R_3$, $R_4$, $R_5$, $R_6$, $R_7$, and $R_8$ are hydrogen; an $s$ is zero).

A solution of diazomethane (about 0.5 g.) in diethyl ether (25 ml.) is added to a solution of 4-oxa-17-phenyl-18,19,20-trinor-$PGB_1$ (50 mg.) in 25 ml. of a mixture of methanol and diethyl ether (1:1). The mixture is allowed to stand at 25° C. for 5 minutes. Then, the mixture is evaporated to give 4-oxa-17-phenyl-18,19,20-trinor-$PGB_1$ methyl ester.

Following the procedure of Example 27, each of the other specific phenyl-substituted PGB type, PGA type, PGE type, and PGF type free acids defined above is converted to the corresponding methyl ester.

Also following the procedure of Example 27, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 4-oxa-17-phenyl-18,19,20-trinor-$PGB_1$. In the same manner, each of the other specific phenyl-substituted PGB type, PGA type, PGE type, and PFG type free acids defined above is converted to the corresponding ethyl, butyl, 2-ethylhexyl, and cyclohexyl esters.

EXAMPLE 28

3-Oxa-17-phenyl-18,19,20-trinor-$PGE_1$ Methyl Ester Diacetate.

Acetic anhydride (5 ml.) and pyridine (5 ml.) are mixed with 3-oxa-17-phenyl-18,19,29-trinor-$PGE_1$ methyl ester (20 mg.), and the mixture is allowed to stand at 25° C. for 18 hours. The mixture is then cooled to 0° C., diluted with 50 ml. of water, and acidified with 5% hydrochloric acid to pH 1. That mixture is extracted with ethyl acetate. The extract is washed successively with 5% hydrochloric acid, 5% aqueous sodium bicarbonate solution, water, and saturated aqueous sodium chloride solution, dried and evaporated to give 3-oxa-17-phenyl-18,19,20-trinor-$PGE_1$ methyl ester diacetate.

Following the procedure of Example 28 but replacing the acetic anhydride with propionic anhydride, isobutyric anhydride, and hexanoic acid anhydride, there are obtained the corresponding dipropionate, diisobutyrate and dihexanoate derivatives of 3-oxa-17-phenyl-18,19,20-trinor-$PGE_1$ methyl ester.

Also following the procedure of Example 28, but replacing the 3-oxa-17-phenyl-18,19,20-trinor-$PGE_1$ compound with 3-oxa-17-phenyl-18,19,20trinor-$PGF_1\alpha$ and -$PGF_1\beta$, and 15-methyl-3-oxa17-phenyl-18,19,20-trinor-$PGF_{1\alpha}$ and -$PGF_{1\beta}$, there are obtained the corresponding triacetate derivatives of the 3-oxa-17-phenyl-18,19,20-trinor-PGF compounds.

Also following the procedure of Example 28, each of the phenyl-substituted PGE type, PGF type, PGA type and PGB type esters and free acids defined above is transformed to the corresponding acetates, propionates, isobutyrates, and hexanoates, the PGE type derivatives being dicarboxyacylates, the PGF type derivates being tricarboxyacylates, and the PGA type and PGB type derivatives being monocarboxyacylates.

EXAMPLE 29

3-Oxa-17-phenyl-18,19,20-trinor-$PGE_1$ Sodium Salt.

A solution of 3-oxa-17-phenyl-18,19,20-trinor-$PGE_1$ (100 mg.) in 50 ml. of a water-ethanol mixture (1:1) is cooled to 5° C. and neutralized with an equivalent amount of 0.1 N aqueous sodium hydroxide solution. The neutral solution is evaporated to give 3-oxa-17-phenyl-18,19,20-trinor-$PGE_1$ sodium salt.

Following the procedure of Example 29 but using potassium hydroxide, calcium hydroxide, tetramethylammonium hydroxide, and benzyltrimethylammonium hydroxide in place of sodium hydroxide, there are obtained the corresponding salts of 3-oxa-17-phenyl-18,19,20-trinor-$PGE_1$.

Also following the procedure of Example 29 each of the phenyl-substituted PGE type, PGF type, PGA type, and PGB type acids defined above is transformed to the sodium, potassium, calcium, tetramethylammonium, and benzyltrimethylammonium salts.

The various Preparations and Examples given above describe the preparation of racemic intermediates and final products. Each of the intermediates and final products named and defined above is also obtained in each of the enatiomeric forms, d and l, by resolution of that compound or by resolution of an intermediate used to prepare that compound. For example, d-3-oxa-17-phenyl-18,19,20-trinor-$PGA_1$ free acid is prepared by resolution of dl-3-oxa-17-phenyl-18,19,20-trinor-$PGA_1$ free acid (Example 18) or by dehydration as in Example 18 of optically active 3-oxa-17-phenyl-18,19,20-trinor-PGE$_1$ free acid with the same absolute configuration. These resolutions are carried out by procedures known in the art, and may be used to obtain prostaglandin-like materials having the spatial configuration of the natural prostaglandins, as typified by the following Example.

EXAMPLE 30

Natural Configuration
3-Oxa-17-phenyl-18,19,20-trinor-PGE$_2$ and -PGF$_2$ α
Methyl Esters (Formula XIII and XXI: C$_n$H$_{2n}$ is —(CH$_2$)$_3$—; C$_t$H$_{2t}$ is ethylene; R$_1$ is methyl; R$_2$, R$_3$, R$_4$, R$_5$, and R$_6$ are hydrogen; s is zero; and ∼ is alpha).

The process shown in Chart E is used to prepare the PGE$_2$-type compound first. The Formula-XLIV cyclic ketal intermediate wherein Q is

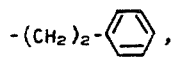

R$_2$, R$_3$, and R$_4$ are hydrogen; R$_{10}$, R$_{11}$, and R$_{12}$ are methyl; V is —CH=CH—CH$_2$ —O—CH$_2$—; and ∼ is endo and alpha is prepared following the procedures of Example 13.

The Formula-XLIV compound is resolved as its optical isomers by the method of Corey et al., J. Am. Chem. Soc. 84, 2938 (1962), by reacting this keto compound with optically active L(+)2,3-butanedithiol in the presence of p-toluene-sulfonic acid. The diastereomeric ketals are completely resolved on a preparative chromatographic column, and are then hydrolyzed separately, following the procedure of Example 13, to the Formula-XLV dihydroxy compounds. Transformation to the Formula-XLVII PGE$_2$-type compounds is accomplished by the procedures of Examples 13 and 14. Of the separate diastereoisomers, one corresponds to the configuration of natural PGE$_2$ and the other to its enantiomer. Conversion of the PGE$_2$-type compound having the configuration of the natural product to the PGE$_2$ -type methyl ester is done by borohydride reduction following the procedure of Example 8. The natural-configuration-PGE$_2$ -type free acid is formed from the methyl ester by saponification, following the procedure of Example 9.

EXAMPLE 31 ol-16,16-Dimethyl-3oxa-17-phenyl-18,19,20-trinor-PGE$_2$ Ethyl Ester (Formula XIII: C$_p$H$_{2p}$ is methylene; C$_t$H$_{2t}$ is —C(CH$_3$)$_2$—CH$_2$—; R$_1$ is ethyl; R$_2$, R$_3$, R$_4$, R$_5$, and R$_6$ are hydrogen; s is zero; and ∼ is alpha). Refer to Chart E.

A. (2,2-Dimethyl-3-phenylpropyl) triphenylphosphonium bromide.- a. (3-Bromo-2,2-dimethylpropyl)-benzene.- Following the procedure of Preparation 7 but replacing 4-phenyl-1-butanol with the equivalent amount of 2,2-dimethyl-3-phenyl-1-propanol, there is obtained (3-bromo-2,2-dimethylpropyl)benzene.

b. (2,2-Dimethyl-3-phenylpropyl)triphosphonium bromide.- Following the procedure of Preparation 5 but replacing (3-bromopropyl)benzene with the equivalent amount of (3-bromo-2,2-dimethylpropyl)benzene, there is obtained the corresponding phosphonium compound.

B. Endo-6-(cis-3,3-dimethyl-4-phenyl-1-butenyl)-bicyclo[3.1.0]hexan-3-one (Formula L).- Following the procedure of Example 1 but replacing that phosphonium halide with the above product of Example 31A, there is obtained the corresponding bicyclo olefin L.

C. Endo-6-(1.2-dihydroxy-3,3-dimethyl-4-phenyl-butyl)-bicyclo[3.1.0]hexan-3one acetonide (Formula XLIII)- Following the procedures of Example 13, the above Formula-L compound is transformed first to endo-6-(1,2-dihydroxy-3,3-dimethyl-4-phenylbutyl)-bicyclo[3.1.0]hexan-3-one (Formula LVIII) and thence to the corresponding bicyclo acetonide XLIII.

D. Ethyl 7-[endo-6(1,2-dihydroxy-3,3-dimethyl-4-phenylbutyl)-3-oxabicyclo[3.1.0]hex-2α-yl]-3-oxa-cis-5-heptenoate acetonide (Formula XLIV).- Following the procedure of Example 3, but using the Formula-XLIII compound above instead of the endo-6-(cis-4-phenyl-1-butenyl)-bicyclo[3.1.0]hexan-3-one compound, the Formula XLIII compound is alkylated with ethyl 7-iodo-3-oxa-cis-5-heptenoate to give the corresponding Formula-XLIV intermediate.

E. Title compound (Formula XIII (XLVII)).- Following the procedure of Example 13, the above Formula-XLIV compound is hydrolyzed with hydrochloric acid, water, and tetrahydrofuran to the corresponding glycol XLV.

Following the procedure of Example 6, but using the above Formula-XLV glycol instead of the ethyl 7-[endo-6-(1,2-dihydroxy-4-phenylbutyl)-3-oxobicyclo[3.1.0]hex-2α-yl]-3-oxaheptanoate, and finally subjecting the reaction product to silica gel chromatography, there is obtained the corresponding title compound and, separately, its 15-epimer.

EXAMPLE 32 dl-16,16-Dimethyl-3-oxa-17-phenyl-18,19,20-trinor-PGE$_2$ and -PGE$_2$ Ethyl Esters (Formula XXI: C$_p$H$_{2p}$ is methylene; C$_t$H$_{2t}$ is -C(CH$_3$)$_2$-CH$_2$-; R$_1$ is ethyl; R$_2$, R$_3$, R$_4$, R$_5$, and R$_6$ are hydrogen; s is zero; and ∼ is alpha or beta). Refer to Chart A.

Following the procedure of Example 8, dl-16,16-dimethyl-3oxa-17-phenyl-18,19,20-trinor-PGE$_2$ ethyl ester (Example 31 ) is reduced with sodium borohydride to a mixture of the title compounds which are separated by silica gel chromatography.

EXAMPLE 33 dl-16,16-Dimethyl-3-oxa-17-phenyl-18,19,20-trinor-PGA$_2$ Ethyl Ester (Formula XXIX: C$_p$H$_{2p}$ is methylene; C$_t$H$_{2t}$ is —C(CH$_3$)$_2$—CH$_2$—; R$_1$ is ethyl; R$_2$, R$_3$, R$_4$, R$_5$, and R$_6$ are hydrogen; s is zero; and ∼ is alpha).

Following the procedures of Example 18, dl-16,16-dimethyl-3-oxa-17-phenyl-18,19,20-trinor-PGE$_2$ ethyl ester (Example 31) is transformed by acid dehydration to the title compound.

EXAMPLE 34 dl-16,16-Dimethyl-3-oxa-17-phenyl-18,19,20-trinor-PGB$_2$ (Formula XXXVII: C$_p$H$_{2p}$ is methylene; C$_t$H$_{2t}$ is —C(CH$_3$)$_2$—CH$_2$—; R$_1$, R$_2$, R$_3$, R$_4$, R$_5$, and R$_6$ are hydrogen; and s is zero).

Following the procedure of Example 20, dl-16,16-dimethyl-3-oxa-17-phenyl-18,19,20-trinor-PGE$_2$ ethyl ester (Example 31) is transformed in basic solution to the title compound.

I claim:
1. A compound of the formula:

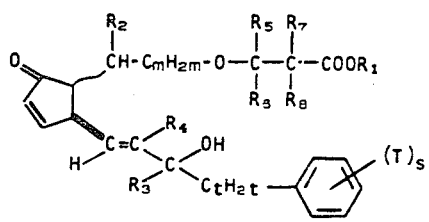

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the 3-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms; inclusive; wherein $C_mH_{2m}$ is alkylene of one to 9 carbon atoms, inclusive, with one to 4 carbon atoms, inclusive, between $-CHR_2-$ and $-O-$; wherein $C_tH_{2t}$ represents (1) a valence bond or (2) alkylene of one to 10 carbon atoms, inclusive, substituted with zero, one, or 2 fluoro, with one to 7 carbon atoms, inclusive, between $-CR_3OH-$ and the ring; wherein T is alkyl of one to 4 carbon atoms, inclusive, fluoro, chloro, trifluoromethyl, or $-OR_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

2. A compound according to claim 1 wherein

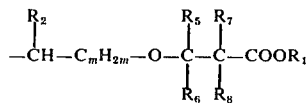

is $-(CH_2)_3-O-(CH_2)_2COOR_1$ wherein $R_1$ is defined in claim 18.

3. A compound according to claim 2 wherein $C_tH_{2t}$ is straight chain alkylene of one to 4 carbon atoms with or without a fluoro or alkyl substituent on the carbon atom adjacent to the hydroxysubstituted carbon atom.

4. A compound according to claim 3 wherein the side chain hydroxy is in S configuration.

5. A compound according to claim 4 wherein $R_4$ is hydrogen.

6. A compound according to claim 5 wherein $R_3$ is hydrogen.

7. A compound according to claim 6 wherein $C_tH_{2t}$ is $(CH_2)_d$ wherein d is one, 2, 3, or 4.

8. A compound according to claim 7 wherein d is 2.

9. 4-Oxa-17-phenyl-18,19,20-trinor-PGA$_1$, a compound according to claim 8.

10. 4-Oxa-17-phenyl-18,19,20-trinor-PGA$_1$, ethyl ester, a compound according to claim 8.

11. A compound according to claim 5 wherein $R_3$ is methyl.

12. A compound according to claim 11 wherein $C_tH_{2t}$ is $(CH_2)_d$ wherein d is one, 2, 3, or 4.

13. A compound according to claim 12 wherein d is 2.

14. 4-Oxa-15-methyl-17-phenyl-18,19,20-trinor-PGA$_1$, a compound according to claim 13.

15. 4-Oxa-15-methyl-17-phenyl-18,19,20-trinor-PGA$_1$, ethyl ester a compound according to claim 13.

16. A compound according to claim 3 wherein the side chain hydroxy is in R (epi) configuration.

17. A compound according to claim 16 wherein $R_4$ is hydrogen.

18. A compound according to claim 17 wherein $R_3$ is methyl.

19. A compound according to claim 18 wherein $C_tH_{2t}$ is $(CH_2)_d$ wherein d is one, 2, 3, or 4.

20. A compound according to claim 19 wherein d is 2.

21. 15-Epi-4-oxa-15-methyl-17-phenyl-18,19,20-trinor-PGA$_1$, a compound according to claim 20.

22. 15-Epi-4-oxa-15-methyl-17-phenyl-18,19,20-trinor-PGA$_1$, ethyl ester, a compound according to claim 20.

23. A compound of the formula:

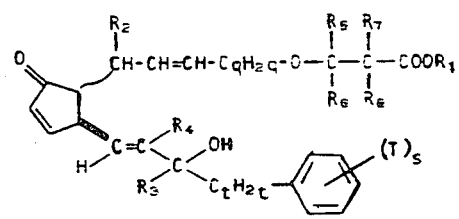

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_qH_{2q}$ is alkylene of one to 7 carbon atoms, inclusive, with one or 2 carbon atoms between $-CH=$\ $CH-$ and $-O-$; wherein $C_tH_{2t}$ represents (1) a valence bond or (2) alkylene of one to 10 carbon atoms, inclusive, substituted with zero, one, or 2 fluoro, with one to 7 carbon atoms, inclusive, between $-CR_3OH-$ and the ring; wherein T is alkyl of one to 4 carbon atoms. inclusive, fluoro, chloro, trifluoromethyl, or $-OR_a$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen, 24. A compound according to claim 23 wherein

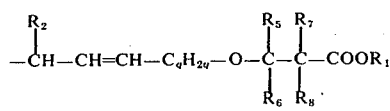

is $-CH_2-CH=CH-CH_2-O-(CH_2)_2-COOR_1$.

wherein $R_1$ is as defined in claim 23.

25. A compound of the formula:

101

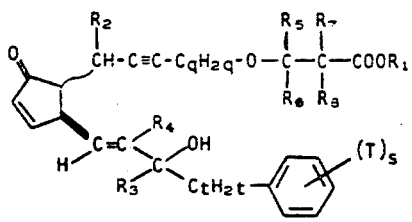

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the $\beta$-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_qH_{2q}$ is alkylene of one to 7 carbon atoms inclusive, with one or 2 carbon atoms between —C C— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or —OR$_9$, wherein $R_9$ is hydrogen, alkyl of one to 4 carbon atoms, inclusive, or tetrahydropyranyl, and $s$ is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

26. A compound according to claim 25 wherein

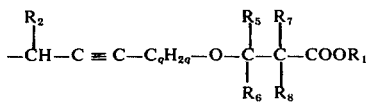

is

—CH$_2$—C≡C—CH$_2$—O—(CH$_2$)$_2$—COOR$_1$
wherein $R_1$ is as defined in claim 25.

27. A compound of the formula:

102

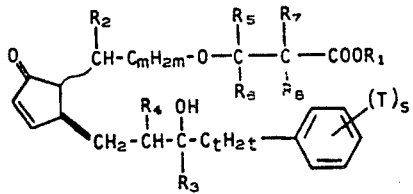

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the $\beta$-position with 3 chloro, 2 or 3 bromo, or 1, 2 or 3 iodo; wherein $R_2$, $R_3$, $R_4$, $R_5$, $R_6$, $R_7$, and $R_8$ are hydrogen or alkyl of one to 4 carbon atoms, inclusive; wherein $C_mH_{2m}$ is alkylene of one to 9 carbon atoms, inclusive, with one to 4 carbon atoms, inclusive, between —CHR$_2$— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or -OR$_9$, wherein $R_9$ is hydrogen, alkyl of one to 4 carbon atoms, inclusive, or tetrahydropyranyl, and $s$ is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

28. A compound according to claim 27 wherein

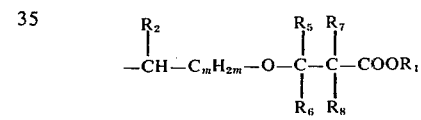

is

—CH$_2$)$_3$—O—(CH$_2$)$_2$—COOR$_1$,
wherein $R_1$ is defined in claim 27.

* * * * *